«12» United States Patent
Iranitalab et al.

«10» Patent No.: US 11,504,185 B2
«45» Date of Patent: Nov. 22, 2022

«54» METHODS AND DEVICES FOR ENDOVASCULAR ABLATION OF A SPLANCHNIC NERVE

«71» Applicant: Axon Therapies, Inc., New York, NY (US)

«72» Inventors: Pajhand Iranitalab, San Ramon, CA (US); Casey Andrew Miller, Campbell, CA (US); Thomas Ryan McGrath, Santa Clara, CA (US); Manuel Arzadon Javier, Santa Clara, CA (US); Anisha Bapna, Edison, NJ (US); Zoar Jacob Engelman, New York, NY (US); Howard Levin, Teaneck, NJ (US); Nicholas C. VanDillen, Lenexa, KS (US); Anne Marie Ahonen, Lenexa, KS (US)

«73» Assignee: Axon Therapies, Inc., New York, NY (US)

«*» Notice: Subject to any disclaimer, the term of this patent is extended or adjusted under 35 U.S.C. 154(b) by 0 days.

«21» Appl. No.: 17/304,007

«22» Filed: Jun. 11, 2021

«65» Prior Publication Data

US 2021/0298824 A1 Sep. 30, 2021

Related U.S. Application Data

«63» Continuation of application No. 17/152,665, filed on Jan. 19, 2021.

(Continued)

«51» Int. Cl.
*A61B 18/14* (2006.01)
*A61B 18/00* (2006.01)

(Continued)

«52» U.S. Cl.
CPC .. *A61B 18/1492* (2013.01); *A61B 2018/0022* (2013.01); *A61B 2018/00077* (2013.01);

(Continued)

«58» Field of Classification Search
CPC .... A61B 2218/002; A61B 2018/00863; A61B 2018/00577; A61B 2018/1467; A61B 18/1492

See application file for complete search history.

«56» References Cited

U.S. PATENT DOCUMENTS

| 3,301,258 A | 1/1967 | Werner |
| 4,403,985 A | 9/1983 | Boretos |

(Continued)

FOREIGN PATENT DOCUMENTS

| CN | 1219855 A | 6/1999 |
| CN | 101600471 A | 12/2009 |

(Continued)

OTHER PUBLICATIONS

Adamopoulos et al; Comparison of different methods for assessing sympathovagal balance in chronic congestive heart failure secondary to coronary artery disease; The American Journal of Cardiology; 70(20): pp. 1576-1582; Dec. 15, 1992.

(Continued)

*Primary Examiner* — Linda C Dvorak
*Assistant Examiner* — Christine A Dedoulis
«74» *Attorney, Agent, or Firm* — Shay Glenn LLP; Thomas M. Zlogar

«57» ABSTRACT

Systems, devices, and methods for transvascular ablation of target tissue. The devices and methods may, in some examples, be used for splanchnic nerve ablation to increase splanchnic venous blood capacitance to treat at least one of heart failure and hypertension. For example, the devices disclosed herein may be advanced endovascularly to a target (Continued)

vessel in the region of a thoracic splanchnic nerve (TSN), such as a greater splanchnic nerve (GSN) or a TSN nerve root. Also disclosed are methods of treating heart failure, such as HFpEF, by endovascularly ablating a thoracic splanchnic nerve to increase venous capacitance and reduce pulmonary blood pressure.

12 Claims, 19 Drawing Sheets

Related U.S. Application Data

(60) Provisional application No. 63/086,516, filed on Oct. 1, 2020, provisional application No. 62/962,627, filed on Jan. 17, 2020.

(51) Int. Cl.
*A61M 25/00* (2006.01)
*A61M 25/01* (2006.01)
*A61N 7/00* (2006.01)

(52) U.S. Cl.
CPC ............ *A61B 2018/00434* (2013.01); *A61B 2018/00577* (2013.01); *A61B 2018/00642* (2013.01); *A61B 2018/00672* (2013.01); *A61B 2018/00678* (2013.01); *A61B 2018/00708* (2013.01); *A61B 2018/00791* (2013.01); *A61B 2018/00863* (2013.01); *A61B 2018/00875* (2013.01); *A61B 2018/00982* (2013.01); *A61B 2018/1435* (2013.01); *A61B 2018/1467* (2013.01); *A61B 2218/002* (2013.01); *A61M 25/0052* (2013.01); *A61M 25/0108* (2013.01); *A61N 7/00* (2013.01); *A61N 2007/003* (2013.01)

(56) References Cited

U.S. PATENT DOCUMENTS

| | | |
|---|---|---|
| 5,447,529 A | 9/1995 | Marchlinski et al. |
| 5,454,840 A | 10/1995 | Krakovsky et al. |
| 5,458,626 A | 10/1995 | Krause |
| 5,462,545 A | 10/1995 | Wang et al. |
| 5,540,681 A | 7/1996 | Strul et al. |
| 5,569,198 A | 10/1996 | Racchini |
| 5,649,974 A | 7/1997 | Nelson et al. |
| 5,658,282 A | 8/1997 | Daw et al. |
| 5,704,908 A | 1/1998 | Hofmann et al. |
| 5,722,403 A | 3/1998 | McGee et al. |
| 5,740,808 A | 4/1998 | Panescu et al. |
| 5,797,903 A | 8/1998 | Swanson et al. |
| 5,830,213 A | 11/1998 | Panescu et al. |
| 5,836,874 A | 11/1998 | Swanson et al. |
| 5,840,076 A | 11/1998 | Swanson et al. |
| 5,846,239 A | 12/1998 | Swanson et al. |
| 5,860,974 A | 1/1999 | Abele |
| 5,868,736 A | 2/1999 | Swanson et al. |
| 5,871,483 A | 2/1999 | Jackson et al. |
| 5,891,136 A | 4/1999 | McGee et al. |
| 5,925,038 A | 7/1999 | Panescu et al. |
| 5,928,229 A | 7/1999 | Gough et al. |
| 5,961,513 A | 10/1999 | Swanson et al. |
| 6,044,846 A | 4/2000 | Edwards |
| 6,058,331 A | 5/2000 | King |
| 6,071,278 A | 6/2000 | Panescu et al. |
| 6,099,526 A | 8/2000 | Whayne et al. |
| 6,123,718 A | 9/2000 | Tu et al. |
| 6,165,172 A | 12/2000 | Farley et al. |
| 6,236,886 B1 | 5/2001 | Cherepenin et al. |
| 6,395,325 B1 | 5/2002 | Hedge et al. |
| 6,409,722 B1 | 6/2002 | Hoey et al. |
| 6,425,877 B1 | 7/2002 | Edwards |
| 6,454,766 B1 | 9/2002 | Swanson et al. |
| 6,475,213 B1 | 11/2002 | Whayne et al. |
| 6,569,160 B1 | 5/2003 | Goldin et al. |
| 6,656,174 B1 | 12/2003 | Hegde et al. |
| 6,658,279 B2 | 12/2003 | Swanson et al. |
| 6,658,929 B2 | 12/2003 | Atkinson |
| 6,668,198 B2 | 12/2003 | Swanson et al. |
| 6,736,810 B2 | 5/2004 | Hoey et al. |
| 6,743,197 B1 | 6/2004 | Edwards |
| 6,760,616 B2 | 7/2004 | Hoey et al. |
| 6,832,114 B1 | 12/2004 | Whitehurst et al. |
| 6,849,073 B2 | 2/2005 | Hoey et al. |
| 6,885,888 B2 | 4/2005 | Rezai |
| 6,890,315 B1 | 5/2005 | Levin et al. |
| 6,954,977 B2 | 10/2005 | Maguire et al. |
| 6,984,232 B2 | 1/2006 | Vanney et al. |
| 7,054,689 B1 | 5/2006 | Whitehurst et al. |
| 7,104,989 B2 | 9/2006 | Skarda |
| 7,149,574 B2 | 12/2006 | Yun et al. |
| 7,153,301 B2 | 12/2006 | Swartz et al. |
| 7,236,822 B2 | 6/2007 | Dobak, III |
| 7,239,912 B2 | 7/2007 | Dobak, III |
| 7,282,050 B2 | 10/2007 | Starkebaum et al. |
| 7,282,051 B2 | 10/2007 | Rioux et al. |
| 7,285,199 B2 | 10/2007 | Mitsuhashi et al. |
| 7,326,208 B2 | 2/2008 | Vanney et al. |
| 7,330,762 B2 | 2/2008 | Boveja et al. |
| 7,335,377 B2 | 2/2008 | Stern et al. |
| 7,367,972 B2 | 5/2008 | Francischelli et al. |
| 7,418,292 B2 | 8/2008 | Shafer |
| 7,427,280 B2 | 9/2008 | Gerber |
| 7,449,018 B2 | 11/2008 | Kramer |
| 7,529,582 B1 | 5/2009 | DiLorenzo |
| 7,532,938 B2 | 5/2009 | Machado et al. |
| 7,551,964 B2 | 6/2009 | Dobak, III |
| 7,599,736 B2 | 10/2009 | DiLorenzo |
| 7,623,924 B2 | 11/2009 | Narciso, Jr. |
| 7,689,276 B2 | 3/2010 | Dobak |
| 7,689,277 B2 | 3/2010 | Dobak, III |
| 7,702,386 B2 | 4/2010 | Dobak et al. |
| 7,736,362 B2 | 6/2010 | Eberl et al. |
| 7,769,442 B2 | 8/2010 | Shafer |
| 7,778,703 B2 | 8/2010 | Gross et al. |
| 7,860,570 B2 | 12/2010 | Whitehurst et al. |
| 7,865,237 B2 | 1/2011 | Machado et al. |
| 7,877,146 B2 | 1/2011 | Rezai et al. |
| 7,921,657 B2 | 4/2011 | Littrup et al. |
| 7,937,145 B2 | 5/2011 | Dobak |
| 8,007,496 B2 | 8/2011 | Rioux et al. |
| 8,155,744 B2 | 4/2012 | Rezai |
| 8,241,273 B2 | 8/2012 | Whayne et al. |
| 8,270,568 B2 | 9/2012 | Pitt |
| 8,295,926 B2 | 10/2012 | Dobak, III |
| 8,321,030 B2 | 11/2012 | Maniak et al. |
| 8,399,443 B2 | 3/2013 | Seward |
| 8,401,667 B2 | 3/2013 | Gustus et al. |
| 8,414,508 B2 | 4/2013 | Thapliyal et al. |
| 8,433,412 B1 | 4/2013 | Westlund et al. |
| 8,473,051 B1 | 6/2013 | Wessels et al. |
| 8,483,835 B2 | 7/2013 | Errico et al. |
| 8,611,496 B2 | 12/2013 | Terunuma et al. |
| 8,676,326 B1 | 3/2014 | Farazi |
| 8,676,362 B2 | 3/2014 | Gabel et al. |
| 8,798,738 B2 | 8/2014 | Machado et al. |
| 8,814,793 B2 | 8/2014 | Brabrand |
| 8,911,439 B2 | 12/2014 | Mayse et al. |
| 8,994,536 B2 | 3/2015 | Margon |
| 8,998,894 B2 | 4/2015 | Mauch et al. |
| 9,005,100 B2 | 4/2015 | Gnanashanmugam et al. |
| 9,022,948 B2 | 5/2015 | Wang |
| 9,028,472 B2 | 5/2015 | Mathur et al. |
| 9,033,969 B2 | 5/2015 | Azamian et al. |
| 9,037,259 B2 | 5/2015 | Mathur |
| 9,072,902 B2 | 7/2015 | Mathur et al. |
| 9,125,661 B2 | 9/2015 | Deem |
| 9,125,668 B2 | 9/2015 | Subramaniam et al. |
| 9,162,075 B2 | 10/2015 | Sluijter et al. |
| 9,174,050 B2 | 11/2015 | Mathur et al. |
| 9,199,091 B2 | 12/2015 | Danek et al. |

(56) References Cited

U.S. PATENT DOCUMENTS

| | | |
|---|---|---|
| 9,245,182 B2 | 1/2016 | Jania et al. |
| 9,278,196 B2 | 3/2016 | Fischell et al. |
| 9,326,814 B2 | 5/2016 | He et al. |
| 9,345,530 B2 | 5/2016 | Ballakur et al. |
| 9,345,900 B2 | 5/2016 | Wu et al. |
| 9,370,657 B2 | 6/2016 | Tehrani et al. |
| 9,439,580 B2 | 9/2016 | Hatlestad et al. |
| 9,439,598 B2 | 9/2016 | Shimada et al. |
| 9,592,386 B2 | 3/2017 | Mathur et al. |
| 9,603,659 B2 | 3/2017 | Subramaniam et al. |
| 9,743,845 B2 | 8/2017 | Wang |
| 9,757,193 B2 | 9/2017 | Zarins et al. |
| 9,895,539 B1 | 2/2018 | Heit et al. |
| 10,207,110 B1 | 2/2019 | Gelfand et al. |
| 10,507,058 B2 | 12/2019 | Govan et al. |
| 10,912,610 B2 | 2/2021 | Levin et al. |
| 2002/0165532 A1 | 11/2002 | Hill et al. |
| 2002/0198520 A1 | 12/2002 | Coen et al. |
| 2003/0109869 A1 | 6/2003 | Shadduck |
| 2003/0216792 A1 | 11/2003 | Levin et al. |
| 2004/0147837 A1 | 7/2004 | Macaulay et al. |
| 2004/0148019 A1 | 7/2004 | Vidlund et al. |
| 2004/0247849 A1 | 12/2004 | Truckai |
| 2005/0010095 A1 | 1/2005 | Stewart et al. |
| 2005/0203462 A1 | 9/2005 | Katoh et al. |
| 2005/0245923 A1 | 11/2005 | Christopherson et al. |
| 2006/0200121 A1 | 9/2006 | Mowery |
| 2006/0224118 A1 | 10/2006 | Morris et al. |
| 2006/0287649 A1 | 12/2006 | Omsby et al. |
| 2007/0167984 A1 | 7/2007 | Kieval et al. |
| 2007/0208333 A1* | 9/2007 | Uchida .............. A61B 18/1206 606/34 |
| 2007/0213704 A1 | 9/2007 | Truckai et al. |
| 2007/0224253 A1 | 9/2007 | Franklin |
| 2008/0114335 A1 | 5/2008 | Flickinger et al. |
| 2008/0125748 A1 | 5/2008 | Patel |
| 2008/0200972 A1 | 8/2008 | Rittman |
| 2009/0036794 A1 | 2/2009 | Stubhaug et al. |
| 2009/0280178 A1 | 11/2009 | Hedge et al. |
| 2010/0152731 A1 | 6/2010 | de la Rama et al. |
| 2010/0168820 A1 | 7/2010 | Maniak et al. |
| 2010/0241113 A1 | 9/2010 | Ingle |
| 2010/0249702 A1 | 9/2010 | Magana et al. |
| 2010/0286684 A1* | 11/2010 | Hata .................. A61B 18/1492 606/41 |
| 2010/0305664 A1 | 12/2010 | Wingeier et al. |
| 2010/0312295 A1 | 12/2010 | Vase et al. |
| 2011/0022127 A1 | 1/2011 | Averina et al. |
| 2011/0028962 A1 | 2/2011 | Werneth et al. |
| 2011/0098761 A1 | 4/2011 | Wittenberger et al. |
| 2011/0144639 A1 | 6/2011 | Govari |
| 2011/0224750 A1 | 9/2011 | Scheiner |
| 2011/0238083 A1 | 9/2011 | Moll et al. |
| 2011/0313417 A1 | 12/2011 | La Rama et al. |
| 2012/0065554 A1 | 3/2012 | Pikus |
| 2012/0089047 A1 | 4/2012 | Ryba et al. |
| 2012/0089123 A1* | 4/2012 | Organ ................ A61B 18/1492 604/523 |
| 2012/0136350 A1 | 5/2012 | Goshgarian et al. |
| 2012/0143293 A1 | 6/2012 | Mauch et al. |
| 2012/0265198 A1* | 10/2012 | Crow ................ A61B 18/1492 606/41 |
| 2012/0271162 A1 | 10/2012 | Liao et al. |
| 2012/0289369 A1 | 11/2012 | Fogarty |
| 2012/0296329 A1 | 11/2012 | Ng |
| 2013/0023758 A1 | 1/2013 | Fabro |
| 2013/0035682 A1 | 2/2013 | Weil |
| 2013/0096550 A1 | 4/2013 | Hill |
| 2013/0103026 A1 | 4/2013 | Kleshinski et al. |
| 2013/0226201 A1 | 8/2013 | Miller et al. |
| 2013/0237948 A1 | 9/2013 | Donders et al. |
| 2013/0282000 A1 | 10/2013 | Parsonage et al. |
| 2013/0289369 A1 | 10/2013 | Margolis |
| 2013/0296646 A1 | 11/2013 | Barbut et al. |
| 2013/0304047 A1 | 11/2013 | Grunewald et al. |
| 2013/0331813 A1 | 12/2013 | Barbut et al. |
| 2014/0005706 A1 | 1/2014 | Gelfand et al. |
| 2014/0025069 A1 | 1/2014 | Willard et al. |
| 2014/0031727 A1 | 1/2014 | Warnking |
| 2014/0058294 A1 | 2/2014 | Gross et al. |
| 2014/0058376 A1 | 2/2014 | Horn et al. |
| 2014/0058377 A1 | 2/2014 | Deem et al. |
| 2014/0067003 A1 | 3/2014 | Vase et al. |
| 2014/0088585 A1 | 3/2014 | Hill et al. |
| 2014/0088588 A1 | 3/2014 | Jarrard |
| 2014/0121641 A1 | 5/2014 | Fischell et al. |
| 2014/0180273 A1 | 6/2014 | Nair |
| 2014/0214129 A1 | 7/2014 | Waataja et al. |
| 2014/0276718 A1 | 9/2014 | Turovskiy et al. |
| 2014/0276742 A1 | 9/2014 | Nabutovsky et al. |
| 2014/0303617 A1 | 10/2014 | Shimada |
| 2015/0011834 A1 | 1/2015 | Ayala et al. |
| 2015/0088119 A1 | 3/2015 | Moss |
| 2015/0105659 A1 | 4/2015 | Salahieh et al. |
| 2015/0119674 A1 | 4/2015 | Fischell et al. |
| 2015/0141810 A1 | 5/2015 | Weadock |
| 2015/0141985 A1 | 5/2015 | Mayse et al. |
| 2015/0208949 A1 | 7/2015 | Tupin et al. |
| 2015/0223877 A1 | 8/2015 | Behar et al. |
| 2015/0245867 A1 | 9/2015 | Gross |
| 2015/0335286 A1 | 11/2015 | Boydell |
| 2016/0106499 A1 | 4/2016 | Ogata et al. |
| 2016/0151112 A1 | 6/2016 | Ku et al. |
| 2016/0158554 A1 | 6/2016 | Graig |
| 2016/0163062 A1 | 6/2016 | Garber |
| 2016/0192981 A1 | 7/2016 | Dimmer et al. |
| 2016/0199127 A1 | 7/2016 | Prutchi |
| 2016/0220851 A1 | 8/2016 | Mayse et al. |
| 2016/0296171 A1 | 10/2016 | Drori et al. |
| 2016/0317621 A1 | 11/2016 | Bright |
| 2016/0354137 A1 | 12/2016 | Fischell et al. |
| 2016/0374754 A1 | 12/2016 | Asirvatham et al. |
| 2017/0035990 A1 | 2/2017 | Swift |
| 2017/0049989 A1 | 2/2017 | Kapural |
| 2017/0202614 A1 | 7/2017 | Gross et al. |
| 2017/0216602 A1 | 8/2017 | Waataja et al. |
| 2017/0231490 A1 | 8/2017 | Toth et al. |
| 2017/0252101 A1 | 9/2017 | Hata et al. |
| 2018/0042669 A1* | 2/2018 | Curley .................. A61B 18/04 |
| 2018/0110561 A1* | 4/2018 | Levin .................. A61N 1/36017 |
| 2019/0069942 A1 | 3/2019 | Azamian et al. |
| 2019/0175912 A1 | 6/2019 | Gelfand et al. |
| 2019/0183569 A1 | 6/2019 | Panescu et al. |
| 2019/0298460 A1 | 10/2019 | Al-Jadda et al. |
| 2019/0343581 A1 | 11/2019 | Panescu et al. |
| 2020/0179045 A1 | 6/2020 | Levin et al. |
| 2020/0179047 A1 | 6/2020 | Panescu et al. |
| 2021/0128229 A1* | 5/2021 | Panescu ............ A61B 18/0218 |
| 2021/0220043 A1 | 7/2021 | Iranitalab et al. |
| 2021/0393326 A1 | 12/2021 | Levin et al. |
| 2022/0039863 A1 | 2/2022 | Bapana et al. |

FOREIGN PATENT DOCUMENTS

| | | |
|---|---|---|
| CN | 102670264 A | 9/2012 |
| CN | 102949176 A | 3/2013 |
| CN | 103118619 A | 5/2013 |
| CN | 103220984 A | 7/2013 |
| CN | 103313671 A | 9/2013 |
| CN | 103857353 A | 6/2014 |
| CN | 104066395 A | 9/2014 |
| CN | 104257426 A | 1/2015 |
| EP | 2662027 A1 | 11/2013 |
| EP | 2020943 B1 | 7/2015 |
| EP | 2755588 B1 | 5/2016 |
| EP | 2934357 B1 | 11/2017 |
| JP | 2008510530 A | 4/2008 |
| JP | 2009500052 A | 8/2009 |
| WO | WO99/12489 A2 | 3/1999 |
| WO | WO2004/039428 A2 | 5/2004 |
| WO | WO2008/049084 A2 | 4/2008 |
| WO | WO2014/150887 A1 | 9/2014 |
| WO | WO2014/197625 A1 | 12/2014 |
| WO | WO2016/084081 A2 | 6/2016 |

(56) References Cited

FOREIGN PATENT DOCUMENTS

| WO | WO2016/090175 A1 | 6/2016 | |
|---|---|---|---|
| WO | WO2016/132340 A1 | 8/2016 | |
| WO | WO2016/176333 A1 | 11/2016 | |
| WO | WO2017/074920 A1 | 5/2017 | |
| WO | WO2017/096007 A1 | 6/2017 | |
| WO | WO2018/023132 A1 | 2/2018 | |
| WO | WO-2018023132 A1 * | 2/2018 | ............ A61B 5/024 |
| WO | WO2018/125822 A2 | 7/2018 | |
| WO | WO2019/148094 A1 | 8/2019 | |
| WO | WO2020/257763 A1 | 12/2020 | |

OTHER PUBLICATIONS

Andren-Sandberg et al.: Thoracoscopic splanchnicectomy for chronic, severe pancreatic pain; In Seminars in Laparoscopic Surgery; 3(1); Sage CA: Thousand Oaks CA; Sage Publications; pp. 29-33; Mar. 1, 1996.

Baghdadi et al.; Systematic review of the role of thoracoscopic splanchnicectomy in palliating the pain of patients with chronic pancreatitis; Surgical endoscopy; 22(3); pp. 580-588; Dec. 28, 2007.

Barnes et al.; Haemodynamic responses to stimulation of the splanchnic and cardiac sympathetic nerves in the anaesthetized cat; The Journal of Physiology; 378; pp. 417-436; Sep. 1986.

Bauereisen et al.; The importance of mesenteric mechanoreceptors for the reflex innervation of resistance blood vessels capacity blood vessels in the splanchnic area; Pflugers Archiv fur die gesamte Physioiogie des Menschen und der Tiere, 276; pp. 445-455; Jan. 1963.

Bradley et al.; Nerve blocks and neuroablative surgery for chronic pancreatitis; World J. Surg.; 27(11); pp. 1241-1248; Nov. 1, 2003.

Brooksby et al.; Dynamic changes in splanchnic blood flow and blood volume in dogs during activation of sympathetic nerves; Circulation Research; XXIX(3); pp. 227-238; Sep. 1971.

Brunner et al.; Carotid sinus baroreceptor control of splanchnic resistance and capacity. Am J Physiol.; 255; pp. H1305-H1310; Dec. 1988.

Burkhoff et al.; Why does pulmonary venous pressure rise after on of LV dysfunction: a theoretical analysis; Am. J. Physiol.; 265(5, pt. 2); pp. H1819-H1828; Nov. 1993.

Buscher et al.; Bilateral thoracoscopic splanchnicectomy for pain in patients with chronic pancreatitis impairs adrenomedullary but not noradrenergic sympathetic function; Surgical Endoscopy; 26(8); p. 2183-2188; Aug. 2012.

Buscher et al.; Limited effect of thoracoscopic splanchnicectomy in the treatment of severe chronic pancreatitis pain: a prospective long-term analysis of 75 cases; Surgery; 143(6); pp. 715-722; Jun. 30, 2008.

Carneiro et al.; Change in liver blood flow and blood content in dogs during direct and reflex alteration of hepatic sympathetic nerve activity: Circulation Research: 40(2); pp. 150-158; Feb. 1, 1977.

Chatterjee et al.; Novel interventional therapies to modulate the autonomic tone in heart failure; JACC: Heart Failure; 3(10); pp. 786-802; Oct. 2015.

Cody et al.; Captopril kinetics in chronic congestive heart failure; Clin pharmacol Ther.; 32(6); pp. 721-726; Dec. 1982.

Crespy et al.; Anatomical bases of the transhiatus approach to the greater splanchnic nerve; Anatomia Clinica; 6(4); pp. 247-254; Dec. 1, 1984.

Cuschieri et al.; Bilateral endoscopic splanchnicectomy through a posterior thoracoscopic approach; Journal of the Royal College of Surgeons of Edinburgh; 39(1); pp. 44-47; Feb. 1994.

Dayal et al.: Variations in the formation of thoracic splanchnic nerves; European Journal of Anatomy; vol. 18; pp. 141-151; (year of pub. sufficiently earlier than effective US filing date and any foreign priority date) 2014.

Del Rio et al.; Carotid chemoreceptor ablation improves survival in heart failure: rescuing autonomic control of cardiorespiratory function; Journal of the American College of Cardiology; 62(25); pp. 2422-2430; Dec. 24, 2013.

Diedrich et al.; Segmental orthostatic fluid shifts; Clinical autonomic research; 14(3); pp. 146-147; Jun. 2004.

Edwards Lifesciences; ClearSight System (brochure; No. AR11578); 4 pgs.; (year of pub. sufficiently earlier than effective US filing date and any foreign priority date) © 2014.

Edwards; The glycogenolytic response to stimulation of the splanchnic nerves in adrenalectomized calves, sheep, dogs, cats and pigs; J Physiol.; 213; pp. 741-759; Mar. 1971.

Eisenberg et al.; Neurolytic celiac plexus block for treatment of cancer pain: A meta-analysis; Anesth Analg; 80(2); pp. 290-295; Feb. 1995.

Fallick et al.; Sympathetically mediated changes in capacitance: Redistribution of the venous reservoir as a cause of decompensation; Circulation: Heart Failure; 4; pp. 669-675; Sep. 2011.

Ferrara et al; Hemodynamics of the splanchnic and systemic circulation after hypotonic water load-comparison between normal subjects and patients with congestive heart failure; Acta Cardiologica; 38(2); pp. 81-88; Dec. 1982.

Fiaccadori et al.; Ultrafiltration in Heart Failure; Am Heart J.; 161(3); pp. 439-449; Mar. 2011.

Folkow et al.; The Effect of Graded Vasoconstrictor Fibre Stimulation on the Intestinal Resistance and Capacitance Vessels; Acta physiologica Scandinavica; 61; pp. 445-457; Aug. 1964.

Foss et al.; Reversal of genetic salt-sensitive hypertension by targeted sympathetic ablation; Hypertension; 61(4); pp. 806-811; Apr. 1, 2013.

Francis et al.; Clinical notes, suggestions and new instrument; JAMA; 134(1); pp. 20-21; May 3, 1947.

Fudim et al.; Role of volume redistribution in the congestion of heart failure; Journal of the American Heart Association; 6(8); e006817; 11 pages; Aug. 1, 2017.

Fujita; Splanchnic circulation following coeliac plexus block; Acta Anaesthesiol Scand.; 32(4); pp. 323-327; May 1988.

Gafanovich et al.; Chronic diarrhea-induced by celiac plexus block?; Journal of Clinical Gastroenterology; 26(4); pp. 300-302; Jun. 1, 1998.

GAMBRO®; Aquadex FlexFlowTM (brochure, No. L5189 Rev. B); 4 pgs.; © Aug. 2011.

Garcea et al.; Percutaneous splanchnic nerve radiofrequency ablation for chronic abdominal pain; ANZ Journal of Surgery; 75(8); pp. 640-644; Aug. 1, 2005.

Giraudo et al.; Endoscopic palliative treatment of advanced pancreatic cancer: Thoracoscopic splanchnicectomy and laparoscopic gastrojejunostomy; Annals of Oncology; 10(4); pp. S278-S280; Jan. 1, 1999.

Girouard et al.; Optical mapping in a new guinea pig model of ventricular tachycardia reveals mechanisms for multiple wavelengths in a single reentrant circuit; Circulation; 93(3); pp. 603-613; Feb. 1, 1996.

Goldblatt et al.; Studies on experimental hypertension II: The effect of resection of splanchnic nerves on experimental renal hypertension; The Journal of Experimental Medicine; 65(2); pp. 233-241; Feb. 1, 1937.

Goroszeniuk et al.; Permanent percutaneous splanchnic nerve neuromodulation for management of pain due to chronic pancreatitis: A case report; Neuromodulation; ;14(3); pp. 253-257; May-Jun. 2011.

Greenway et al.; Role of splanchnic venous system in overall cardiovascular homeostasis; In Federal Proceedings; 42(6); pp. 1678-1684; Apr. 1983.

Greenway; Blockade of reflex venous capacitance responses in liver and spleen by hexamethonium, atropine, and surgical section; Can. J. Physiol. Pharmacol.; 69(9); 1284-1287; Sep. 1991.

Griffith et al.; The vasomotor control of the liver circulation; American Journal of Physiology; 95(1); pp. 20-34; Oct. 1930.

Griffith et al.; Vasomotor Control of the Liver Circulation. Proceedings of the Society for Experimental Biology and Medicine; 27(7); pp. 673-674; Apr. 1930.

Herman et al.; Splenic afferents and some of their reflex responses; American Journal of Physiology-Regulatory, Integrative and Comparative Physiology; 242(3); pp. R247-R254; Mar. 1982.

(56) References Cited

OTHER PUBLICATIONS

Ihse et al.; Bilateral thoracoscopic splanchnicectomy: effects on pancreatic pain and function; Annals of Surgery; 230(6); pp. 785-791; Dec. 1, 1999.
Ischia et al; A new approach to the neurolytic block of the coeliac plexus: the transaortic technique; Pain; 16(4); pp. 333-341; Aug. 31, 1983.
Johnson et al.; An open randomized comparison of clinical effectiveness of protocol-driven opioid analgesia, celiac plexus block or thoracoscopic splanchnicectomy for pain management in patients with pancreatic and other abdominal malignancies; Pancreatology; 9(6); pp. 755-763; Jan. 1, 2009.
Kang et al.; Bilateral thoracoscopic splanchnicectomy with sympathectomy for managing abdominal pain in cancer patients; Am J Surg; 194(1); pp. 23-29; Jul. 2007.
Kapural et al.; Splanchnic block at T11 provides a longer relief than celiac plexus block from nonmalignant, chronic abdominal pain: Pain management; 9(2); pp. 115-121; Mar. 2019.
Katri et al.; Thoracoscopic splanchnicectomy for pain control in irresectable pancreatic cancer; Journal of Laparoendoscopic and Advanced Surgical Techniques; 18(2); pp. 199-203; Apr. 1, 2008.
Kaufman et al.; Effect of portal hypertension on splenic blood flow, intrasplenic extravasation and systemic blood pressure; American Journal of Physiology-Regulatory, Integrative and Comparative Physiology; 284(6); pp. R1580-R1585; Jun. 1, 2003.
Kimura et al.; Application of electrical impedance analysis for diagnosis of a pulmonary mass; Chest; 105(6); pp. 1679-1682; Jun. 1994.
King et al.; Splanchnic circulation is a critical neural target in angiotensin II salt hypertension in rats; Hypertension; 50(3); pp. 547-556; Sep. 2007.
Krishna et al.; Video-assisted thoracoscopic sympathectomy-splanchnicectomy for pancreatic cancer pain; Journal of Pain and Symptom Management; 22(1); pp. 610-616; Jul. 1, 2001.
Lang-Lazdunski et al.; Videothoracoscopic splanchnicectomy for intractable pain from adrenal metastasis; Ann Thorac Surg; 73(4); pp. 1290-1292; Apr. 2002.
Le Pimpec Barthes; Thoracoscopic splanchnicectomy for control of intractable pain in pancreatic cancer; The Annals of Thoracic Surgery; 65(3); pp. 810-813; Mar. 31, 1998.
Leksowski; Thoracoscopic splanchnicectomy for the relief of pain due to chronic pancreatitis; Surg Endosc.; 15(6); pp. 592-596; Jun. 2001.
Lica et al.; Thoracoscopic left splanchnicectomy—role in pain control in unresectable pancreatic cancer. Initial experience; Chirurgia; 109(3); pp. 313-317; May-Jun. 2014.
Lieberman et al.; Celiac plexus neurolysis with the modified transaortic approach; Radiology; 175(1); pp. 274-276; Apr. 1990.
Lillemoe et al; Chemical splanchnicectomy in patients with unresectable pancreatic cancer. A prospective randomized trial; Annals of Surgery; 217(5); pp. 447-457; May 1, 1993.
Lin et al.; Bilateral thoracoscopic lower sympathetic-splanchnicectomy for upper abdominal cancer pain. The European journal of surgery; Supplement 572; pp. 59-62; (year of pub. sufficiently earlier than effective US filing date and any foreign priority date) 1994.
Lonroth et al.; Unilateral left-side thoracoscopic sympathectomy for visceral pain control: a pilot study; The European Journal of Surgery; 163(2); pp. 97-100; Feb. 1, 1997.
Loukas et al.; A review of the thoracic splanchnic nerves and celiac ganglia; Clinical Anatomy; 23(5); pp. 512-522; Jul. 2010.
Maass-Moreno et al.; Carotid baroreceptor control of liver and spleen volume in cats; Am J Physiol; 260(1 Pt 2); pp. H254-H259; Jan. 1991.
Maher et al.; Thoracoscopic splanchnicectomy for chronic pancreatitis pain; Surgery; 120(4); pp. 603-610; Oct. 1996.
Mallet-Guy et al.; Treatment of chronic pancreatitis by unilateral splanchnicectomy; Archives of Surgery; 60(2); pp. 233-241; Feb. 1, 1950.

Masuda et al.; Splanchnicectomy for pancreatic cancer pain; BioMed Research International; Jan. 1, 2014.
Myhre et al.; Monitoring of celiac plexus block in chronic pancreatitis; Pain; 38(3); pp. 269-274; Sep. 1989.
Naidoo et al.; Thoracic splanchnic nerves: implications for splanchnic denervation; Journal of Anatomy; 199(5); pp. 585-590; Nov. 2001.
Nakazato et al; Extrinsic innervation of the canine abdominal vena cava and the origin of cholinergic vasoconstrictor nerves; J. Physiol.; 328; pp. 191-203; Jul. 1982.
Nath et al.; Biophysics and pathology of catheter energy delivery systems; Progress in Cardiovascular Diseases; XXXVII(4); pp. 185-204; Jan./Feb. 1995.
Norman: Posterior Mediastinum; As last known Jun. 6, 2013; retrieved from the internet (https:web.archive.org/web/20130606053828/http://www.wesnorman.com/thoraxlessons.htm); 11 pages; on Sep. 16, 2020.
Pan et al.; Differential responses of regional sympathetic activity and blood flow to visceral afferent stimulation; Am J Physiol Regul Integr Comp Physiol.; 280(6); pp. R1781-R1789; Jun. 2001.
Pietrabissa et al.; Thoracoscopic splanchnicectomy for pain relief in unresectable pancreatic cancer; Archives of Surgery; 135(3); pp. 332-335; Mar. 1, 2000.
Plancarte et al.; Management of chronic upper abdominal pain in cancer: transdiscai blockage of the splanchnic nerves; Regional Anesthesia and Pain Medicine; 35(6); pp. 500-506; Nov. 1, 2010.
Prasad et al.; Thoracoscopic splanchinicectomy as a palliative procedure for pain relief in carcinoma pancreas; Journal of Minimal Access Surgery; 5(2): pp. 37-39; (Author Manuscript); Apr. 1, 2009.
Raj; Celiac plexus/splanchnic nerve blocks; Techniques in Regional Anesthesia and Pain Management; 5(3); pp. 102-115; Jul. 2001.
Raj et al.; Radiofrequency lesioning of splanchnic nerves; Pain Practice; 2(3); pp. 242-247; Sep. 2002.
Raj et al.; The development of a technique for radiofrequency lesioning of splanchnic nerves; Current Review of Pain; 3(5); pp. 377-387; Oct. 1999.
Sadar et al.: Bilateral thoracic sympathectomy-splanchnicectomy in the treatment of intractable pain due to pancreatic carcinoma; Cleveland Clinic Quarterly; 41; pp. 185-188; (year of pub. sufficiently earlier than effective US filing date and any foreign priority date)1974.
Saenz et al.; Thoracoscopic splanchicectomy for pain control in patients with unresectable carcinoma of the pancreas; Surgical Endoscopy; 14(8); pp. 717-720; Aug. 1, 2000.
Sastre et al.; Transhiatal bilateral splanchnicotomy for pain control in pancreatic cancer: basic anatomy, surgical technique, and immediate results in fifty-one cases; Surgery; 111(6); pp. 640-646; Jun. 1992.
Scott-Douglas et al.; Effects of acute volume loading and hemorrhage on intestinal vascular capacitance: a mechanism whereby capacitance modulates cardiac output; Can. J. Cardiol.; 18(5); pp. 515-522; May 5, 2002.
Shimada et al.; Clinical evaluation of transhiatal bilateral splanchnicotomy for patients with intractable supramesenteric pain; Surgery Today; 29(11); pp. 1136-1140; Nov. 1999.
Smigielski et al.; Assessment of quality of life in patients with non-operated pancreatic cancer after videothoracoscopic splanchnicectomy; Videosurgery and Other Miniinvasive Techniques; 6(3); pp. 132-137; Sep. 1, 2011.
Stefaniak et al.; A comparison of two invasive techniques in the management of intractable pain due to inoperable pancreatic cancer; European Journal of Surgical Oncology; 31(7); pp. 768-773; Sep. 30, 2005.
Takahashi et al.; Thoracoscopic splanchnicectomy for the relief of intractable pain; Surgical Endoscopy; 10(1); pp. 65-68; Jan. 1, 1996.
Tavassoli et al.; Thoracoscopic splanchnicectomy for pain control in urresectable pancreatic cancer; Journal of Cardio-Thoracic Medicine; 1(2); pp. 53-56; Aug. 6, 2013.
Triposkiadis et al.; The sympathetic nervous system in heart failure: physiology, pathophysiology, and clinical implications; Journal of the American College of Cardiology; 54(19): pp. 1747-1762; Nov. 3, 2009.
Tsybenko et al.; Central nervous control of hepatic circulation; J Aut Nerv Sys; 33(3); pp. 255-266; May 1991.

(56) References Cited

OTHER PUBLICATIONS

Van Vliet et al.; Time course of renal responses to greater splanchnic nerve stimulation; American Journal of Physiology Regulatory, Integrative and Comparative Physiology; 260(5); pp. R894-R905; May 1991.

Verhaegh et al.; Percutaneous radiofrequency ablation of the splanchnic nerves with chronic pancreatitis: results of single and repeated procedures in 11 patients; Pain Practice; 13(8); pp. 621-626; (Author Manuscript); Nov. 1, 2013.

Wilkins et al.; The effect of splanchnic sympathectomy in hypertensive patients upon estimated hepatic blood flow in the upright as contrasted with the horizontal position; Journal of Clinical Investigation; 30(3); pp. 312-317; Mar. 1951.

Worsey et al.; Thoracoscopic pancreatic denervation for pain control in irrsectable pancreatic cancer; British Journal of Surgery; 80(8); pp. 1051-1052; Aug. 1, 1993.

Wroclaw Medical Univ. (Poland); Removing a section of nerve visceral improved (press release; with machine translation); retrieved Oct. 10, 2016 from the internet. http://www.zdrowie.abc.com.pl/aktualnosci/wroclaw-usuniecie-fragmentu-nerwu-trzewnego-poprawilo-u-chorej-wydolnosc-serca,25247.html; 5 pgs.; Sep. 23, 2016.

Yan et al.; Neurolytic celiac plexus block for pain control in unresectable pancreatic cancer; Am J Gastroenterol; 102(2); pp. 430-438; Feb. 2007.

Levin et al.; U.S. Appl. No. 15/017,260 entitled "Devices And Methods For Treatment Of Heart Failure By Splanchnic Nerve Ablation," filed Feb. 5, 2016.

Levin et al.; U.S. Appl. No. 17/171,447 entitled "Devices and methods for treatment of heart failure by splanchnic nerve ablation," filed Feb. 9, 2021.

Levin et al.; U.S. Appl. No. 17/452,305 entitled "Devices, systems, and methods for treatment of heart failure by splanchnic nerve ablation," filed Oct. 26, 2021.

Piciucchi et al.; The azygos vein pathway: an overview from anatomical variations of pathological changes; Insights Imaging; 5(5); pp. 619-628; Oct. 2014.

\* cited by examiner

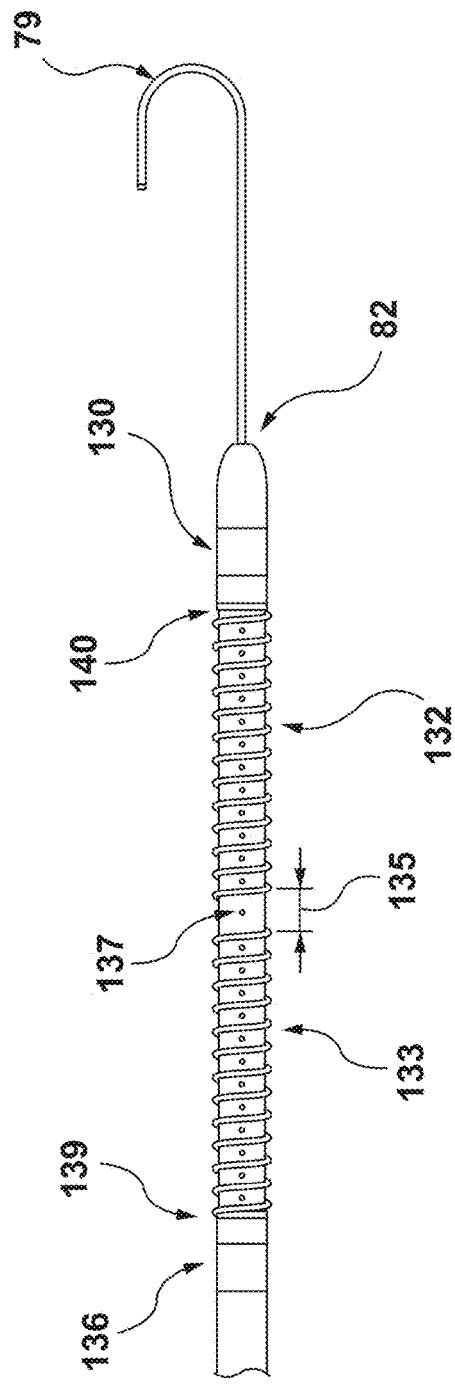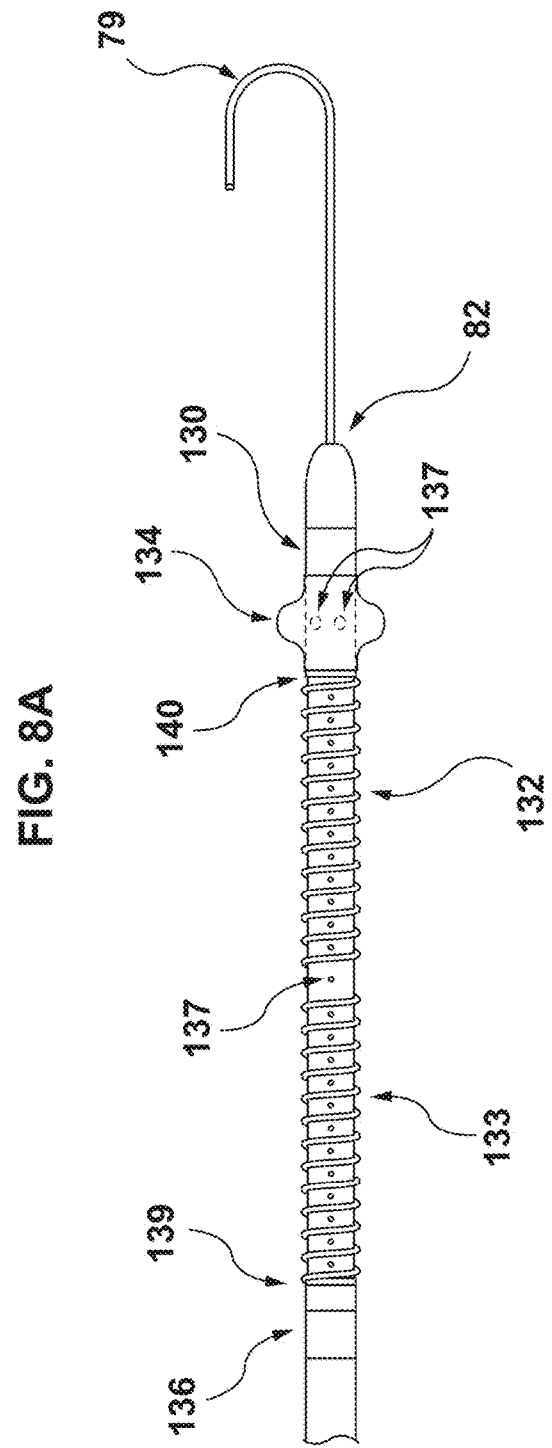
FIG. 8A
FIG. 8B

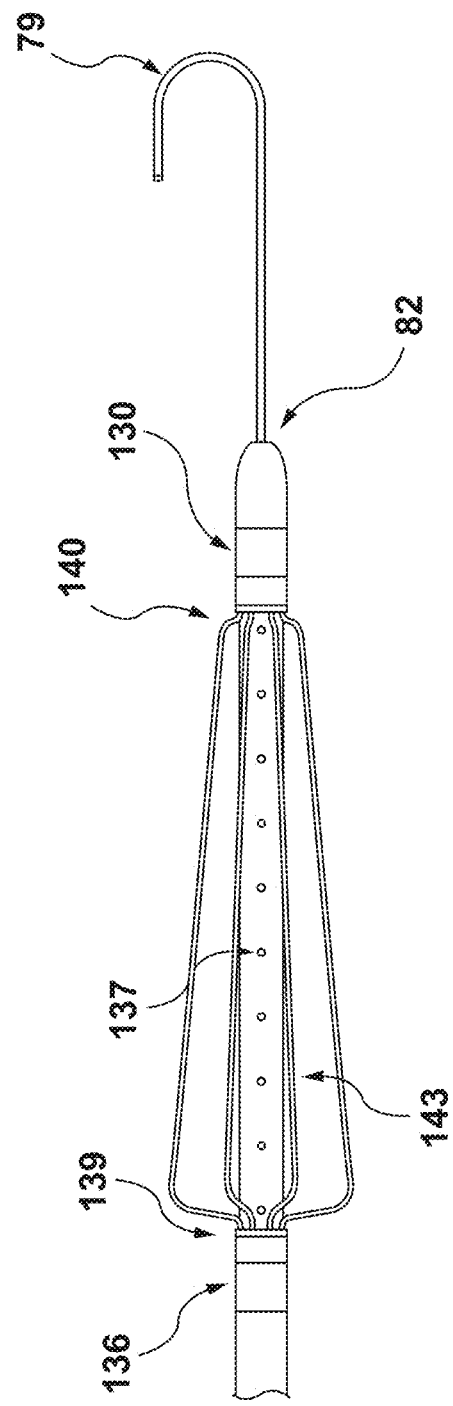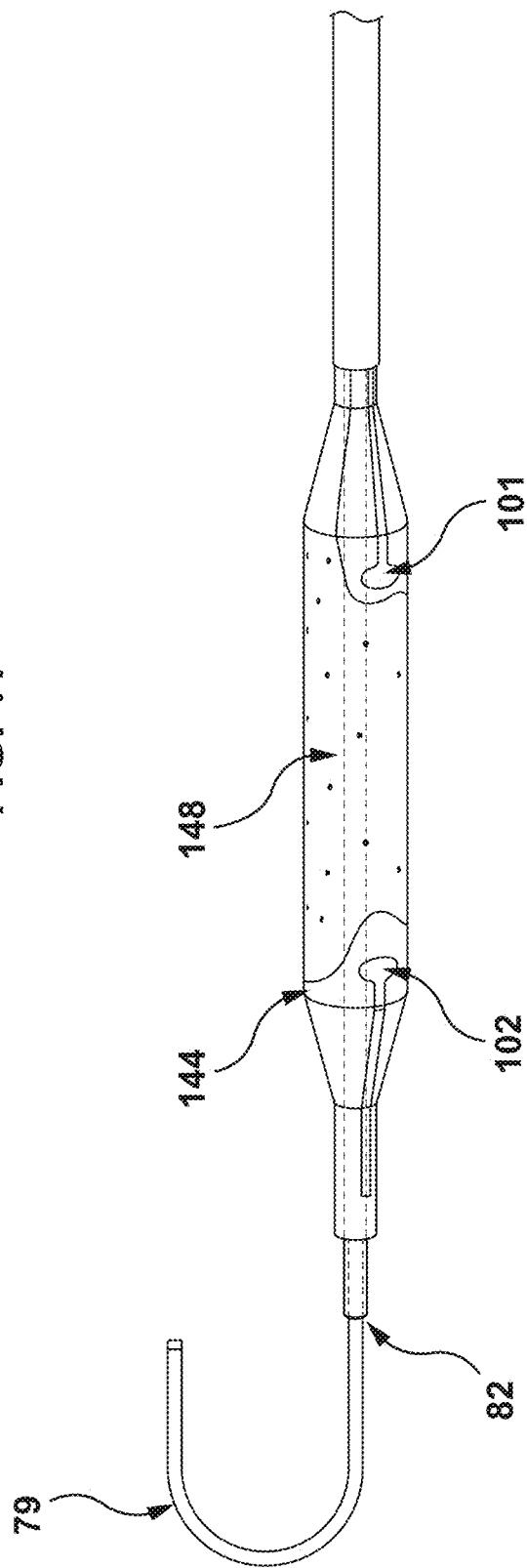

METHODS AND DEVICES FOR ENDOVASCULAR ABLATION OF A SPLANCHNIC NERVE

INCORPORATION BY REFERENCE

This application is a continuation of U.S. application Ser. No. 17/152,665 dated Jan. 19, 2021 which claims priority to U.S. Provisional Application No. 62/962,627, filed Jan. 17, 2020 and U.S. Provisional Application No. 63/086,516, filed Oct. 1, 2020, the disclosures of which are incorporated by reference herein in their entireties for all purposes.

All publications and patent applications mentioned in this specification are herein incorporated by reference to the same extent as if each individual publication or patent application was specifically and individually indicated to be incorporated by reference.

This disclosure is related by subject matter to the disclosure in U.S. Provisional Application 62/864,093, filed Jun. 20, 2019, U.S. Provisional Application 62/881,251, filed Jul. 31, 2019, U.S. Provisional Application 62/962,627 filed Jan. 17, 2020, U.S. Pub. Nos. US2019/0175912, US2019/0183569, U.S. Pat. Nos. 10,376,308, 10,207,110, application Ser. No. 16/510,503, 62/836,720, 62/837,090, 62/864,093, PCT/US2019/15400, PCT/US2020/038934, and PCT Pub. Nos. WO2018/023132, WO2019/118976, and WO/2020/257763, all of which are incorporated herein by reference in their entirety for all purposes.

BACKGROUND

Heart failure (HF) is a medical condition that occurs when the heart is unable to pump sufficiently to sustain the organs of the body. Heart failure is a serious condition and affects millions of patients in the United States and around the world.

One common measure of heart health is left ventricular ejection fraction (LVEF) or ejection fraction. By definition, the volume of blood within a ventricle immediately before a contraction is known as the end-diastolic volume (EDV). Likewise, the volume of blood left in a ventricle at the end of contraction is end-systolic volume (ESV). The difference between EDV and ESV is stroke volume (SV). SV describes the volume of blood ejected from the right and left ventricles with each heartbeat. Ejection fraction (EF) is the fraction of the EDV that is ejected with each beat; that is, it is SV divided by EDV. Cardiac output (CO) is defined as the volume of blood pumped per minute by each ventricle of the heart. CO is equal to SV times the heart rate (HR).

Cardiomyopathy, in which the heart muscle becomes weakened, stretched, or exhibits other structural problems, can be further categorized into systolic and diastolic dysfunction based on ventricular ejection fraction.

While a number of drug therapies successfully target systolic dysfunction and HFrEF, for the large group of patients with diastolic dysfunction and HFpEF no promising therapies have yet been identified. The clinical course for patients with both HFrEF and HFpEF is significant for recurrent presentations of acute decompensated heart failure (ADHF) with symptoms of dyspnea, decreased exercise capacity, peripheral edema, etc. Recurrent admissions for ADHF utilize a large part of current health care resources and could continue to generate enormous costs.

While the pathophysiology of HF is becoming increasingly better understood, modern medicine has, thus far, failed to develop new therapies for chronic management of HF or recurrent ADHF episodes. Over the past few decades, strategies of ADHF management and prevention have and continue to focus on the classical paradigm that salt and fluid retention is the cause of intravascular fluid expansion and cardiac decompensation.

Thus, there remains a need for improved therapies for heart failure patients that are safe and effective, and devices and systems that are adapted and configured to perform those therapies.

SUMMARY OF THE DISCLOSURE

The disclosure is related to methods of, devices for, and approaches for ablating a thoracic splanchnic nerve or a thoracic splanchnic nerve root. The ablations can be performed to treat at least one of hypertension and heart failure, but the general methods may also be used for other treatments as well. For example, the methods herein can be used in the treatment of pain, or even to generally benefit the subject to reducing the amount of blood that is expelled from the splanchnic bed into the central thoracic veins.

The treatments herein may be accomplished by increasing splanchnic capacitance. The therapies generally include ablating a patient's preganglionic thoracic splanchnic nerve or thoracic splanchnic nerve root to increase splanchnic capacitance, and thereby treat at least one of hypertension and heart failure.

Methods herein describe ablating thoracic splanchnic nerves, such as a greater splanchnic nerve or greater splanchnic nerve roots. While methods herein may provide specific examples of targeting greater splanchnic nerve or greater splanchnic nerve roots, it may be possible to alternatively, or in addition to, ablate other thoracic splanchnic nerves (e.g., lesser, least) to perform one or more treatments herein.

One aspect of the disclosure is a method of ablating tissue by positioning a medical device intravascularly in the vicinity of target tissue, and using the medical device to ablate tissue and create a lesion. One aspect of the disclosure a method of ablating tissue by positioning a medical device intravascularly into one or more target vessels, and using the medical device to ablate tissue and create a lesion. The methods herein can thus be described as methods that position a medical device near target tissue to be ablated and/or methods that position a medical device in one or more vessels, where the target tissue is relatively near to the target regions within the one or more vessels. Any of the method steps herein (including, for example without limitation, in the claims or the Description section) can be incorporated into any other method of use herein unless specifically indicated to the contrary herein.

One aspect of the disclosure is a method of ablating a greater splanchnic nerve or a greater splanchnic nerve root to increase splanchnic venous blood capacitance and/or venous compliance, the method including advancing a medical device into a first vessel, advancing the medical device at least partially into a second vessel, and delivering ablation energy from the medical device to create a lesion in tissue surrounding the first vessel.

In some embodiments the first vessel is an azygos vein and the second vessel is an intercostal vein. The intercostal vein may be one of the three lowest intercostal veins. The intercostal vein may be a T9, T10, or T11 intercostal vein.

The methods may include positioning a distal end of an ablation element in the second vessel and no more than 30 mm (e.g., 20 mm, 15 mm, 12 mm) from a junction between the first vessel and the second vessel when delivering the energy from the ablation element.

The methods may include a proximal portion of an ablation element being disposed in the second vessel when delivering energy.

The methods may include aligning or positioning the ablation element with respect to a boney landmark, such as a costovertebral joint at the same vertebral level at which the second vessel (e.g., intercostal vein) resides.

In some embodiments aligning or positioning the ablation element with respect to a boney landmark, such as a costovertebral joint, includes viewing the boney landmark with medical imaging such as fluoroscopy.

In some embodiments viewing the boney landmark with medical imaging such as fluoroscopy includes orienting the medical imaging perspective at an anterior oblique angle in a range of 25° to 65° from AP (e.g., in a range of 30° to 60°, in a range of 35° to 55°) toward the side of the patient where the target nerve resides.

In some embodiments viewing the boney landmark with medical imaging such as fluoroscopy includes orienting the medical imaging perspective approximately perpendicular to a line between the patient's first vessel (e.g., azygos vein) and the boney landmark (e.g., costovertebral joint).

In some embodiments aligning the ablation element with respect to a boney landmark includes aligning a radiopaque marker positioned on the catheter containing the ablation element with the boney landmark.

The method may include creating a lesion at a distance of 5 mm around the ablation element. Creating a lesion may include ablating a portion of a thoracic splanchnic nerve or a thoracic splanchnic nerve root, e.g., a greater splanchnic nerve or GSN root. A lesion may be a continuous lesion. The lesion may have a length from 5 mm to 25 mm, such as 10 mm to 25 mm, such as 15 mm to 20 mm. A lesion may be a circumferential lesion all the way around the second vessel. The lesion may, however, be less than circumferential all the way around the second vessel, such as 225 degrees or less, 180 degrees or less, 135 degrees or less, 90 degrees or less, 45 degrees or less.

The methods may include positioning an entire ablation element in the second vessel, while the method can also include positioning less than the entire length of the ablation element in the second vessel.

The methods may include performing an ablation process from within more than one target vessel, such as an intercostal vein or an azygos vein. The methods of ablation herein may also be performed in the second vessel.

The methods may include performing an ablation confirmation test, such as any of the tests herein. If desired or needed, an ablation element may be repositioned into a second target vessel, which may be an azygos vein or a different intercostal vein.

The methods can also include, prior to, during, and/or subsequent to delivering the ablation energy, delivering stimulation energy to first and second stimulation electrodes carried by the medical device. Delivering stimulation energy may help determine if the ablation element is in a target location within the intercostal vein, and/or if an ablation procedure was effective.

One aspect of the disclosure is a method that includes delivering an ablation catheter comprising an energy delivery element (or member) through a venous system of the patient, positioning the energy delivery element at least partially (optionally completely) inside a vein selected from T9, T10 and T11 intercostal veins, delivering ablation energy from the energy delivery element to create a continuous lesion having a depth of at least 5 mm and a length from 10 to 25 mm. The continuous lesion and its parameters can be formed by selecting or choosing certain energy delivery parameters that will create the lesion. In some embodiments, the lesion can extend from an ostium of an azygos vein to up to 20 mm along the intercostal vein. Any of the other method steps herein that are described in the context of other methods can be performed with this exemplary method.

In some alternative methods herein, a plurality of ablations (i.e., from ablation energy on to energy ablation off) can be performed within a single target vessel (e.g., an intercostal vein) to create a total lesion made from two or more lesions made from the plurality of ablations. The total lesion made from the plurality of lesions can have any of characteristics of the other lesions herein. For example, the total lesion can be continuous (made by the connection of a plurality of lesions created during different ablations), may be up to 20 mm long, can be circumferential (or not), etc. After a first ablation, the ablation device can be moved within the same vessel and create a second lesion, which may or may not overlap with a first lesion. This can be repeated as many times as desired. Any of the stimulation or testing steps herein can be performed before, during, or after any ablation step, even if a plurality of ablations are performed in a single vessel.

One aspect of the disclosure is a method of positioning an ablation catheter in a T9, T10, or T11 intercostal vein in a position for ablating a greater splanchnic nerve (GSN), the method including imaging a portion of a subject, the portion including at least one of a T9, T10, or T11 intercostal vein and a portion of the subject's spine; positioning a distal section of an ablation catheter in the T9, T10, or T11 intercostal vein; and positioning an ablation catheter radiopaque marker at a location based on the position of the radiopaque marker relative to an anatomical landmark, such as one or more of a portion of the spine, a rib, a costovertebral joint, an azygous vein, or an ostium between the azygous vein and the T9, T10, or T11 intercostal vein. The method may further include delivering energy from an ablation catheter ablation element to ablate tissue.

One aspect of the disclosure is a method that includes characterizing a relative position of a patient's azygos vein to determine if the azygos is centered or substantially centered, right-biased (to the patient's right of center), or left-biased (to the patient's left of center). The characterization step may occur while viewing a particular portion of the patient's anatomy, and from a particular viewpoint that allows the characterization to accurately take place. The method may further include positioning an ablation catheter based on the characterization step.

One aspect of this disclosure is a method of characterizing the position of a human patient's azygos vein relative to a portion of the patient's spine, comprising: imaging at least a portion of the patient's spine and vasculature, in particular the azygos vein and/or one or more intercostal veins, using an imaging device, in particular using a radiographic imaging device with a radiopaque contrast agent injected into the patient's vasculature, or imaging at least one radiopaque device, positioned in the azygos vein and/or in one or more intercostal veins, relative to a portion of the spine, using an imaging device, in particular using a radiographic imaging device, to thereby characterize the position of the patient's azygos vein relative to a midline of the spine, the radiopaque device optionally comprising a radiopaque portion of a guidewire; and determining if the azygos vein is centered, left-biased or right biased with respect to the midline of the vertebra based on one or more images generated by said imaging device. This aspect may further include a method of determining a proper position where a catheter should be inserted in a vasculature of a human patient, in particular in order to allow ablating a greater splanchnic nerve or greater splanchnic nerve roots, the method comprising determining where to place an ablation element of a catheter for transvascular ablation, in particular any of the ablation catheters herein, based on said determination of if the azygos vein is centered, left-biased or right biased with respect to the midline of the vertebra.

This aspect may further comprise determining where to place a radiopaque marker carried by the distal section of an ablation catheter, optionally a proximal radiopaque marker positioned proximal to any ablation element carried by the same distal section, based on said determination of if the azygos vein is centered, left-biased or right biased with respect to the midline of the vertebra.

One aspect of the disclosure is a method of determining proper positioning of a catheter inserted in a vasculature of a human patient, optionally of a catheter according to any of the claims or disclosure herein, wherein the catheter comprises an elongate shaft with a distal section carrying one or more ablation elements and a proximal radiopaque marker, with the distal section of the elongate shaft positioned in a T9, T10, or T11 intercostal vein; wherein the method comprises: determining if the azygos vein is centered, left-biased or right biased with respect to the midline of the vertebra, assessing the position of the proximal radiopaque marker relative to the midline of the vertebra, verifying if the catheter is properly positioned relative to a patient's anatomical landmark, wherein verifying comprises: considering that the catheter is properly positioned when one of the following circumstances takes place: if the azygos vein is right-biased, the proximal radiopaque marker is placed at the ostium of the intercostal vein, to the right of midline of the vertebra, if the azygos vein is centered or left-biased, the proximal radiopaque marker is aligned with the midline of the vertebra.

In any of the method aspects herein, the proximal radiopaque marker may be carried by the distal section and may be positioned proximal to all the ablation element(s). The proximal radiopaque marker may be positioned directly proximal to the ablation element or directly proximal to the most proximal of the ablation elements carried by the distal section of the catheter.

In any of the method aspects herein, the catheter may comprise a distal radiopaque marker positioned distal to all the ablation element(s) and wherein the step of verifying also includes: assessing the position of the distal radiopaque marker relative to the patient's costovertebral joint and/or rib, ascertaining that the distal radiopaque marker is spaced from the costovertebral joint and/or rib at least a prefixed threshold distance. The distal radiopaque marker may be positioned directly distal to the ablation element, or directly distal to the most distal of the ablation elements carried by the distal region of the catheter, and wherein ascertaining comprises ascertaining that the distal radiopaque marker is at least 3 mm, preferably at least 5 mm, far from the costovertebral joint.

In any of the method aspects herein, verifying may comprise considering that the catheter is not properly positioned when none of the following circumstances takes place: if the azygos vein is right-biased, the proximal radiopaque marker is placed at the ostium of the intercostal vein, to the right of midline of the vertebra, if the azygos vein is centered or left-biased, the proximal radiopaque marker is aligned with the midline of the vertebra.

In any of the method aspects herein, if it has been verified that the catheter is not properly positioned, the method may further include adjusting the position of the catheter by aligning the proximal radiopaque marker on the ablation catheter with the respective anatomical landmark, and/or by further distancing the distal radiopaque marker from the costovertebral joint.

In any of the method aspects herein, a step of determining if the azygos vein is centered, left-biased or right biased with respect to the midline of the vertebra may comprise: imaging at least a portion of the patient's spine and vasculature, in particular the azygos vein and/or one or more intercostal veins, using an imaging device, in particular using a radiographic imaging device with a radiopaque contrast agent injected into the patient's vasculature, or imaging at least one radiopaque device, positioned in the azygos vein and/or in one or more intercostal veins, relative to a portion of the spine, using an imaging device, in particular using a radiographic imaging device, to thereby characterize the position of the patient's azygos vein relative to a midline of the spine, the radiopaque device optionally comprising a radiopaque portion of a guidewire.

In any of the method aspects herein, a step of assessing the position of the proximal radiopaque marker relative to the midline of the vertebra may comprise imaging, using an imaging device, in particular using a radiographic imaging device, at least a portion of the catheter comprising the proximal radiopaque marker.

In any of the method aspects herein, a step of assessing the position of the distal radiopaque marker relative to the costovertebral joint may comprise imaging, using an imaging device, in particular using a radiographic imaging device, at least a portion of the catheter comprising the distal radiopaque marker.

One aspect of the disclosure is a method of determining proper positioning of a catheter inserted in a vasculature of a human patient, optionally of a catheter according to any one of the claims or disclosure herein, wherein the catheter comprises an elongate shaft with a distal section carrying one or more ablation elements and a distal radiopaque marker, with the distal section of the elongate shaft positioned in a T9, T10, or T11 intercostal vein; wherein the method comprises: determining the position of the distal radiopaque marker relative to the patient's costovertebral joint, verifying if the catheter is properly positioned relative to a patient's anatomical landmark, wherein verifying comprises: considering that the catheter is properly positioned when the distal radiopaque marker is spaced from the costovertebral joint at least a prefixed threshold distance. The distal radiopaque marker may be positioned directly distal to the ablation element, or directly distal to the most distal of the ablation elements carried by the distal section of the catheter, and wherein the prefixed threshold distance is at least 3 mm, preferably at least 5 mm.

In this aspect, if it has been verified that the catheter is not properly positioned, the method may further comprise adjusting the position of the catheter by further distancing the distal radiopaque marker from the costovertebral joint.

In this aspect, a step of determining the position of the distal radiopaque marker relative to the patient's costovertebral joint may comprises imaging at least a portion of the patient's spine and vasculature, in particular the azygos vein and/or one or more intercostal veins, using an imaging device, in particular using a radiographic imaging device with a radiopaque contrast agent injected into the patient's vasculature, or imaging at least one radiopaque device, positioned in the azygos vein and/or in one or more intercostal veins, relative to a portion of the spine, using an imaging device, in particular using a radiographic imaging device, to thereby characterize the position of the patient's azygos vein relative to a midline of the spine, the radiopaque device optionally comprising a radiopaque portion of a guidewire; and imaging, using an imaging device, in particular using a radiographic imaging device, at least a portion of the catheter comprising the distance radiopaque marker.

One aspect of the disclosure is an ablation catheter for transvascular ablation of thoracic splanchnic nerves, particularly for ablating a greater splanchnic nerve or greater splanchnic nerve roots, comprising: an elongate shaft having a length such that a distal section of the elongate shaft can be positioned in a T9, T10, or T11 intercostal vein, proximal and distal electrically conductive flexible ablation elements carried by the elongate shaft distal section, a length from a distal end of the distal ablation element to a proximal end of the proximal ablation element being from 10 mm-25 mm.

In this aspect the distal section of the elongate shaft may have an outer diameter from 1.5 mm to 3 mm.

In this aspect an axial spacing may exist between the proximal and distal ablation elements that is from 0.1 mm to 5 mm, such as 0.1 mm to 3 mm, such as 0.1 mm to 2 mm, such as 5 mm to 1-mm.

In this aspect the distal and proximal ablation elements may be electrodes.

In this aspect the distal and proximal ablation elements may each have a length, wherein the lengths are the same.

In this aspect the distal and proximal ablation elements may each have a length, wherein the lengths are not the same.

In this aspect the distal and proximal ablation elements may each have a length from 5 mm to 12 mm, such as from 6 mm to 10 mm, such as from 7 mm to 9 mm, such as any length in any of these ranges.

In this aspect the distal ablation element may have a helical configuration and wherein the proximal ablation element may a helical configuration. A helical configuration of the distal and proximal ablation elements may the same. Helical configurations of the distal and proximal ablation elements have one or more different features, such as one or more of coil direction (e.g. left-handed vs right-handed), pitch, or thickness.

In this aspect the distal and proximal ablation elements may each have curvilinear cross-sectional configurations.

In this aspect the distal and proximal ablation elements may each have rectilinear cross-sectional configurations.

In this aspect the distal and proximal ablation elements may be made from a superelastic material such as Nitinol.

In this aspect distal and proximal ablation elements may be sufficiently flexible and sized to allow the distal section to be advanced from an azygos vein into one of a T9, T10, or T11 intercostal vein.

In this aspect the distal and proximal ablation elements may each be attached to the shaft at distal and proximal end regions, but not in between the distal and proximal end regions.

In this aspect the catheter may further comprise a radiopaque marker. The radiopaque marker may be disposed distal to a distal end of the distal ablation element. The radiopaque marker may be 0 mm to 5 mm distal to the distal end of the distal ablation element, optionally 0 mm to 3 mm, or 0 mm to 2 mm. The radiopaque marker may be disposed proximal to a proximal end of the proximal ablation element. The radiopaque marker may be 0 mm to 5 mm proximal to the distal proximal of the distal ablation element, optionally 0 mm to 3 mm, or 0 mm to 2 mm.

In this aspect the distal and proximal ablation elements are each not configured to deploy to a deployed configuration.

In this aspect the distal and proximal ablation elements each have an operational configuration that is the same or substantially the same as a delivery configuration.

In this aspect the distal and proximal ablation elements each have an outer diameter in an operational state that is the same or substantially the same as an outer diameter in a delivery state.

In this aspect the distal and proximal ablation elements may each have expanded configurations different than delivery configurations.

In this aspect the catheter may further comprise a temperature sensor carried by the shaft. The temperature sensor may be disposed at a distal end of the distal ablation element. The temperature sensor may be disposed at a proximal end of the proximal ablation element. The catheter may comprise a second temperature sensor, the temperature sensor disposed at a distal end of the distal ablation element, the second temperature sensor disposed at a proximal end of the proximal ablation element.

In this aspect, the catheter may further comprise one or more irrigation ports in fluid communication with an irrigation lumen that is connectable to a fluid source at a proximal region of the ablation catheter. One of the one or more irrigation ports may be axially in between the distal and proximal ablation electrodes. Optionally none of the one or more irrigation ports may be disposed radially under an ablation element structure. One or more irrigation ports may be disposed between helical windings of the distal and proximal ablation electrodes. In a side view, an irrigation port may be disposed between every adjacent pair of ablation element helical sections of the distal ablation element and the proximal ablation element.

In this aspect the distal and proximal ablation elements may be electrically configured to be independently energized in monopolar mode.

In this aspect the distal and proximal ablation elements may be electrically configured to be energized in bipolar mode.

In this aspect the distal section may be no more than 7 cm from a distal tip of the ablation catheter.

In this aspect the distal and proximal ablation elements may be sized and adapted to create a continuous ablation having a length in a range of 5 mm to 25 mm, such as 10 to 25 mm, such as 15 mm to 20 mm.

In this aspect the distal section may be adapted for flexibly traversing a bend from an azygos vein to a T9, T10 or T11 intercostal vein.

In this aspect the catheter may further comprise a guidewire lumen within the elongate shaft and having a distal port at a distal tip of the catheter.

In this aspect the distal and proximal ablation elements may each comprise one or more of an RF ablation electrode, a coiled wire electrode, a laser cut RF electrode, a RF electrode printed with conductive ink, a RF electrode on an expandable balloon (e.g., conductive ink, flexible circuits,), a conductive membrane RF electrode, a RF electrodes on an expandable cage or mesh, an ultrasound ablation transducer, an electroporation electrodes, an cryoablation element, or a virtual RF electrode.

In this aspect the distal and proximal ablation elements may each be adapted and configured to deliver ablation energy circumferentially to create a circumferential lesion.

One aspect of the disclosure is an ablation catheter for transvascular ablation of thoracic splanchnic nerves, particularly for ablating a greater splanchnic nerve or greater splanchnic nerve roots, comprising: an elongate shaft having a length such that a distal section of the elongate shaft can be positioned in a T9, T10, or T11 intercostal vein, and an electrically conductive flexible ablation element carried by the elongate shaft distal section, the ablation element having a length from 10 mm-25 mm, and a radiopaque marker carried by the elongate shaft.

In this aspect the distal section of the elongate shaft may have an outer diameter from 1.5 mm to 3 mm.

In this aspect the radiopaque marker carried by the elongate shaft may be disposed from 0 mm to 5 mm from an end of the ablation element, such as from 0 to 4 mm, or from 0 to 3 mm, or 0 to 2 mm. The end may be a distal end of the ablation element. The end may be a distal end of a distal ablation electrode, and the ablation element may further comprising a proximal ablation electrode axially spaced from the distal ablation electrode.

In this aspect the end may be a proximal end of the ablation element.

In this aspect the catheter may further comprise a second radiopaque marker carried by the elongate shaft and disposed from 0 mm to 5 mm (e.g., 0 to 4 mm, 0 to 3 mm, or 0-2 mm from a second end of the ablation element).

In this aspect the ablation element may comprise distal and proximal ablation electrodes. The radiopaque marker may be distal to the distal ablation electrode, wherein catheter may include a second marker proximal to the proximal ablation electrode.

In this aspect, the radiopaque marker may be disposed from 0 mm to 3 mm from the end of the ablation element, optionally 1 mm.

In this aspect, the ablation element may comprise a distal ablation electrode axially spaced from a proximal ablation electrode. The distal and proximal ablation electrodes may each have a length, wherein the lengths are the same or wherein the lengths that are not the same. The distal and proximal ablation electrodes may each have a length from 5 mm to 12 mm. The distal and proximal ablation electrodes may be axially spaced from 0.1 mm to 5 mm apart, such as from 0.1 mm to 3 mm apart, optionally from 0.5 mm to 1 mm apart. Distal and proximal ablation elements in this aspect may be any of the distal and proximal ablation elements herein, such as coiled elements. In this aspect a cross-sectional outer profile of a distal ablation electrode may be different than a cross-sectional outer profile of a proximal ablation electrode. Distal and proximal ablation electrodes may be made from a superelastic material such as nitinol. Distal and proximal ablation electrodes may be sufficiently flexible to allow the distal region to be advanced from an azygos vein into one of a T9, T10, or T11 intercostal vein.

In this aspect, the ablation element may not be configured to deploy to a deployed configuration.

In this aspect, the ablation element may have an operational configuration that is the same or substantially the same as a delivery configuration.

In this aspect, the distal section may have a linear at-rest configuration.

In this aspect, the ablation element may have an outer diameter in an operational state that is the same or substantially the same as an outer diameter in a delivery state.

In this aspect the catheter may further comprise one or more temperature sensors carried by the shaft. A temperature sensor may be disposed at a distal end of the ablation element. A temperature sensor may be disposed at a proximal end of the ablation element. The catheter may further comprise a second temperature sensor, the temperature sensor may be disposed at or near a distal end of the ablation element, the second temperature sensor may be disposed at or near a proximal end of the ablation element.

In this aspect the catheter may comprise one or more irrigation ports in fluid communication with an irrigation lumen that is connectable to a fluid source at a proximal region of the ablation catheter, including any of the one more irrigation ports herein. One of the one or more irrigation ports may be axially in between the distal and proximal ablation electrodes. Optionally none of the one or more irrigation ports may be disposed radially under an ablation element structure. The one or more irrigation ports may be disposed between windings of the distal and proximal ablation electrodes, and wherein none of the one or more irrigation ports may be disposed radially under an ablation element structure. In a side view, an irrigation port may be disposed between every adjacent pair of ablation element helical sections.

In this aspect the ablation element may comprise first and second ablation elements, each of which may be electrically configured to be independently energized in monopolar mode.

In this aspect the ablation element may comprise first and second ablation elements that are electrically configured to be energized in bipolar mode.

In this aspect the distal section may be no more than 7 cm from a distal tip of the ablation catheter.

In this aspect the ablation element may be adapted to create an ablation having a length in a range of 10 to 25 mm, such as 15 mm to 20 mm.

In this aspect the distal section may be adapted for flexibly traversing a bend from an azygos vein to a T9, T10, or T11 intercostal vein.

In this aspect the catheter may further comprise a guidewire lumen within the elongate shaft and having a distal port at a distal tip of the catheter.

In this aspect the ablation element may comprise one or more of an RF ablation electrode, a coiled wire electrode, a laser cut RF electrode, a RF electrode printed with conductive ink, a RF electrode on an expandable balloon (e.g., conductive ink, flexible circuits,), a conductive membrane RF electrode, a RF electrodes on an expandable cage or mesh, an ultrasound ablation transducer, an electroporation electrodes, an cryoablation element, or a virtual RF electrode.

In this aspect the ablation element may be adapted and configured to deliver ablation energy circumferentially to create a circumferential lesion.

One aspect of the disclosure is an ablation catheter for ablating a greater splanchnic nerve, comprising: an elongate shaft, an electrically conductive flexible ablation element (optionally distal and proximal coiled elements) carried by a distal section or region of the elongate shaft, and a plurality of irrigation ports in the distal section of the elongate shaft. The electrically conductive flexible ablation element may have an axial length (e.g., from a proximal end to a distal end) from 5 mm-25 mm.

In this aspect, an elongate shaft may have a length such that at least a portion of a distal section of the elongate shaft can be positioned in a T9, T10, or T11 intercostal vein. In this aspect, an electrically conductive flexible ablation element may comprise distal and proximal electrically conductive flexible ablation elements (optionally coiled) carried by the elongate shaft distal section.

In this aspect, a first subset of the plurality of irrigation ports may be disposed between windings of an electrically conductive flexible ablation element, such as an RF electrode, which may be a first electrode or a second electrode. A subset of the plurality of irrigation ports may be distal to the electrically conductive flexible ablation element. A subset of the plurality of irrigation ports may be disposed axially between distal and proximal ablation elements.

In this aspect, the elongate shaft may be void of or free of irrigation ports between at least one winding at distal and/or proximal ends of an electrically conductive flexible ablation, optionally void of or free of irrigation ports between at least one winding at distal and/or proximal ends of first and second coiled electrodes.

In this aspect, an electrically conductive flexible ablation element may include distal and proximal coiled electrodes. Distal and proximal ends of each of distal and proximal electrodes may comprise a coil with a varying pitch.

In this aspect, distal irrigation ports may be within 2 mm of a distal end of an electrically conductive flexible ablation, which may be a distal end of a distal ablation element. In some instances, the number of distal irrigation ports may be from two to four, or more. Distal irrigation ports herein may be axially aligned, such as shown in exemplary FIG. 8E.

In this aspect, distal and proximal electrically conductive flexible ablation elements may be are axially spaced no more than 2 mm apart, optionally no more than 1.5 mm apart.

In this aspect, central irrigation ports between distal and proximal ablation may include from two to four ports, or more, and may be axially aligned, such as shown in exemplary FIG. 8E.

In this aspect, the plurality of irrigation ports may have a combined and total area in a range of 1.51e-4 to 1.08e-3 in$^2$.

In this aspect, a diameter of all of the plurality of irrigation ports may be in a range of 0.002" to 0.009".

In this aspect, the quantity of the plurality of irrigation ports may be in a range of 17 to 344.

In this aspect, the plurality of irrigation ports may have a size and quantity such that a Weber number is in a range of 0.4-53 when irrigation fluid is delivered from the plurality of irrigation ports, optionally at a rate of 15 ml/min to 50 ml/min, and optionally with saline.

In this aspect, the distal section may have a distal length from 60 mm to 70 mm and may be sufficiently flexible to be advanced from an azygous vein into an intercostal vein. In this aspect, the elongate shaft may also have a central transition section proximal to the distal section, the central section optionally having a central length from 15 mm to 25 mm and optionally having a central stiffness and that is greater than a distal stiffness of the distal section. In this aspect, the elongate shaft may have a proximal section proximal to a central section, the proximal section optionally having a length that is greater than the distal length and greater than the central length, the proximal section optionally having a proximal stiffness that is greater than the central stiffness and greater than the distal stiffness. A central section in this aspect may be immediately axially adjacent and proximal to the distal section. A proximal section in this aspect may be immediately axially adjacent and proximal to a central section. In this aspect, a distal section may have a durometer from 50 D to 60 D, optionally 55 D. In this aspect, a central section may have a durometer from 60 D to 70 D, optionally from 60 D to 65 D. In this aspect, a proximal section may have a distal end not closer than 50 mm from a distal end of the catheter. A proximal section in this aspect may have a distal end that is from 75 mm to 100 mm away from a distal end of the catheter, and may optionally extend to a proximal end of the elongate shaft. In this aspect, a proximal section may include a braided reinforcing structure therein, and distal and central sections may optionally be free of a braided reinforcing structure. In this aspect, a proximal section may as a durometer from 70 D to 80 D, optionally from 70 D to 75 D.

In this aspect, a distal section of an elongate shaft may have a linear or straight configuration (such as shown in exemplary FIG. 8E) and may have an outer diameter from 1.5 mm to 3 mm when the distal section is outside of a sheath.

Any first and second ablation elements in this aspect may have coiled configurations, such as those shown in exemplary FIG. 8E.

In this aspect, the distal section may include a plurality of irrigation ports having a helical configuration. There may be multiple sets of ports, each of which has a separate helical configuration, such as shown in the multiple sets of irrigation ports shown in exemplary FIG. 8E. The multiple sets may be between distal and proximal end of any particular electrode, such as shown in exemplary FIG. 8E.

In this aspect, a distal section of the shaft may have a distal diameter, a central section may have a central diameter, and a proximal section may have a proximal diameter, the distal diameter optionally less than the central diameter and the central diameter optionally less than the proximal diameter. In this aspect, a distal diameter may be from 1.5 mm to 2.5 mm, optionally 2 mm. A central diameter may be from 2.0 mm to 3.0 mm, optionally 2.5 mm. A proximal diameter may be from 2.5 mm to 3.5 mm, optionally 3 mm.

One aspect of this disclosure is related to tracking or calculating how much volume of liquid has been delivered through a catheter and into a patient. This aspect may include a computer executable method that is adapted to calculate an accumulated volume of liquid that has been delivered through a catheter to a patient while excluding (or not including) from the accumulated volume liquid that may be delivered through the catheter but not into the patient's vasculature. The method may include initiating a method that calculates an accumulated volume of liquid that has been delivered from outside of a catheter, through the catheter, and into a patient, and in response to an exclusion event that is indicative of the catheter not being inside the patient, stopping the method that calculates the accumulated volume of liquid to avoid including a volume of fluid that is not delivered into the patient's vasculature from being included in the accumulated volume.

In this aspect, an exclusion event may comprise an operator action that causes the method to be stopped.

In this aspect, an exclusion event may comprise an automatic action that causes the method to be stopped.

In this aspect, a method that calculates an accumulated volume of liquid may comprise calculating an accumulated volume by multiplying a flow rate by an elapsed time. A flow rate may be determined by multiplying a volume per pulse by pulses per second.

This aspect may also include calculating or tracking an accumulated volume of the liquid that is not delivered into the patient's vasculature when it is determined that the catheter is not in the patient's vasculature.

In this aspect, an exclusion event may optionally comprise an impedance measurement or calculation that is outside of a range, or higher than a high threshold, for example. An exclusion event may comprise an impedance measurement or calculation that is above 700 to 900 Ohms in a monopolar mode, for example. An exclusion event may comprise an impedance measurement or calculation that is above 300 to 600 Ohms in bipolar mode, for example. An exclusion event may comprise an impedance measurement or calculation that is outside of 60 to 80 Ohms, for example.

In this aspect, an exclusion event may comprise an impedance measurement or calculation that determines if the catheter is out of the body. Initially, the catheter is out of the body and when a low threshold is crossed the algorithm may be adapted to determine that the catheter has passed into the body, wherein pumped saline is included in the accumulation calculation. When the catheter is determined to be in the body and a high threshold is passed, the algorithm may be adapted to determine that the catheter has passed from in the body to out of the body, wherein pumped saline is excluded. An exclusion event may comprise a determination that the catheter is out of the body. If the catheter is out of the body an exclusion event may comprise an impedance measurement that is higher than a low threshold. If the catheter is in the body an exclusion event may comprise an impedance measurement that is higher than a high threshold.

In this aspect, a method that calculates an accumulated volume of liquid may continue uninterrupted until an exclusion event occurs.

In this aspect, the liquid may be saline.

Any method in this aspect may store on an external energy delivery console of an ablation system, which may be any of the external systems described herein that are adapted to be placed in operable communication with any of the ablation catheters herein.

One aspect of the disclosure is related to methods of delivering ablative energy to tissue, such as tissue surrounding an intercostal vein. The methods may include delivering waveforms from any of the external systems herein to any of the suitable ablation catheters herein, and may include the external system receiving information from any of the suitable ablation catheters herein.

In this aspect, a method may include delivering from a power module (e.g. part of an external system) to a first electrode a first waveform of ablative RF energy with an initial power from 15-50, delivering from the power module to a second electrode a second waveform of ablative RF energy with an initial power from 15-50 W, receiving information indicative of at least one of sensed temperature or measured impedance, determining if at least one of the sensed temperature or the measured impedance is at or above a limit, if at least one of the sensed temperature or the measured impedance is at or above a threshold limit, decreasing the power of at least one of the first waveform and the second waveform.

The methods in this aspect may be used with any suitable catheter herein. For example, a first waveform may be delivered to a first electrode (optionally coiled), and a second waveform may be delivered to a second electrode (optionally coiled).

In this aspect, if at least one of the sensed temperature or the measured impedance is at or above a threshold limit, and a minimum therapy time has not yet passed, the reducing step may comprise reducing the power of at least one of the first waveform and second waveform to a secondary power less than the initial power. In this aspect, a secondary power may be from 5-10 W less than any initial power.

In this aspect, if at least one of the sensed temperature or the measured impedance is at or above a threshold limit, and a minimum therapy time has passed, the reducing step may comprise reducing the power of at least one of the first waveform and second waveform to a secondary power that is from 0 W to 1 W.

In this aspect, the first and second waveforms may be multiplexed.

In this aspect, the first and second waveforms may be asynchronous.

In this aspect, delivering from a power module to a first electrode may comprise delivering from a power module to a first electrode a first waveform of ablative RF energy with an initial power of 25 W. Delivering from a power module to a second electrode may comprise delivering from a power module to the second electrode a second waveform of ablative RF energy with an initial power of 25 W.

In this aspect, the first and second waveforms may be alternating waveforms that alternate between an ablative power amplitude and a non-ablative power amplitude. A non-ablative power amplitude in this aspect may be in a range of 0 W to 1 W.

In this aspect, the determining step may comprise determining if the sensed temperature is at or above 40° C. to 95° C., optionally at or above 90° C.

In this aspect, the receiving step may comprise receiving information from a temperature sensor associated with a first electrode, such as any of the coiled electrodes herein. In this aspect, the receiving step may comprise receiving information from a second temperature sensor associated with a second electrode, such as any of the coiled electrodes herein.

In this aspect, the determining step may comprise determining if a measured impedance is at or above 200 to 500 ohms, optionally at or above 500 ohms.

In this aspect, reducing the power of at least one of the first waveform and the second waveform may comprise reducing the power of at least one of the first waveform and the second waveform to a power from 10 W to 30 W, optionally 20 W.

In this aspect, reducing the power of at least one of the first waveform and the second waveform may comprise reducing the power of at least one of the first waveform and the second waveform by a power decrement from 1 W to 30 W, optionally from 5-10 W.

In this aspect, at least one of the first and second waveforms may have a pulse width in a range of 0.5 seconds to 4 seconds.

In this aspect, the power of the first waveform may be decreased if a sensed temperature corresponding to a first electrode is at or above the limit, and wherein the power of the second waveform may be decreased if the sensed temperature corresponding to a second electrode is at or above the limit.

In this aspect, the delivering step may occur for at least 60 seconds.

In this aspect, the delivering step may occur with a default setting to occur from 30 seconds to 180 seconds.

Any method in this aspect may further comprise delivering irrigation fluid to an ablation catheter at a flow rate in a range of 10 to 30 ml/min. Delivering irrigation fluid to an ablation catheter may include delivering fluid to, though, and out of any of the ablation catheters herein, including any and all of the description of the irrigation ports from which irrigation fluid may be delivered into the subject.

One aspect of the disclosure is related to external devices (which may include one or more separate components) that are adapted for use with any of the ablation catheters herein. External devices as used herein generally refers to one or more components of a system that remain outside of a subject, such as a power module, energy generator, etc. The external devices herein may be adapted to be coupled to or with any of the ablation catheters herein to create operable communication therebetween. External devices herein may be referred to as external systems, and it is understood that this refers to the external nature of the one or more components. An ablation catheter and one or more external components may together be referred to herein as a system. Any feature of this aspect may be incorporated with the previous aspect described herein that is related to delivering ablative energy, and vice versa. For example, any of the methods set forth in the previous aspect may be stored in one or more memories on any of the external devices in this aspect of the disclosure, and may be used with any of the ablation catheters in this aspect.

This aspect may include an external device or system that is adapted for use with an ablation catheter that includes first and second ablation electrodes. The external device may comprise a power output module that adapted to deliver a first waveform of ablative RF energy with an initial power from 15-50 W and a second waveform of ablative RF energy with an initial power from 15-50 W. The external device may also include a module adapted to receive information indicative of at least one of sensed temperature or measured impedance and determine if at least one of the sensed temperature or the measured impedance is at or above a limit, and if at least one of the sensed temperature or the measured impedance is at or above a threshold limit, causing the power output module to decrease the power of at least one of the first waveform and the second waveform.

In this aspect, the module may comprise at least one of a temperature limit module or an impedance limit module.

One aspect of this disclosure is related to delivering irrigation fluid to an ablation catheter. This aspect may include a method of delivering ablation energy and irrigation fluid to a catheter for ablating a greater splanchnic nerve, wherein the method includes positioning an ablation catheter in an intercostal vein, delivering ablative energy to one or more ablation elements carried by a distal region of an ablation catheter, ablating a greater splanchnic nerve outside of the intercostal vein, and delivering irrigation fluid out of a plurality of irrigation ports in the distal region or section of the ablation catheter at a rate from 15 ml/min-50 ml/min.

Any feature of this aspect of the disclosure may be included or incorporated with any step or steps of any other aspect, including aspects related to delivering ablative energy using any of the ablation catheters herein.

In this aspect, delivering the irrigation fluid may comprise delivering irrigation fluid out of a plurality of irrigation ports in the distal region of the ablation catheter at a rate of 30 ml/min.

In this aspect, delivering the irrigation fluid may comprise delivering the irrigation fluid out of 17 to 344 irrigation ports in the distal region or section of the catheter.

In this aspect, delivering the irrigation fluid comprises delivering the irrigation fluid out of a plurality of distal irrigation ports, the distal irrigation ports being disposed distal to the one or more ablation elements.

In this aspect, delivering the irrigation fluid may comprise delivering the irrigation fluid out of a plurality of central irrigation ports, the central irrigation ports disposed between a proximal ablation element and a distal ablation element.

In this aspect, delivering the irrigation fluid may comprise avoiding delivering the irrigation fluid out of any part of the distal region or section of the shaft that is proximal to the one or more ablation elements, optionally due to the absence of any irrigation ports proximal to the one or more ablation elements.

In this aspect, delivering ablative energy may comprises delivering energy at a power from 15 W-50 W, optionally at 35 W.

In this aspect, delivering the irrigation fluid may comprise delivering irrigation fluid distal to the one or more ablation elements and not delivering irrigation fluid proximal to the one or more ablation elements.

In this aspect, delivering the irrigation fluid may comprise delivering irrigation fluid out of a plurality of irrigation ports, wherein the plurality of irrigation ports optionally having a combined area in a range of 1.51e-4 to 1.08e-3 $in^2$.

In this aspect, a diameter of the plurality of irrigation ports may be in a range of 0.002" to 0.009".

In this aspect, delivering the irrigation fluid out of the plurality of irrigation ports at a rate from 15 ml/min-50 ml/min may create a Weber number in a range of 0.4-53.

In this aspect, delivering the ablative energy may comprise delivering the ablation energy to first and second coiled ablation elements that are axially spaced apart on the shaft.

In this aspect, delivering irrigation fluid may comprise delivering the irrigation fluid out of at least some of the plurality of ports that are disposed between windings of first and second coiled ablation elements.

BRIEF DESCRIPTION OF THE DRAWINGS

The drawings included herewith are for illustrating various examples of articles, methods, and apparatuses of the present specification and are not intended to limit the scope of what is taught in any way. In the drawings:

FIG. 8A is a schematic illustration of an ablation catheter with two coiled RF electrodes.

FIG. 8B is a schematic illustration of an ablation catheter with two coiled RF electrodes and a distal deployable element.

FIG. 11 is a schematic illustration of an ablation catheter with an RF electrode comprising expandable wire struts.

FIG. 12 is a schematic illustration of an ablation catheter with an RF electrode comprising an expandable balloon with an RF electrode on its surface.

DETAILED DESCRIPTION

The disclosure herein is generally related to methods of treating at least one of heart failure and hypertension by increasing splanchnic capacitance. Some approaches include systems, devices, and methods for transvascular (e.g., transvenous) ablation of target tissue to increase splanchnic venous capacitance or venous compliance. The devices and methods may, in some examples, be used for ablating a splanchnic nerve to increase splanchnic capacitance. For example, the devices disclosed herein may be advanced endovascularly to a target vessel or plurality of vessels in the region of a thoracic splanchnic nerve ("TSN"), such as a preganglionic greater splanchnic nerve ("GSN"), lesser splanchnic nerve, or least splanchnic nerve or one of their roots (a TSN nerve root). The target vessel may be, for example, an intercostal vein or an azygos vein (or both) or a vein of the azygos vein system, preferably, one or more of the lowest (i.e., most caudal) three intercostal veins (which may be T9, T10, or T11).

Figure 1:
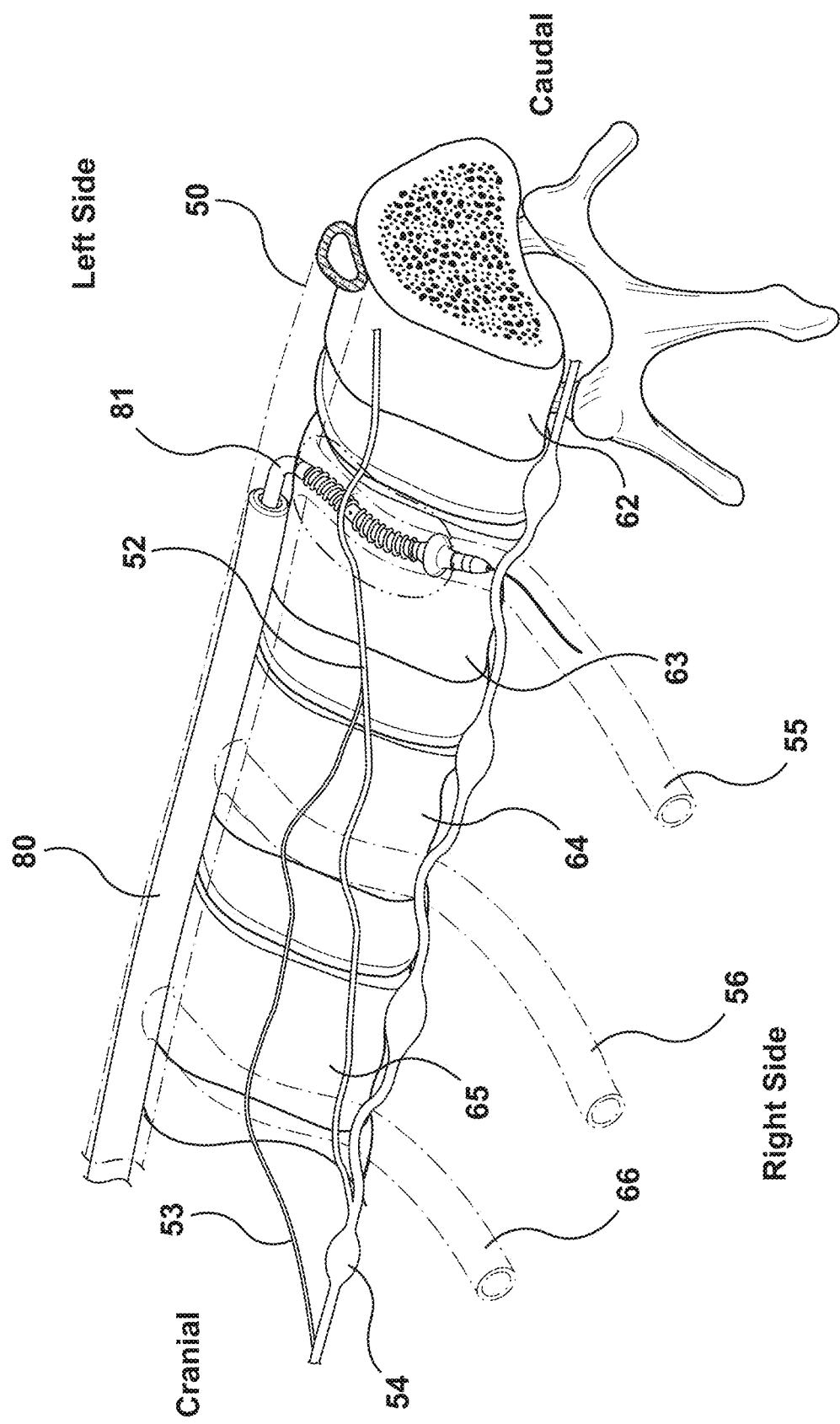
FIG. 1 is an isometric view schematic illustration of an ablation catheter positioned in an intercostal vein for ablation of a thoracic splanchnic nerve.
Figure 2:
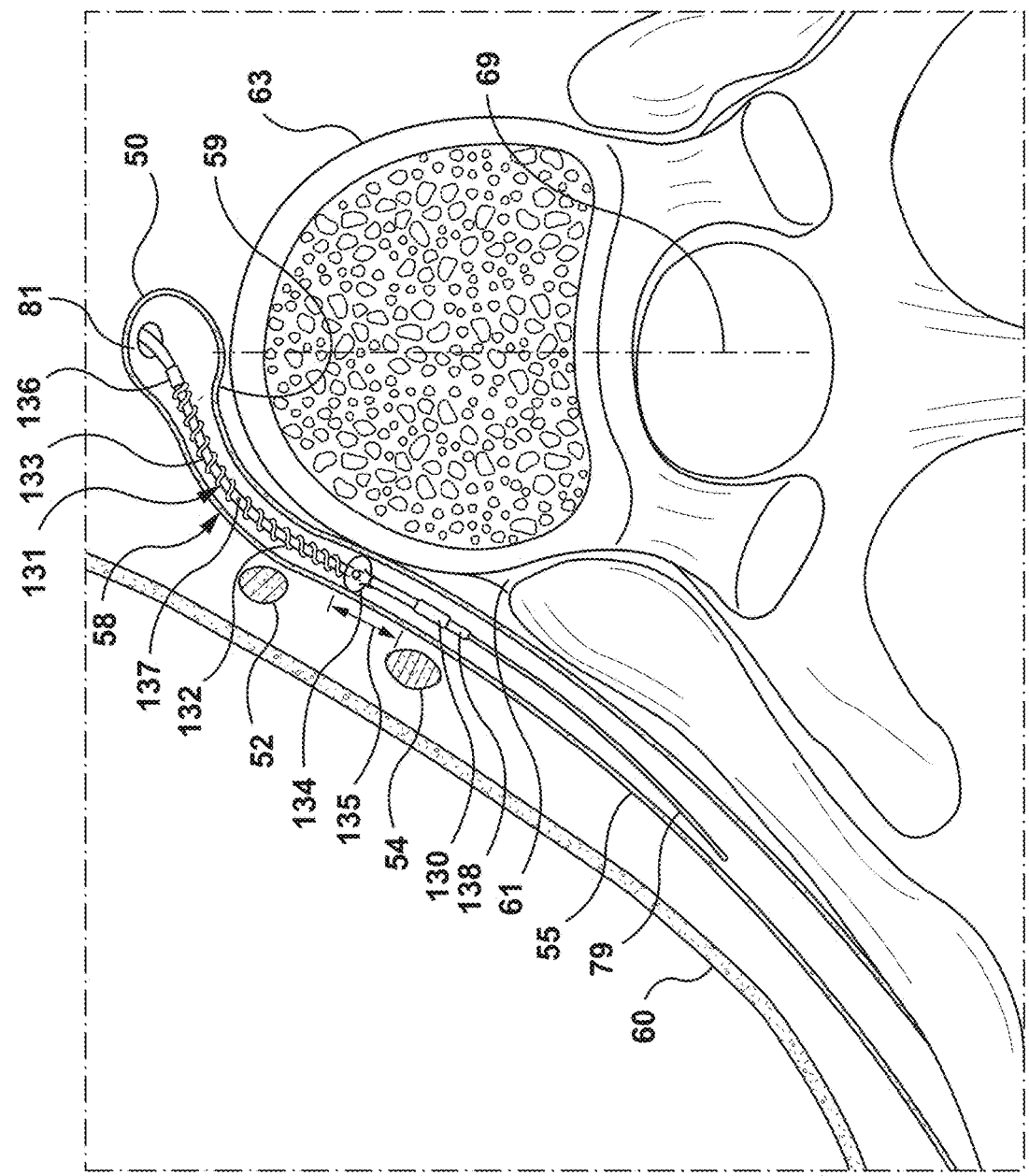
FIG. 2 is a transverse view schematic illustration of an ablation catheter positioned in an intercostal vein and a centered azygos vein.
Figure 3:
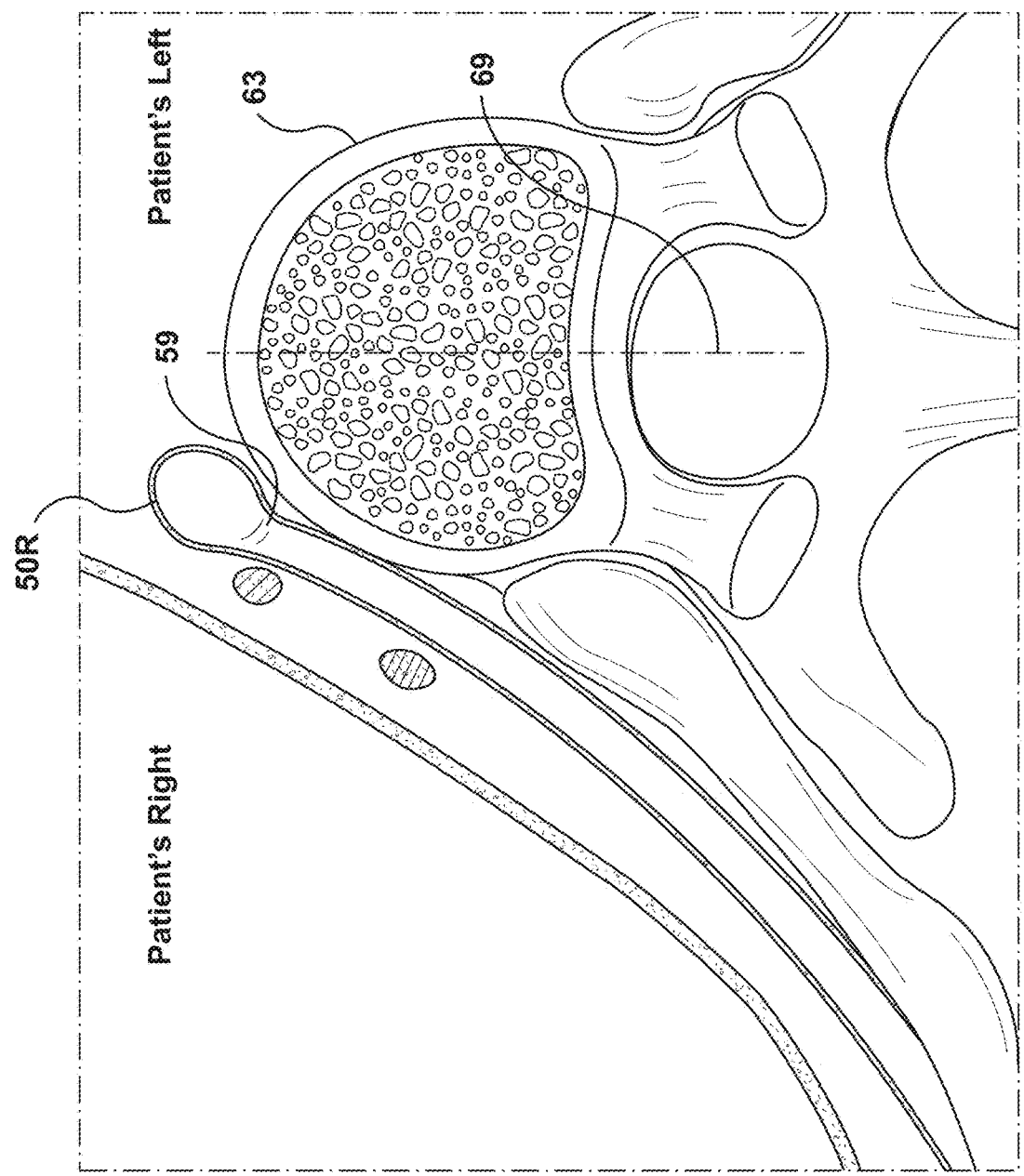
FIG. 3 is a transverse view schematic illustration of anatomy showing a right-biased azygos vein.
Figure 4:
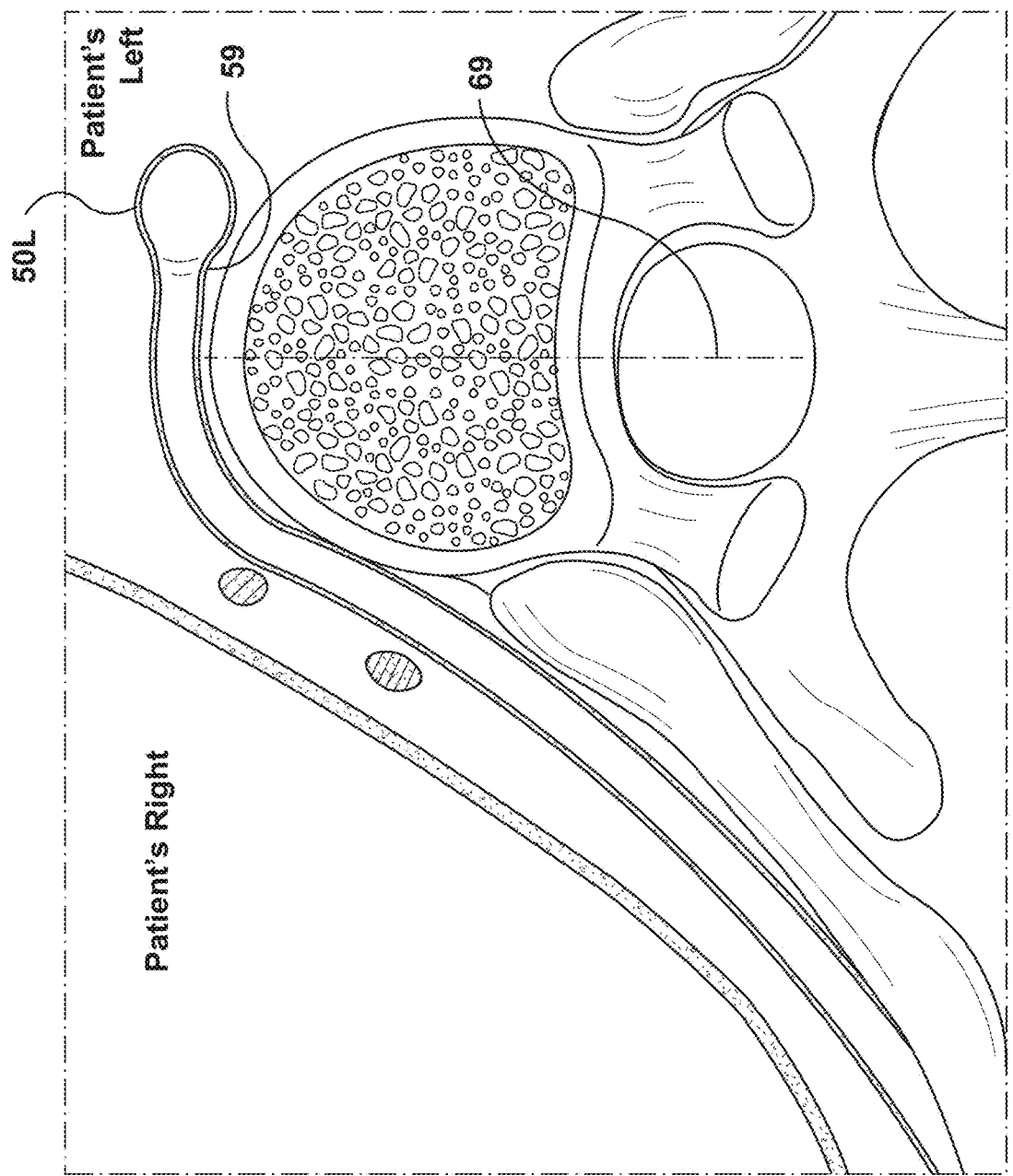
FIG. 4 is a transverse view schematic illustration of anatomy showing a left-biased azygos vein.
Figure 5:
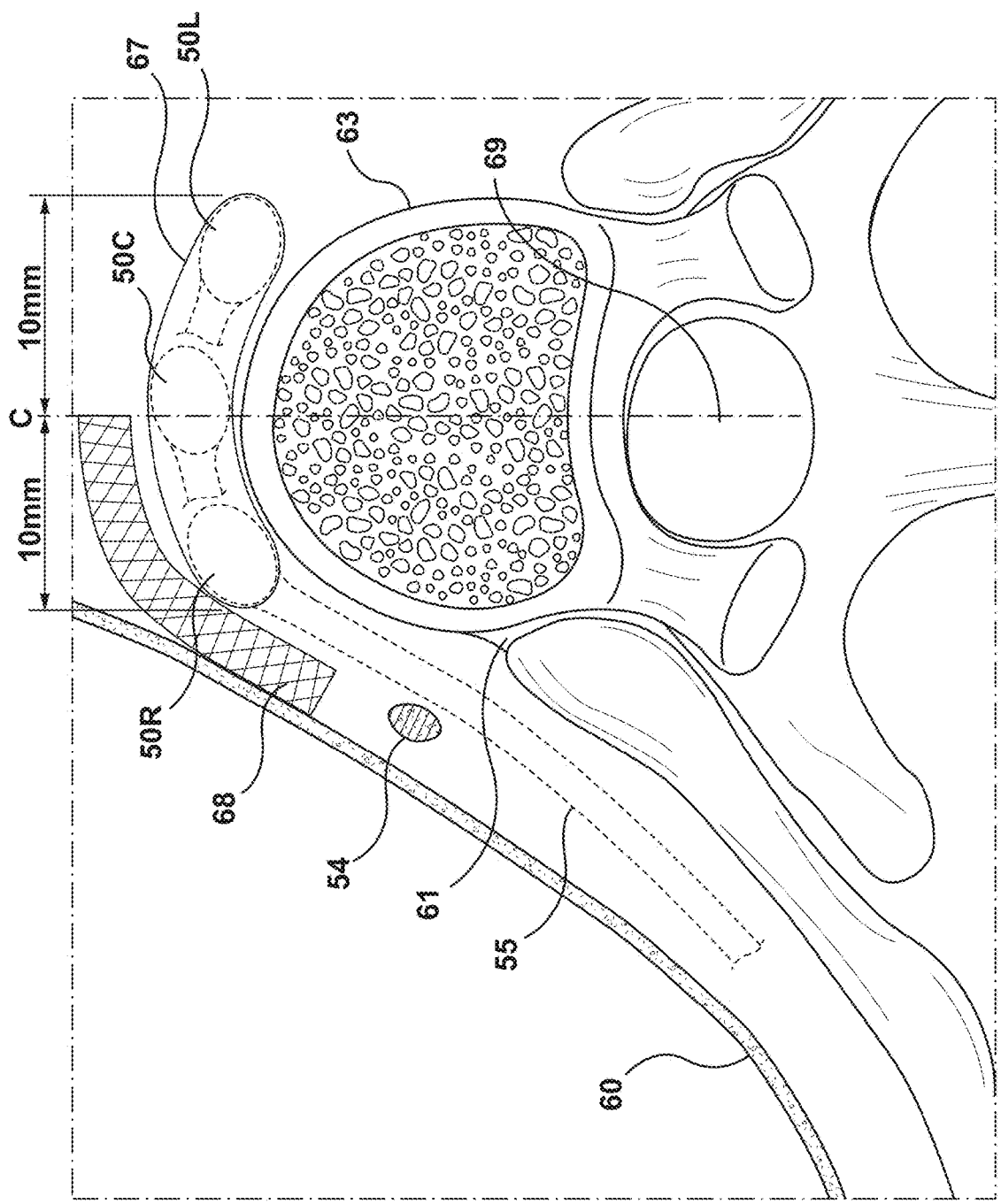
FIG. 5 is a transverse view schematic illustration of anatomy showing a range of position of azygos veins and a range of position of a right GSN.

FIG. 1 shows a patient's thoracic spine, including T12 (62), T11 (63), T10 (64), and T9 (65) vertebrae, intervertebral discs, a sympathetic trunk 54, an azygos vein 50, a right T11 intercostal vein 55, a right T10 intercostal vein 56, a right T9 intercostal vein 66, GSN roots 53, and a fully-formed GSN 52. The lesser and least splanchnic nerves and their roots are omitted for simplicity. A primary objective of the proposed procedure is to ablate the GSN or its roots as will be discussed in detail herein. It is noted that ablation of the lesser or least splanchnic nerves or their roots may also have therapeutic effects and may be a procedural objective. A delivery sheath 80 is shown positioned in the azygos vein and an ablation catheter 81 is shown delivered through the sheath and passing from the azygos vein into the T11 intercostal vein. The sympathetic trunk runs substantially parallel to the spine, consistently passing close to each costovertebral joint 61 (see FIG. 2). On the right side of the body the GSN roots branch from the sympathetic trunk, typically cranial to the T9 vertebra, and converge to form the GSN, which travels at an angle from the sympathetic trunk toward the anterior-center of the spine and is positioned anterior to the intercostal veins between the intercostal veins and parietal pleura 60 (see FIG. 2). The azygos vein 50 travels along the anterior of the spine and may be somewhat straight and parallel to the axis of the spine as shown in FIG. 1. However, the precise position of the azygos vein relative to the spine is variable from patient to patient and at different vertebral levels. At the T9, T10, and T11 vertebral levels the azygos vein 50 may be centered with respect to the midline of the vertebra 69 as shown in FIG. 2, may be a right-biased azygos vein 50R with respect to the midline of the vertebra 69 as shown in FIG. 3, or be a left-biased azygos vein 50L with respect to the midline of the vertebra 69 as shown in FIG. 4. Cadaver studies conducted by the authors indicate that the range of azygos position relative to the center of the spine at the T9, T10, and T11 levels is within 10 mm to the left or right of center for a large majority of people. FIG. 5 shows a left-biased azygos vein 50L, a right-biased azygos vein 50R, and a centered azygos vein 50C along with the range 67 of the azygos vein relative to the center of the spine 69. Furthermore, the precise position of the right GSN from patient to patient is somewhat variable including where it originates from the sympathetic trunk, the angle at which it travels, and its destination relative to the spine. Thus, the position of the GSN relative to the vertebra at T9, T10 and T11 can vary. Cadaver studies conducted by the authors indicate that the range of right side GSN position relative to the center of the vertebra at the T9, T10 and T11 levels is from 0 mm to 25 mm to the right of center 69 as shown by the range box 68 in FIG. 5.

An endovascular approach to transvascularly ablate a TSN, particularly a GSN may involve one or more of the following steps: accessing venous vasculature at the patient's jugular vein or femoral vein with an access introducer sheath (e.g. 12 F); delivering a delivery sheath (e.g., 9 F sheath) to an azygos vein (e.g., to one or two thoracic levels above the target intercostal vein); optionally, delivering contrast agent through the sheath to show location of veins on fluoroscopy; optionally, delivering a guidewire (e.g., 0.014" guidewire) through the delivery sheath and into a targeted T9, T10, or T11 intercostal vein; and delivering an ablation catheter through the delivery sheath to the azygos vein, optionally over the guidewire, positioning an ablation element in an intercostal vein, azygos vein or both; and aligning a radiopaque marker on the ablation catheter with an anatomical landmark (or positioning it relative thereto) to position an ablation element in a region that maximizes efficacy of ablating a target TSN/GSN while minimizing risk of injuring one or more non-target structures.

Some important anatomical structures in the vicinity of this region that should not be injured include the sympathetic trunk 54, vagus nerve, thoracic duct, and esophagus. Therefore, to ensure safety an ablation zone should be contained within a safe region that does not injure such structures. Due to the variability of position of the azygos vein and GSN relative to the T9, T10 and T11 vertebrae, the relative position of the GSN with respect to the intercostal vein or azygos vein in which an ablation element is positioned is also variable.

Bones, blood vessels if injected with radiopaque contrast medium, and medical devices if made from radiopaque material, are visible on fluoroscopy but nerves are not. An ablation device designed for transvascular (e.g., transvenous) ablation of a TSN (e.g., GSN) from an intercostal vein, azygos vein, or both along with procedural steps may be provided to ensure efficacious ablation of the TSN (e.g., GSN) while ensuring safety. The procedural steps may include fluoroscopic imaging to position the ablation element(s) of the ablation catheter with respect to boney or vascular structures.

Figure 7:
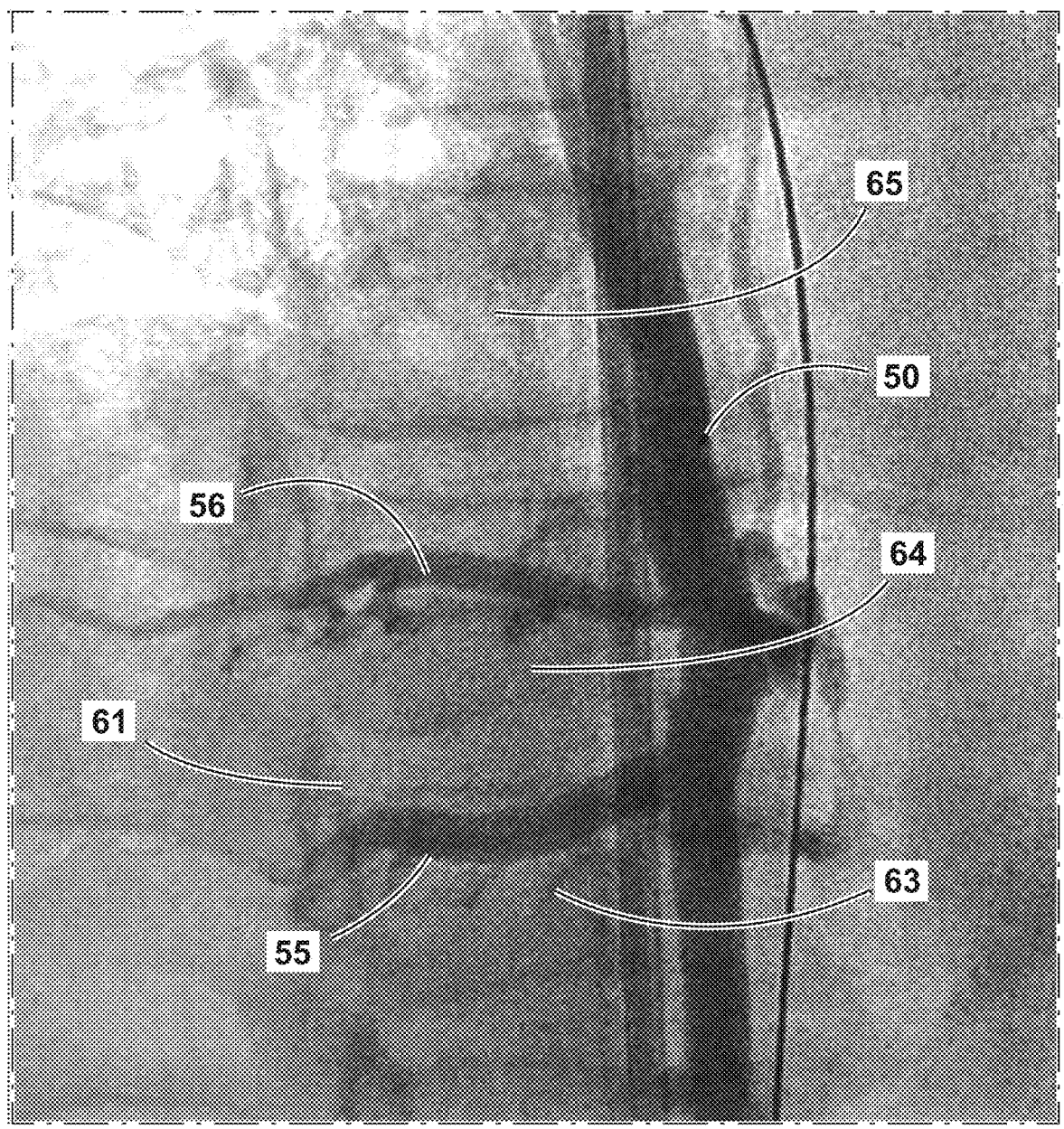
FIG. 7 is an RAO30 fluoroscopic image of a patient's T8 to T12 thoracic region.

In a first embodiment of a method of ablating a right GSN an ablation catheter having a proximal radiopaque marker 136, a distal radiopaque marker 130, an ablation element 131 or plurality of ablation elements 132, 133, and an optional gap 135 between the ablation element and the distal radiopaque marker is advanced from an azygos vein 50 into an intercostal vein 55 at one of the lower three thoracic levels (e.g., T9, T10, T11). The C-Arm is placed in Anterior-Posterior (AP) orientation. The proximal radiopaque marker 136 is aligned with the midline of the vertebra 69, which is possible if the azygos vein 50 is centered or left-biased. If the azygos vein 50 is left-biased the proximal radiopaque marker will need to be advanced into the intercostal vein to align it with the midline of the vertebra 69. If the azygos vein is right-biased the proximal radiopaque marker 136 will not be able to be placed at the midline of the vertebra 69. In this case the proximal radiopaque marker 136 may be placed at the ostium of the intercostal vein, which will be to the right of midline 69. Optionally, the position of a distal radiopaque marker 130 relative to the costovertebral joint may be assessed (e.g., with the C-Arm in a RAO orientation) to ensure the sympathetic trunk is not at risk of injury, for example with patients who are very small and have an extreme right-biased azygos vein. The C-Arm may be obliquely angled to the right (RAO orientation) to maximize the 2D projection of the section of intercostal vein between the costovertebral joint 61 and anterior midline of the vertebra 69 (FIG. 7). For example, the C-arm may be positioned with a Right Anterior Oblique (RAO) angle in a range of 20° to 70° from AP (e.g., in a range of 30° to 60°, in a range of 35° to 55°, about 30°, at an angle that maximizes projected distance between the proximal and distal RO markers). With this view the user may check to make sure the distal radiopaque marker is not too close to the costovertebral joint 61. For example, if the distal radiopaque marker is positioned directly distal to the ablation element a distance of at least 3 mm (e.g., at least 5 mm) may be chosen to ensure the sympathetic trunk is not injured. In another example, if the distal radiopaque marker is positioned distal to the ablation element with a known space between them the distal radiopaque marker may be aligned with the costovertebral joint or proximal to it to ensure safety of the sympathetic joint. If the distal radiopaque marker is too close to or beyond the costovertebral joint the catheter may be pulled back until an acceptable distance between the distal radiopaque marker and the costovertebral joint is seen, which may place the proximal radiopaque marker in the azygos vein especially if the azygos vein is right biased. If the ablation element is comprised of a plurality of ablation elements (e.g., two) an ablation may first be performed from the more proximal ablation element prior to pulling the catheter back to appropriately place the distal radiopaque marker relative to the costovertebral joint. Then a subsequent ablation may be made from the more distal ablation element.

In a second embodiment of a method of ablating a right GSN an ablation catheter having a proximal radiopaque marker 136, a distal radiopaque marker 130, an ablation element 131 or plurality of ablation elements 132, 133, and an optional gap 135 between the ablation element and the distal radiopaque marker is advanced from an azygos vein 50 into an intercostal vein 55 at one of the lower three thoracic levels (e.g., T9, T10, T11). The C-Arm is placed in Anterior-Posterior (AP) orientation. The proximal radiopaque marker 136 is aligned with the intercostal vein ostium 59. The ostium can be found for example by injecting contrast agent and viewing the vasculature on fluoroscopy or if a guidewire was previously positioned in a target intercostal vein a bend in the guidewire or ablation catheter may indicate the location of the ostium. If the azygos vein is left-biased the catheter is advanced distal to the ostium to align the proximal radiopaque marker 136 with the midline of the vertebra 69. In this placement strategy the proximal radiopaque marker 136 will be aligned with the midline of the vertebra 69 if the azygos vein is left-biased or centered, and to the right of the midline of the vertebra if the azygos vein is right-biased. Concurrently, the proximal radiopaque marker 136 will be aligned with the ostium if the azygos vein is right-biased or centered, and at the midline of the vertebra 69 if the azygos vein is left-biased. Optionally, the position of a distal radiopaque marker 130 relative to the costovertebral joint may be assessed (e.g., with the C-Arm in a RAO orientation) to ensure the sympathetic trunk is not at risk of injury, for example with patients who are very small and have an extreme right-biased azygos vein. The C-Arm may be obliquely angled to the right (RAO orientation) to maximize the 2D projection of the section of intercostal vein between the costovertebral joint 61 and anterior midline of the vertebra 69 (FIG. 7). For example, the C-arm may be positioned with a Right Anterior Oblique (RAO) angle in a range of 20° to 70° from AP (e.g., in a range of 30° to 60°, in a range of 35° to 55°, about 30°, at an angle that maximizes projected distance between the proximal and distal RO markers). With this view the user may check to make sure the distal radiopaque marker is not too close to the costovertebral joint 61. For example, if the distal radiopaque marker is positioned directly distal to the ablation element a distance of at least 3 mm (e.g., at least 5 mm) may be chosen to ensure the sympathetic trunk is not injured. In another example, if the distal radiopaque marker is positioned distal to the ablation element with a known space between them the distal radiopaque marker may be aligned with the costovertebral joint or proximal to it to ensure safety of the sympathetic joint. If the distal radiopaque marker is too close to or beyond the costovertebral joint the catheter may be pulled back until an acceptable distance between the distal radiopaque marker and the costovertebral joint is seen, which may place the proximal radiopaque marker in the azygos vein especially if the azygos vein is right biased.

Figure 6:
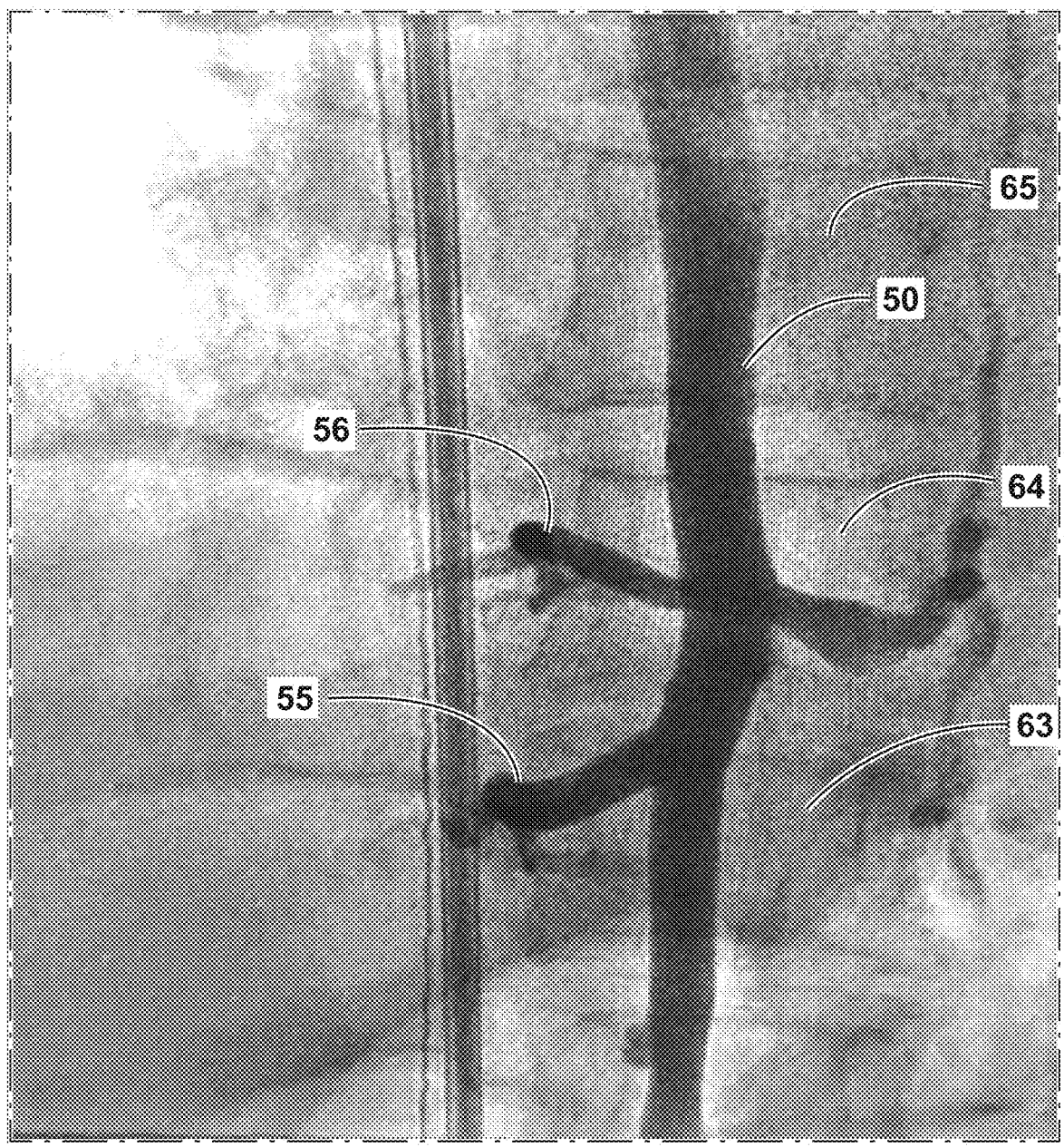
FIG. 6 is an AP fluoroscopic image of a patient's T8 to T12 thoracic region.

In a third embodiment of a method of ablating a right GSN an ablation catheter having a distal radiopaque marker 130, an ablation element 131 or plurality of ablation elements 132, 133, and a gap 135 between the ablation element and the distal radiopaque marker is advanced from an azygos vein 50 into an intercostal vein 55 at one of the lower three thoracic levels (e.g., T9, T10, T11). The C-Arm is obliquely angled to the right to maximize the 2D projection of the section of intercostal vein between the costovertebral joint 61 and anterior midline of the vertebra 69 (FIG. 2). For example, the C-arm may be positioned with a Right Anterior Oblique (RAO) angle in a range of 20° to 70° from AP (e.g., in a range of 30° to 60°, in a range of 35° to 55°, about 30°, at an angle that maximizes projected distance between the proximal and distal RO markers). A fluoroscopy image in an anterior-posterior (AP) view is shown in FIG. 6. In comparison a fluoroscopy image in a RAO 300 is shown in FIG. 7. The catheter is advanced to align the distal radiopaque marker 130 with the costovertebral joint 61. Since the sympathetic trunk 54 is next to the costovertebral joint 61 the gap between the distal radiopaque marker and the ablation element may ensure the sympathetic trunk is not injured. The gap may be for example a length in a range of 0 to 25 mm (e.g., a range of 3 to 25 mm, a range of 5 to 25 mm, a range of 5 to 20 mm). Optionally, an inflatable balloon 134 may be positioned on the catheter shaft within the gap, which may help to anchor the catheter or contain ablation energy proximal to the balloon. Optionally, the catheter shaft 138 distal to the ablation element may be narrower or more flexible than the remainder of the shaft to facilitate delivery through the narrower distal portion of the intercostal vein. Optionally, the ablation element(s) has a length capable of ablating to the anterior midline of the vertebra 69 when the distal radiopaque marker is aligned with the costovertebral joint. For example, the ablation element(s) may have a total length in a range of 5 to 25 mm (e.g., in a range of 10 to 25 mm, in a range of 15 to 20 mm). The ablation catheter may have a proximal radiopaque marker located just proximal to the ablation element(s). Optionally, prior to delivering ablation energy a user may image the proximal radiopaque marker to ensure it is at the anterior midline of the vertebra 69. If the proximal radiopaque marker is to the left of the midline 69, for example if the patient is extremely small, there may be a risk of injuring a non-target tissue such as the thoracic duct or esophagus. To mitigate this risk a catheter with a smaller sized ablation element may be used or if the ablation element is made of a plurality of ablation elements only the elements between the midline 69 and distal radiopaque marker may be activated for ablation. Conversely, if the proximal radiopaque marker is to the right of the midline 69, for example if the patient is extremely large, there may be a risk of missing the GSN. To mitigate this risk another ablation may be performed at another intercostal level or within the same intercoastal vein with the position of the ablation element retracted until the proximal radiopaque marker is aligned with the midline 69.

In a fourth embodiment of a method of ablating a right GSN an ablation catheter having an ablation element 131, which may include a plurality of ablation elements, a distal radiopaque marker located at a distal end of the ablation element(s), and a proximal radiopaque marker located at a proximal end of the ablation element(s) is advanced from an azygos vein into an intercostal vein at one of the lower three thoracic levels (e.g., T9, T10, T11). The C-Arm is obliquely angled to the right to maximize the 2D projection of the section of intercostal vein between the costovertebral joint 61 and anterior midline of the vertebra 69 (FIG. 5). For example, the C-arm may be positioned with a Right Anterior Oblique (RAO) angle in a range of 25° to 65° from AP (e.g., in a range of 30° to 60°, in a range of 35° to 55°, about 30°). The catheter is advanced to align the distal radiopaque marker with a position relative to the costovertebral joint and the opposing edge of the vertebral body in the oblique view. For example, the distal radiopaque marker may be aligned with a point that is midway between the costovertebral joint and the opposing edge of the vertebral body in the oblique view. The ablation element(s) may have a total length expected to cover the GSN position range 68 in most patients. Similar to the previously described methods, the proximal end of the ablation element(s) may be at the anterior midline of the vertebra 69 or to the left in centered or left-biased azygos situations and may be in the azygos vein in right-biased azygos situations. Ablation energy may be delivered from the ablation element(s) to ablate the range without moving the catheter. Optionally, the catheter may be moved to another intercostal level and a second ablation may be made using the same method steps.

Performing any of the exemplary embodiments of placement strategy disclosed above, when the ablation element 131 has a total length less than 30 mm (e.g., less than 25 mm, less than 20 mm, about 15 mm) it is expected that in a large majority of patients the sympathetic trunk will be spared from injury even if the azygos vein is right-biased. Additionally, when performing the methods herein, when the ablation element 131 has a total length greater than or equal to 15 mm it is expected that in a large majority of patients the GSN will be ablated. Therefore, the ablation element 131 may have a total length in a range of 15 mm to 30 mm to be effective and safe for a large majority of patients using these placement strategies. However, smaller ablation element total length may be suitable for exceptional patients. For example, the ablation element may have a total length in a range of 5 to 25 mm (e.g., in a range of 10 to 20 mm, or in a range of 10 to 15 mm).

As used herein, ablation element may refer to a single structure or a plurality of structures. For example, as used herein, ablation element may include a plurality of ablation electrodes that are axially spaced apart, and each of which may be adapted to facilitate the delivery of ablation energy.

Once acceptable ablation element placement is achieved, for example using one of the exemplary embodiments of placement strategy herein, ablation energy may be delivered from the ablation element or plurality of ablation elements without having to move the catheter. Ablation energy may be delivered from the ablation element to ablate tissue circumferentially around the intercostal vein a depth in a range of 2 mm to 10 mm (e.g., a range of 2 mm to 8 mm, a range of 3 mm to 8 mm, about 5 mm). Optionally, the procedure may be repeated at another thoracic level (e.g., a more cranial level, a more caudal level, another of T9, T10, T11 intercostal veins on the same side of the patient) especially if the azygos is right biased. Alternatively or in addition to having distal and proximal radiopaque markers at both ends of an ablation element or plurality of ablation elements, the ablation element(s) itself may be radiopaque and the same methods herein may be used to position the distal or proximal end of the ablation element(s) relative to anatomical landmarks (e.g., midline of the spine, costovertebral joint, etc.). The phrase radiopaque marker as used herein may thus describe an ablation element if the ablation element is radiopaque. In some alternative embodiments, a radiopaque markers may comprise a relatively longer radiopaque marker positioned under or next to one or more ablation elements wherein the proximal end of the long radiopaque marker is at least aligned with the proximal end of the ablation element or extending proximal of the ablation element by up to 3 mm and the distal end of the long radiopaque marker is at least aligned with the distal end of the ablation element or extending distal to the ablation element by up to 3 mm.

With any of the exemplary embodiments of placement strategy disclosed above, there may be situations when a portion of the ablation element(s) is in the azygos vein while the remainder is in the intercostal vein, in particular when the ablation catheter has an ablation element or plurality of elements having a total length in a range of 10 to 25 mm. The azygos vein is larger than the intercostal vein and has greater blood flow, which may impact the ability to create an effective ablation around the azygos vein or even in the intercostal vein and may require different energy delivery parameters than an ablation made completely in an intercostal vein. To resolve this, the ablation catheter may have a plurality of ablation elements wherein at least one is fully positioned in an intercostal vein and the remainder may be in the intercostal vein or in the azygos vein or both. Different ablation energy delivery parameters may be used for the different scenarios, for example higher power or energy may be delivered to the ablation element in the azygos vein or ablation energy may only be delivered to the element(s) that are fully or partially in the intercostal vein. The location of the plurality of ablation elements may be determined with fluoroscopic imaging or by monitoring electrical impedance between each ablation element (e.g., RF electrode) and a dispersive electrode.

Optionally, two or even three levels may be ablated, particularly if the azygos is right-biased but even if the azygos is centered or left-biased, which may further increase efficacy.

Alternative devices and methods of use may include a shorter ablation element that is used to create a relatively shorter ablation and repositioned a plurality of times to create multiple ablations within the GSN position range 68. If the azygos is centered or left-biased all ablations may be made in the intercostal vein 55 and cover the range 68. If the azygos is right-biased, ablations may be made in the intercostal vein to cover a portion of the range 68, and then ablations may be made at another intercostal level to improve the probability of ablating the GSN. Optionally, ablations may be made from the azygos vein, which may use different energy delivery parameters for example, higher energy or power.

An ablation catheter adapted to ablate a TSN (e.g., GSN) from an intercostal vein and or an azygos vein, for example using one or more of the embodiments of placement strategies disclosed herein, may have features that allow it to be delivered transvascularly to a desired location in a T9, T10, or T11 intercostal vein, be positioned relative to anatomical features to effectively ablate a target TSN while safely avoiding important non-target structures in a large majority of patients, and to deliver ablative energy capable of ablating the target TSN. The ablation catheter and system features may allow a user to ablate a TSN with relative ease and efficiency without sacrificing efficacy or safety. For example, once the ablation element(s) of the catheter are positioned (e.g., using methods disclosed herein), ablation energy may be delivered from a computerized ablation console with the press of a button or at least with minimal adjustments, repositioning, dragging, torqueing of the catheter or minimal user decisions regarding energy delivery. Even considering the variability of location of the GSN 68 and azygos vein 67 (see FIG. 5), features of ablation catheters and systems disclosed herein may allow a TSN/GSN to be ablated from one placement and energy delivery procedure or in some cases from an additional placement (e.g., in another of a T9, T10, or T11 intercostal vein) and energy delivery with a high probability of success in a large majority of patients.

Figure 8C:
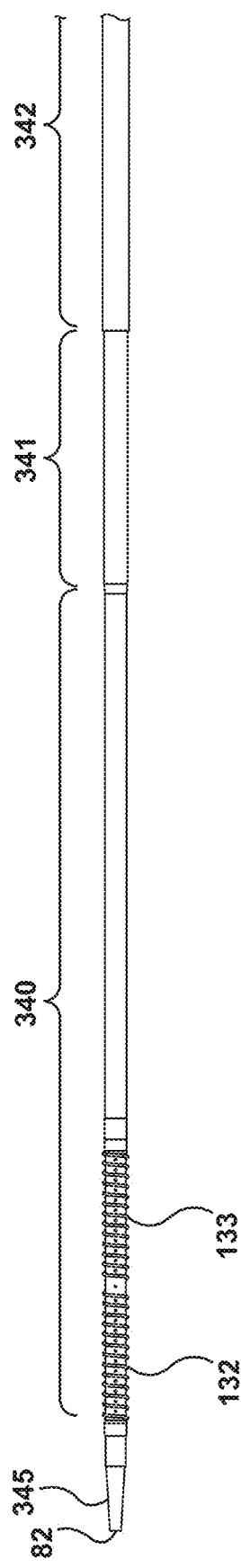
FIG. 8C is a schematic illustration of a first, second and third section of a catheter shaft.

An ablation catheter for transvascular ablation of a GSN may have a proximal end, a distal end, an elongate shaft therebetween, a distal section (e.g., comprising the distalmost 7 cm), and an ablation element on, at or carried by the distal section. The ablation element may be adapted (including sized and/or configured) to create an ablation having a length in a range of 5 mm to 25 mm, preferably 10 to 25 mm (such as 15 mm to 20 mm) and a radial depth of at least 5 mm from the vessel surface. A handle may be located on the proximal end of the catheter to contain electrical or fluid connections or facilitate handling of the catheter. The elongate shaft from a strain relief region to the distal tip may have a length of 100 cm to 140 cm (such as from 110 cm to 130 cm, such as about 120 cm) allowing the distal section to be delivered from an arteriotomy such as a femoral vein access (or other access location such as jugular vein, brachial vein, radial vein, hepatic vein or subclavian vein) to a T11 intercostal vein in a large majority of human patients, or a length of 50 cm to 140 cm allowing the distal section to be delivered from a jugular vein access to a T11 intercostal vein in most patients. To be deliverable through a 9 F delivery sheath the catheter may have a maximum outer diameter of 3 mm (e.g., 2.5 mm, 2 mm, 1.5 mm) at least in its delivery state. The catheter may optionally have a deployable structure that expands beyond this dimension once advanced from the delivery sheath and positioned in a target vessel in some embodiments. An ablation catheter for delivering an ablation element to an intercostal vein, in particular a T9, T10 or T11 intercostal vein, from an endovascular approach including approaching the intercostal vein from an azygos vein may have a shaft with features that facilitate easy tracking over a guidewire, pushability, transfer of translation forces from the handle of the catheter, and passing over a tight bend from the azygos vein to the intercostal vein without kinking. As shown in FIG. 8C, the catheter shaft may comprise a first section 340, a second section 341 and a third section 342. The first section 340 may be more flexible than the second and third sections and may carry the ablation element such as two coiled electrodes 133 and 132 as shown. This first section may have a flexibility capable of passing over the tight bend from the azygos vein to intercostal vein (e.g., having a radius of curvature >=5 mm, and angle up to 120 degrees). The first section may have a length in a range of 60 mm to 100 mm (e.g., about 65 mm) and may be made from a single lumen Pebax® tube having a durometer from 50 to 60 D, such as 55 D.

The second section 341 may have a flexibility between that of the first and third sections and function as a transition region and strain relief to resist kinking. For example, the second section may have a length in a range of 15 mm to 25 mm (e.g., about 20 mm) and may be made from a single lumen Pebax® tube having a durometer from 60 D-70 D, such as from 60 D-65 D, such as 63 D.

The third section 342 may be at least a portion of the proximal region of the elongate shaft and may be adapted for pushability, kink resistance, torque transmission, and flexibility. For example, the third section of the elongate shaft may span from the proximal end of the catheter to about 85 mm (e.g., in a range of 75 mm to 100 mm) from the distal end and may optionally have a metal wire braid embedded into an outer layer of the shaft. An example material for the third section of the elongate shaft may be extruded Pebax® having a durometer from 70 D to 75 D, such as 72 D, for example. For example, the first section 340 may be more flexible than the second section 341 section, which may be more flexible than the third section 342 and flexibility may be increased by using a lower durometer material or more flexible braided outer layer or no braided outer layer. The maximum outer diameter of the elongate shaft, at least in a delivery state, may be in a range of 1.5 to 3 mm. Optionally, as shown in FIG. 8C, the first section 340 of the shaft may be made from a tube having a smaller diameter than the second section 341, which in turn may have a smaller diameter than the third section 342 of the shaft. For example, the first section may be made of a tube having an outer diameter of 2 mm; the second section may be made of a tube having an outer diameter of 2.5 mm; and the third section may be made of a tube having an outer diameter of 3 mm. Optionally, the elongate shaft may have a tapered, soft distal tip 345, which may have a length in a range of 5 mm to 30 mm (e.g., about 8 mm), and which may be softer than the first section. Optionally, the first, second, or third sections of the shaft may have a lubricious coating on the exterior surface to further improve delivery through vasculature. A guidewire lumen may pass through the elongate shaft with an exit port 82 at the distal tip of the shaft. The guidewire lumen may be made from, for example, a 0.014" ID polyimide tube located in a lumen of the shaft.

The ablation catheters may have an ablation element adapted to deliver ablative energy to a target nerve up to 5 mm from the vessel surface for a total length in a range of 10 mm to 25 mm, such as 10 mm to 20 mm, such as 15 mm to 20 mm. The ablation element may be made of a plurality of ablation elements (e.g., two) positioned within a region of the shaft having a total length in a range of 10 mm to 25 mm, such as 10 to 20 mm, such as 15 mm to 20 mm even if the ablation elements are axially spaced apart. The ablation element(s) may include one or more of an RF ablation electrode, a coiled wire electrode, a laser cut RF electrode, an RF electrode printed with conductive ink, an RF electrode on an expandable balloon (e.g., made from conductive ink or flexible circuits), a conductive membrane RF electrode, an RF electrode on an expandable cage or mesh, an ultrasound ablation transducer, electroporation electrodes, a cryoablation element, or a virtual RF electrode.

The ablation element may be adapted to deliver ablation energy circumferentially, that is radially symmetric around the ablation element and around the vessel in which the ablation element is positioned. Although the GSN always passes anterior to the intercostal vein and azygos, it is safe and acceptable to ablate tissue around the intercostal or azygos veins, and ablating circumferentially may allow for a simpler and faster procedure that is also less prone to user error because aiming the energy delivery is not necessary. Features that may allow for circumferential ablation may include, without limitation, ablation electrodes that expand to contact the vessel wall evenly around the circumference of the vessel, ablation electrodes that are used with an electrically conductive fluid, electrically insulative balloons or deployable structures that contain ablative energy in a segment of a target vessel allowing it to be directed radially, ablation elements that direct ablation energy circumferentially such as cylindrical ultrasound transducers.

In some embodiments, the ablation element is an RF electrode and saline may be delivered to the vessel in fluid communication with the RF electrode. An irrigation lumen in communication with irrigation ports may located distal to the ablation element, under the ablation element (in some designs where irrigated saline can pass through the ablation element), or in a deployable structure in some embodiments). An irrigation lumen may be for example a lumen in the elongate shaft in fluid communication with a tube on the catheter's proximal end that is connectable to a fluid source and pump.

Optionally, at least one deployable occlusive structure (e.g., balloon, bellows, wire mesh, wire braid, coated wire mesh, or coated wire braid) may be positioned on the shaft distal to the ablation element. The deployable structure may function to anchor the catheter in place during energy delivery and possibly to improve safety by avoiding ablation of the sympathetic trunk by providing an electrical insulator or containing saline proximal to the deployable structure.

Optionally, a deployable occlusive structure may be located just proximal to the proximal end of the ablation element(s) which may function to divert blood flowing in the azygos vein away from the ablation zone. For example, a deployable occlusive structure may be a balloon such as a urethane balloon having a length (along the axis of the shaft) of about 2.5 mm and an inflated diameter of about 2.5 mm to 7 mm (e.g., 3 mm to 6 mm, 4 mm to 5 mm). The balloon may be in fluid communication with an inflation port connecting the balloon with an inflation lumen connectable to an inflation source on the proximal end of the catheter. Optionally, the inflation lumen may be in fluid communication with an irrigation lumen connectable to an irrigation source and pump. Optionally such a catheter may have a balloon with holes that allow irrigation fluid to exit the inflated balloon and flow toward the ablation element(s).

Ablation catheters may have a proximal radiopaque marker positioned on the shaft at or proximal to the proximal end of the ablation element(s). Optionally, ablation catheters may include a distal radiopaque marker which may be positioned on the shaft at or distal to the distal end of the ablation element. Optionally, there may be a space between a distal radiopaque marker and the distal end of the ablation element, the space having a length in a range of 0.1 mm to 25 mm, such as 0.1 mm to 5 mm, such as 0.1 mm to 3 mm, such as 0.5 mm, 1 mm, or 1.5 mm. For example, as shown in FIG. 2 a distal radiopaque marker 130 may be aligned with or positioned relative to an anatomical landmark such as the costovertebral joint 61 and a space 135 (e.g., 0.1 mm to 25 mm) is between the distal radiopaque marker 130 and the distal end of the ablation element 132 ensuring the ablation element is safely distant from the sympathetic trunk 54. Optionally, a deployable structure 134 may be positioned in the space transitionable between a contracted state (OD similar to the shaft OD e.g., in a range of 1.5 mm to 3 mm) and deployed state (OD increases to a range of 3 to 7 mm). The deployable structure may be a balloon, bellows, wire mesh, wire braid, coated wire mesh, or coated wire braid.

An example of an ablation catheter that is sized and adapted for GSN ablation is shown in FIG. 2. Ablation catheter 81 has an elongated shaft sized and adapted to reach a T11 intercostal vein from an introduction site at a femoral vein or jugular vein. The distal section of catheter 81, shown positioned in an intercostal vein 55, includes a distal radiopaque marker 130 that is aligned with or positioned relative to a costovertebral joint 61, an ablation element 131 comprising or consisting of a distal conductive coiled RF electrode 132 and a proximal conductive coiled RF electrode 133, an optional inflatable balloon 134 disposed between the ablation element 131 and the distal radiopaque electrode 130. The distal radiopaque marker 130 is optionally spaced distally apart from the distal end of the ablation element 132 by a distance 135 for example in a range of 0 to 25 mm (e.g., such as a range of 0.1 mm to 20 mm, such as a range of 0.1 mm to 15 mm, a range of 0.1 mm to 3 mm, such as 0.5 mm, 1 mm, or 1.5 mm). Catheter 81 also includes a proximal radiopaque marker 136 that is located at or near a proximal edge of the ablation element 131. In some embodiments proximal radiopaque marker 136 is axially spaced between 0 mm and 25 mm from a proximal end of ablation element 31 (which may be from a proximal end of ablation element 133).

The exemplary axial distances between markers and electrodes described herein (e.g., 0 mm to 25 mm, or 0 mm to 15 mm) may be integrated into any other ablation catheter herein unless indicated herein to the contrary.

Ablation electrodes 132 and 133 (or any other ablation electrode herein) may be made from, for example, Nitinol wire coiled around the catheter shaft, which may allow the electrodes to be flexible so they can traverse a tight bend from the azygos vein to the intercostal vein and also create a long ablation (e.g., 5 to 25 mm). Nitinol is an example of a superelastic material that allows the ablation element(s) to bend when traversing anatomical bends, and then elastically return to a linear or straight configuration once the electrode is past the bend.

Any of the distal sections herein may thus be described as a distal section that has an at-rest (as manufactured) linear or straight configuration. This would be in contrast to distal sections that may revert or assume non-linear at-rest configurations (e.g., a distal section with electrodes thereon that returns to a coiled configuration).

Optionally, the ablation catheter 81 includes at least one irrigation port 137 (as shown in FIG. 2) in fluid communication with an irrigation lumen that is near the coil electrodes for delivering a fluid such as saline. Saline delivery may facilitate delivery or removal of the device, or can be used during energy delivery to improve ablation formation and prevent overheating, for example. Optionally, catheter 81 may include a guidewire lumen 82 for delivery over a guidewire 79.

FIG. 8A illustrates a portion of an exemplary ablation catheter, including at least a portion of a distal section thereof. The ablation catheter in FIG. 8A includes an ablation element that includes a distal ablation element and a proximal ablation element. The ablation element (and other ablation elements herein) includes or consists of a distal conductive coiled RF electrode 132 and a proximal conductive coiled RF electrode 133, as shown in FIG. 8A. Both distal and proximal coiled electrodes may be helical coils positioned around and at least partially on the outer surface of the shaft, optionally in a groove in the shaft. The coiled electrodes may be helical, and may have varying directions, pitches, or wire thickness, and may be made from a round wire or ribbon wire of electrically conductive material such as stainless steel or superelastic Nitinol, optionally electropolished, optionally including a radiopaque material such as platinum iridium. Alternatively, one or more coiled electrodes may be made from a laser cut tube such as a Nitinol tube forming a coiled pattern or other flexible pattern. Alternatively, the ablation element (e.g., ablation element 131) may be made from a distal and a proximal flexible electrode in the form of wire mesh or braid. Alternatively, the flexible ablation element may comprise a plurality of ring electrodes each having a length no more than 5 mm, such as 3 mm. Optionally, the flexible ablation element may have an expandable diameter transitionable from a contracted delivery state to an expanded deployed state (e.g., having an outer diameter up to about 5 mm) so it can expand to contact the vessel wall.

Electrodes herein, such as the proximal and distal electrodes herein (e.g., distal electrode 132 and proximal electrode 133) may have a length that is in a range of 4 mm to 12 mm, such as 5 mm to 11 mm, and in some embodiments they are or about 5 mm, 5.5. mm, 6 mm, 6.5 mm, 7.0 mm, 7.5 mm, 8 mm, 8.5 mm, 9 mm, 9.5. mm, 10 mm, 10.5 mm, or 11 mm. Proximal and distal electrodes may have the same or substantially the same lengths, including lengths that are in the ranges provided herein (e.g., 5 mm to 11 mm). In some embodiments electrodes may have different lengths. For example, in some examples distal electrode 132 may be longer than proximal electrode 133, but the electrodes individually may have any of the lengths herein. In some examples distal electrode 132 may be shorter than proximal electrode 133, but the electrodes individually may have any of the lengths herein.

For catheters that have a plurality of electrodes, each electrode may be connected to an independent conductor passing through the elongate shaft to the proximal region of the catheter where it is connectable to an extension cable or ablation energy source. This can allow each electrode to be independently energized in monopolar mode or bipolar mode.

For some catheters with distal and proximal electrodes, the catheters may include a gap between a distal end of the proximal electrode and a proximal end of the distal electrode. In some embodiments the gap may be in a range of 0 to 5 mm, such as 0 mm 4 mm, such as 0.1 mm to 1.25 mm, such as 0.25 mm, 0.5 mm, 0.75 mm, 1 mm, or 1.25 mm. Preferably the proximal and distal electrodes are not in electrical communication with one another. Alternatively, the proximal and distal electrodes may at least partially overlap one another along their lengths, as long as they are not in electrical communication with one another.

A gap between proximal and distal electrodes may be such that it is not so large that it prevents a continuous ablation lesion to be formed. Gaps described herein (e.g., 0 mm to 5 mm, such as 0.1 mm to 1.25 mm, such as 0.25 mm, 0.5 mm, 0.75 mm, 1 mm, or 1.25 mm) can provide the exemplary benefit of providing for continuous lesion formation.

Ablation catheters herein may include one or more temperature sensors. FIG. 8A illustrates an exemplary ablation catheter that comprises at least one temperature sensor. The ablation catheter shown includes, for example, a proximal temperature sensor 139 that may be positioned in contact with proximal electrode 133, and optionally on the proximal end of proximal electrode 133. The ablation catheter shown also includes a distal temperature sensor 140 that may be positioned in contact with distal electrode 132, and optionally on the distal end of the distal electrode. Any of the ablation catheters herein may optionally include another temperature sensor that may be positioned between proximal and distal electrodes, or between a plurality of electrodes. For catheters that include one or more temperature sensors, the temperature sensor(s) may be thermocouples (e.g., T-type) or thermistors. Optionally, at least one temperature sensor may radially extend or be radially extendable from the catheter shaft to contact tissue up to 3 mm away from the catheter surface. The temperature sensor(s) may be connectable at the proximal region of the catheter to a computerized energy delivery console where signals from the sensors may be input and used in an energy delivery control algorithm.

Any of the ablation catheters herein may include one or more irrigation ports (which may be referred to herein as holes or apertures) in fluid communication with an irrigation lumen that is connectable to a fluid source at the proximal region of the catheter for delivering a fluid such as saline (e.g., normal or hypertonic saline) to the vessel. The ports may be formed in one or more layers of the elongate shaft to create the fluid communication between the port and the irrigation lumen. The fluid may function to cool or remove heat from the electrode(s) and/or vessel wall, to flush blood from the vessel to reduce risk of clot formation or improve ablation consistency, to conduct electrical energy from the ablation electrodes, to control pressure in the vessel, to facilitate delivery of the distal section of the ablation catheter to a target vessel (e.g., intercostal vein), or to facilitate removal of the distal section of the ablation catheter from the target vessel. Optionally, one or more irrigation ports may be distal to the ablation element(s), or distal to each of the plurality of flexible ablation elements. In some embodiments, any of the irrigation port(s) may be positioned radially under the flexible ablation element(s). In some embodiments, one or all irrigation ports may be disposed between windings of coiled ablation element, such that the port is not radially under the winding of the ablation element. Optionally, an irrigation port may be positioned in an axial gap or space between adjacent ablation electrodes. Optionally, one or more irrigation ports may be in a cavity of a deployable occlusive structure (e.g., balloon) and may function to inflate the balloon, wherein the balloon may have a perforation on its proximal side that allows the fluid to escape the balloon into the target region of the vessel.

FIGS. 8A-10 illustrate distal sections of ablation catheters that include a plurality of irrigation ports between windings of coiled ablation elements (although only one port 137 is labeled, the others can be seen in the figures). In the side views shown in FIGS. 8A, 8B, 9 and 10, the exemplary ports are linearly aligned, parallel to a long axis of the distal section. Additionally shown in the side views of FIGS. 8A, 8B, 9 and 10, there is an irrigation port between every adjacent pair of winding material (even though coiled elements 132 and 133 are each formed by a continuous winding along their lengths). The central port 137 axially between the ablation elements may or may not be included. In any of the embodiments, every port in the distal section may be between a winding (in the side view). Alternatively stated, in any of the embodiments, none of the ports may be radially under a winding structure of the ablation element.

Figure 8D:
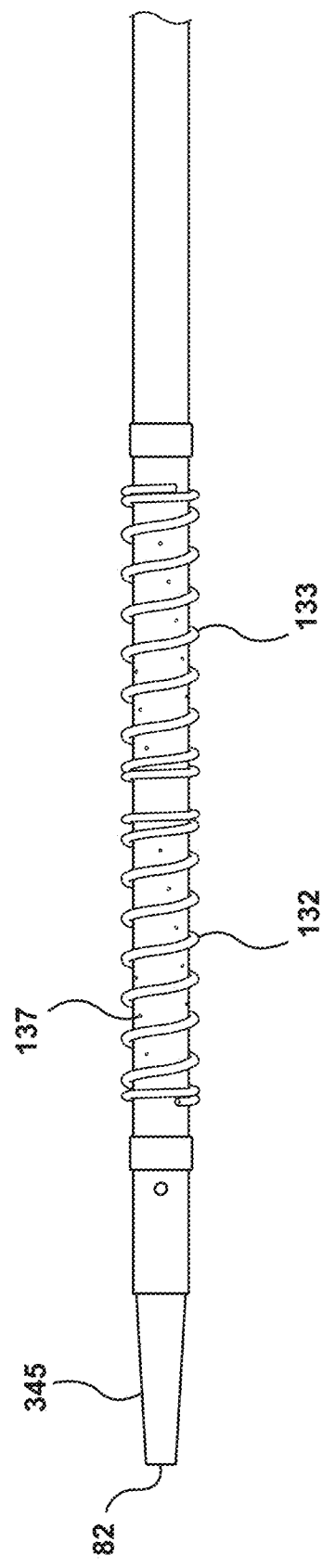
FIG. 8D is a schematic illustration of a distal portion or section of an ablation catheter having irrigation holes arranged in a helical pattern between windings of a helical electrode and an irrigation hole distal to the distal electrode.

Optionally, as shown in FIG. 8D, irrigation holes (which may be referred to herein as apertures or ports) 137 may be positioned between windings of the coil electrodes and be circumferentially distributed to deposit saline along the length of the ablation electrodes as well as circumferentially around the electrodes. In FIG. 8D the irrigation holes 137 follow a helical path, optionally of the same pitch as the coil electrode with equal spacing between holes as shown in FIG. 8D. As shown, even though the example in FIG. 8D does not include a central port between electrodes (as do the examples in FIGS. 8A and 8B), the irrigation holes may still be considered to have or follow a helical path. That is, there may be a greater spacing between sections of helical ports than between adjacent ports in the sections. The example shown in FIG. 8D may, however, also include a central irrigation port between electrodes (as in the examples of FIGS. 8A and 8B).

The irrigation holes may be created (e.g., laser drilled) in the tube (or tubular member) prior to or after positioning or connecting the electrode coil(s) to the tube. Optionally, size and quantity of irrigation holes are chosen along with an irrigation flow rate range to maintain a back pressure in the irrigation lumen so that irrigated saline jets from the irrigation holes, which may evenly, consistently and predictably fill the vessel (e.g., intercostal vein) with saline. For example, an ablation catheter may be adapted to accept a saline flow rate in a range of 30 to 50 mL/min during ablation and may have irrigation holes with a diameter of 0.003" and a quantity of 34 holes or alternatively holes with a diameter of 0.009" and a quantity of 17 holes.

Figure 8E:
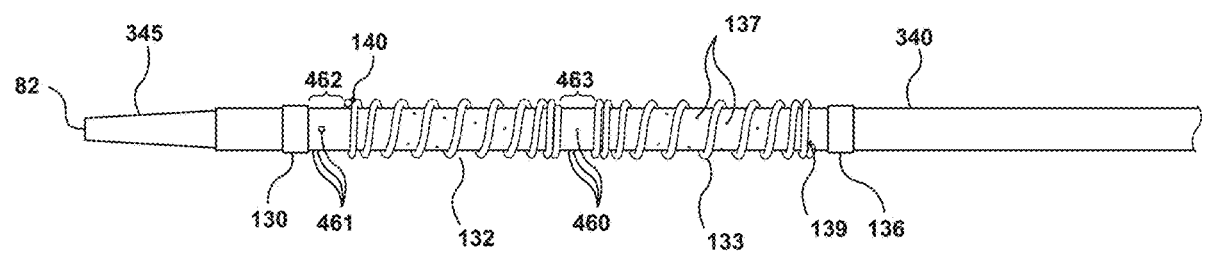
FIG. 8E is a schematic illustration of a distal portion of an ablation catheter having irrigation holes arranged in a helical pattern between at least some windings of a helical electrode and a plurality of irrigation holes distal to a distal electrode and between proximal and distal electrodes.

Optionally, there may be more holes associated with the distal electrode than the proximal electrode, or vice versa. Optionally, one or more irrigation holes may be positioned distal to the distal electrode, for example within 3 mm distal of the distal electrode. This may improve cooling of the distal electrode including a temperature sensor in communication with the distal electrode, in particular if the temperature sensor is located at the distal end of the distal electrode. For example, as shown in FIG. 8E, a schematic illustration of a distal portion of an ablation catheter, irrigation holes 137 may be arranged in a helical pattern between at least some windings of a proximal helical electrode 133 and likewise irrigation holes 137 may be arranged in a helical pattern between at least some windings of a distal helical electrode 132, and a plurality of irrigation holes 461 may be arranged distal to the distal electrode and a plurality of irrigation holes 460 between the proximal and distal electrodes. In this example, the irrigation holes 137 that are between windings of the coiled proximal 133 and distal 132 electrodes follow a helical path around the shaft 340 having the same pitch as the helical coil electrodes or at least sufficiently the same pitch such that the holes 137 remain between the windings of the coiled electrodes. Furthermore, the holes 137 may be spaced apart from one another along the helical pathway in regular intervals, for example every 96 degrees (or a regular interval in a range of 4 to 110 degrees), which may provide an even circumferential distribution of irrigation. The pitch of the coiled electrodes may get tighter at one or both ends of each coil. For example, each end of each coil may wrap around the shaft 340 and contact the adjacent turn of the coil making a closed loop at each end of the coil, where the connections are soldered together. This may help to hold the coil securely to the shaft and contain the ends to avoid a risk of a loose wire end getting caught on tissue or the delivery sheath. The same solder joint may include an RF conductor and optionally thermocouple wires forming a thermocouple junction as shown as distal thermocouple junction 140, which is shown at the distal end of the distal electrode 132, and proximal thermocouple junction 139, which is shown at the proximal end of the proximal electrode 133. Due to the decreased coil pitch at the ends of the coils, there is less room to place irrigation holes. Optionally, irrigation holes may be positioned only in central regions of the coiled electrodes and not where the pitch decreases at the ends, for example within the beginning or ending 3 turns. To compensate for reduced irrigation at the ends of the coiled electrodes when holes are not placed in the last few turns, irrigation holes 461 may be positioned distal to the distal electrode 132, and irrigation holes 460 may be positioned between the proximal 133 and distal 132 electrodes. For example, a quantity of distal holes 461 in a range of 1 to 5 (e.g., 3) may be circumferentially evenly spaced (e.g., radially symmetric) and within a distance 462 (e.g., in a range of 0.1 to 3 mm, in a range of 0.1 to 1 mm) of the distal end of the distal electrode 132. Similarly, for example, a quantity of holes 460 between the electrodes in a range of 1 to 5 (e.g., 3) may be circumferentially evenly spaced (e.g., radially symmetric) and within a space 463 (e.g., in a range of 0.5 to 1.0 mm) between the distal electrode 132 and proximal electrode 133. Since blood flows from distal to proximal in the intercostal vein, irrigated saline flowing out of distal holes 461 would sufficiently bathe and cool the distal few turns of the electrode 132; the proximal few turns of the distal electrode would be bathed and cooled by saline flowing from holes between windings as well as from the distal holes 461; likewise the distal few turns of the proximal electrode 133 would be cooled and bathed by the holes 460 between the electrodes; and the proximal few turns of the proximal electrode would be bathed and cooled by saline flowing from holes between windings as well as from the holes 460 and from other holes 137 and 462 associated with the distal electrode. In one exemplary embodiment as shown in FIG. 8E the catheter has three circumferentially evenly spaced distal irrigation holes 461, three circumferentially evenly spaced irrigation holes 460 between the proximal and distal electrodes, 15 helically evenly spaced irrigation holes 137 between windings in the distal electrode, and 15 helically evenly spaced irrigation holes 137 between windings in the proximal electrode, totaling 36 irrigation holes, each having a diameter of 0.003".

Alternatively, in any of the examples herein, irrigation holes may be positioned under the coil electrode windings as well as between the windings.

Alternatively, any of the devices herein may include a section of tube that the electrodes are positioned over that may be a porous tube made from a material that is inherently porous, for example a mesh or woven tube.

Figure 21A:
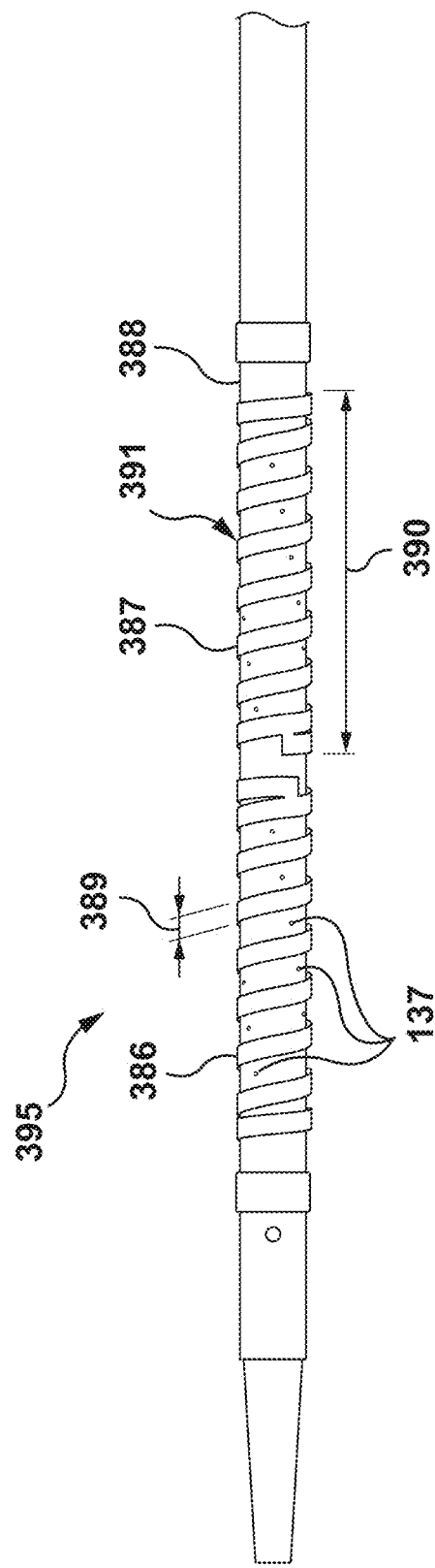
FIG. 21A is a schematic illustration of an ablation catheter with flat helical electrodes.
Figure 21B:
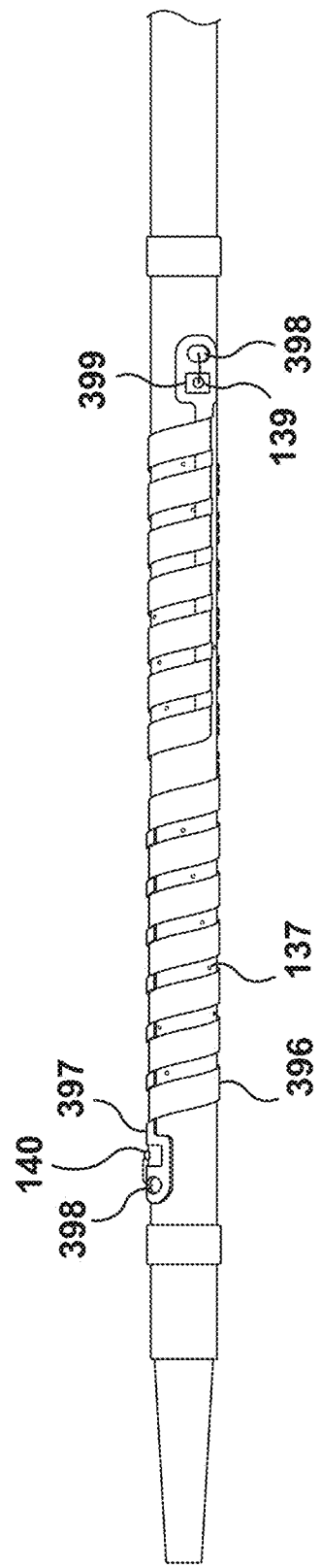
FIG. 21B is a schematic illustration of an ablation catheter with flat helical electrodes.

Alternatively, any of the coiled electrodes herein may have a flat profile such as a ribbon of conductive material wrapped helically around a tube. A flat profile compared to a round wire profile may in some situations be easier to deliver or remove from a tight vessel. FIG. 21A shows an exemplary distal portion of an ablation catheter having an ablation element 395 having a plurality of coiled electrodes (a first coiled electrode 386 and a second coiled electrode 387 in this example) made from flat ribbon wrapped helically around a tubular shaft 388. The flat ribbon may be a conductive material, optionally a superelastic Nitinol ribbon shape set into a helical coil having, for example only, an inner diameter of 0.069"+/−0.004" and a pitch of about 0.047". Superelastic Nitinol may have a benefit of kink resistance and elastically returning to a preset shape during or after being deformed when delivering the device to a target vessel. However, alternative materials such as stainless steel or a conductive alloy could be used. Optionally, at least a portion of the ribbon electrode may be made with a radiopaque material such as platinum iridium. Optionally, the surface of the ribbon electrode may be etched and passivated. The flat ribbon may have a thickness in a range of, for example only, 0.002" to 0.003" and a width 389 in a range of 0.010" to 0.020". The length 390 of each coil may be about 8 mm+/−0.5 mm. The flat ribbon electrodes may be applied to be flush with the surface of the tubular shaft. For example, the tubular shaft may be indented where the flat ribbon connects with the shaft or the tubular shaft may re-molded or softened during application of the flat ribbon to allow it to sink into the shaft. Alternatively, the flat ribbon electrodes may extend beyond the surface of the shaft, for example by the thickness of the ribbon, which may be in a range of 0.002" to 0.003". Optionally, the edges 391 of the ribbon electrode, for example on the outer diameter, may be rounded, chamfered or tapered, which may further facilitate delivery or removal of the catheter into the target vessel or may reduce high current density during delivery of RF energy. Irrigation ports 137 may be positioned between the windings of the flat ribbon electrodes as shown in FIG. 21A, or in other configurations disclosed herein. Another alternative form of a flat helical electrode, as shown in FIG. 21B, may include an assembly made from a conductive material 396 such as superelastic Nitinol, stainless steel or an alloy, on a non-conductive substrate 397 (e.g., a flex circuit), which may facilitate manufacturing. The non-conductive substrate 397 may be for example, polyimide, and the conductive trace 396 may be connected to the substrate with adhesive. The assembly may have a wire strain relief 398 in the substrate, through which conductors may pass from a lumen in the catheter shaft to a wire solder pad 399 that is in electrical communication with the conductive material 396. Optionally, temperature sensors 139, 140, such as thermocouples, may be positioned on the wire solder pad along with conductors supplying RF to the electrodes. The assembly may have a thickness in a range of 0.002" to 0.003", with a conductor thickness in a range of 0.0015" to 0.0025". The width of each trace may be in a range of 0.010" to 0.020".

Optionally, the ablation catheter may have a deployable element transitionable from a contracted delivery state (e.g., having an OD in a range of 1.5 mm to 3 mm) to an expanded deployed state (e.g., having an OD in a range of 2.5 mm to 6 mm) that functions to one or more of anchor the distal section of the catheter in the target region of the vessel, to occlude blood flow, to contain delivered fluid such as saline, to maintain vessel patency, or to act as an electrical insulator. For example, as shown in FIG. 8B, any catheter herein may also include a distal deployable element 134 coupled with optimized irrigation flow that may create a virtual electrode that provides an effective ablation without the need for wall contact. Distal deployable element 134 may be a balloon (e.g., compliant balloon) as shown in FIG. 8B, or alternatively a bellows or coated stent or mesh. Distal deployable element 134 is distal to the ablation element, which may include proximal and distal electrodes as shown in FIG. 8B.

Figure 9:
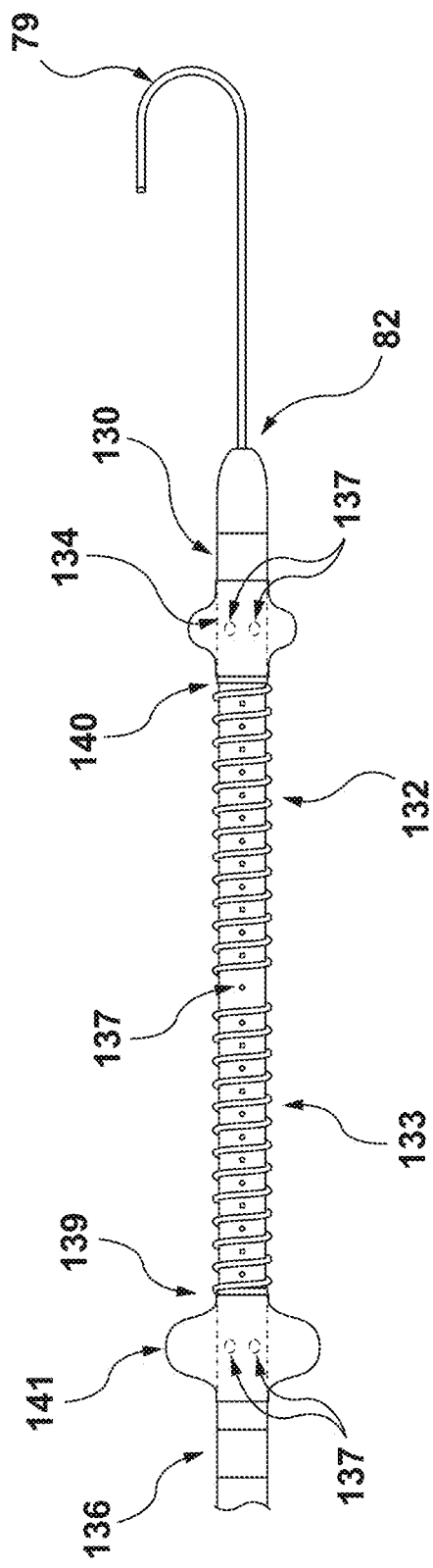
FIG. 9 is a schematic illustration of an ablation catheter with two coiled RF electrodes, a distal deployable element, and a proximal deployable element.

Optionally, any of the ablation catheters herein may have a proximal deployable element. FIG. 9 illustrates an exemplary ablation catheter that includes proximal deployable element 141 that can be contracted to have an OD in a range of 1.5 to 3 mm in a delivery state, and be deployed to have an OD in a range of 4 to 10 mm in a deployed state as shown in FIG. 9. The proximal deployable element 141 may function to one or more of anchor the distal section of the catheter in the target region of the vessel, to occlude blood flow, to contain delivered fluid such as saline, to act as an electrical insulator, to maintain vessel patency, to act as a depth stopper (e.g., having a deployed OD larger than the targeted intercostal vein) to prevent the distal section from being advanced too far into the intercostal vein, or to direct blood flow in the azygos vein away from the ostium to facilitate ablation near the ostium. A proximal deployable element and a distal deployable element coupled with optimized irrigation flow may create a virtual electrode that provides an effective ablation without the need for wall contact. A proximal deployable element may be a balloon (e.g., compliant balloon) as shown in FIG. 9, or alternatively a bellows or coated stent or mesh. Any of the catheters herein may include a proximal deployable element and a distal deployable element.

Figure 10:
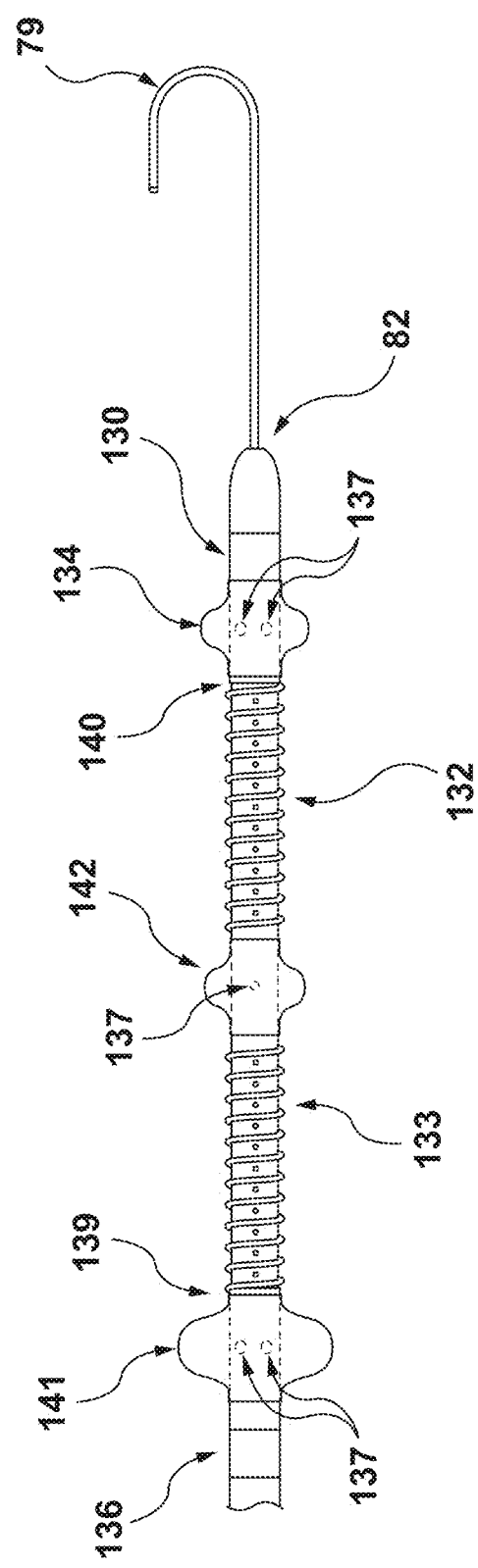
FIG. 10 is a schematic illustration of an ablation catheter with two coiled RF electrodes, a distal deployable element, a proximal deployable element, and a middle deployable element.

Optionally, any of the ablation catheters herein may include a middle or central deployable element. FIG. 10 illustrates an exemplary ablation catheter that includes a middle deployable element 142 that can be contracted to have an OD in a range of 1.5 mm to 3 mm in a delivery state, and be deployed to an expanded state (e.g., having an OD in a range of 2.5 mm to 6 mm) as shown in FIG. 10. The middle deployable element may function to one or more of anchor the distal section in the target region of the vessel, to occlude blood flow, to contain delivered fluid such as saline, to maintain vessel patency, or to act as an electrical insulator. A middle deployable element may be used to isolate the vessel between a distal deployable element and the middle deployable element and around the distal ablation element to create a virtual electrode that provides an effective ablation without the need for wall contact. Likewise, the section of vessel between the middle deployable element and a proximal deployable element may be isolated. The middle deployable element may be a balloon (e.g., compliant balloon) as shown in FIG. 10, or alternatively a bellows or coated stent or mesh. In an embodiment wherein the ablation energy is electroporation, the middle deployable element may function as an electrical insulator to direct electrical current out of the vessel in through tissue around the vessel to more effectively ablate the target nerve. In alternative embodiments, an ablation catheter may have a middle deployable element and only a distal deployable element (i.e., no proximal deployable element) or only a proximal deployable element (i.e., no distal deployable element).

The disclosure above described exemplary methods of positioning an ablation catheter within an intercostal vein to ablate a GSN while minimizing or avoiding damage to non-target structures. The ablation catheters above, including those shown in FIGS. 8A, 8B, 9, and 10, included one or more radiopaque markers (e.g., distal marker 130 and proximal marker 136) that can be used as part of those methods of positioning. While the ablation catheters in FIGS. 8A, 8B, 9 and 10 are examples of ablation catheters that can be used when performing the methods herein, it is understood that the methods can be performed with a variety of ablation catheters. It is thus understood that the methods herein are not limited by the particular ablation catheters herein. It is also understood that the ablation catheters herein need not be used with the positioning methods herein.

Alternative embodiments of TSN/GSN ablation catheters may have one or more features that are described herein, such as proximal and distal radiopaque markers spaced as described, irrigation lumens(s), temperature sensor(s), guide wire lumens, flexible shaft section, and may also include alternative ablation elements. For example, ablation elements may be RF electrodes having different configurations or ablation elements that deliver a different type of ablation energy such as ultrasound, electroporation, cryoablation, laser, chemical or other ablation modality. Ablation catheter features that are described with respect to one embodiment or example herein may be incorporated into other suitable embodiments unless the disclosure indicates otherwise. Features with the same or similar reference numbers are understood to be optionally included and can be the same component.

For example, FIG. 11 illustrates a distal section of an ablation catheter. The ablation catheter includes an ablation element that may be an RF electrode that includes a plurality of wire struts 143 running the length of the ablation element and arranged around the circumference of the shaft. The wire struts are electrically conductive, for example made from stainless steel, Nitinol or the like, and transitionable from a contracted delivery state (e.g., having an OD in a range of 1.5 to 3 mm) to an expanded deployed state (e.g., having an OD in a range of 2.5 mm to 6 mm) to contact the vessel wall, in particular an intercostal vein. The wire struts may be deployed by applying tension to a pull wire that moves a collar holding or otherwise secured to one end of the wire struts, shortening the distance between the two ends, which causes the wire struts to bend outward. The struts may be heat set in a biased configuration, such as those shown in FIG. 11. Optionally, an RF electrode may have multiple (e.g., two) RF electrodes made of wire struts, wherein the multiple electrodes are positioned next to one another similar to the coiled electrodes shown in FIGS. 8 to 10. Optionally, the wire struts may be made from a laser cut tube. Optionally the distal end, proximal end or both ends of the expandable wire electrode may have a membrane that functions to occlude the vessel when expanded and function similar to the deployable structures (e.g., balloons) shown in FIGS. 8A to 10.

Figure 13A:
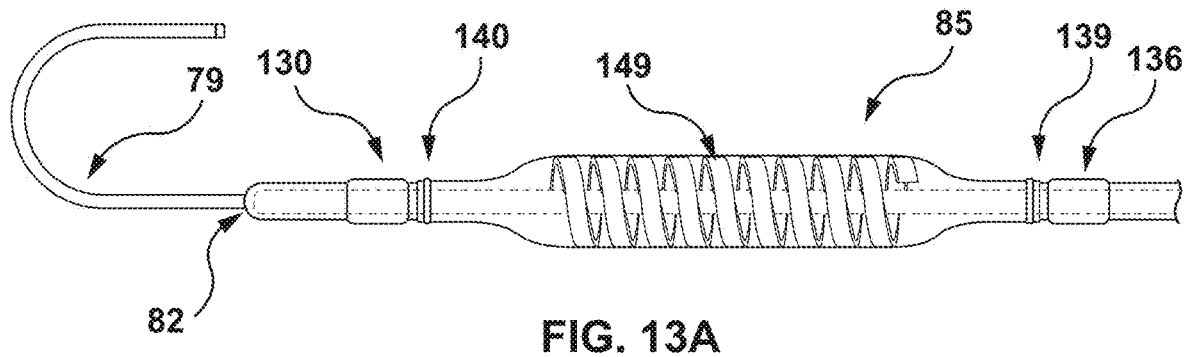
FIGS. 13A and 13B are schematic illustrations of an ablation catheter with an RF electrode comprising an expandable balloon with an RF electrode made from conductive ink on its surface.
Figure 13B:
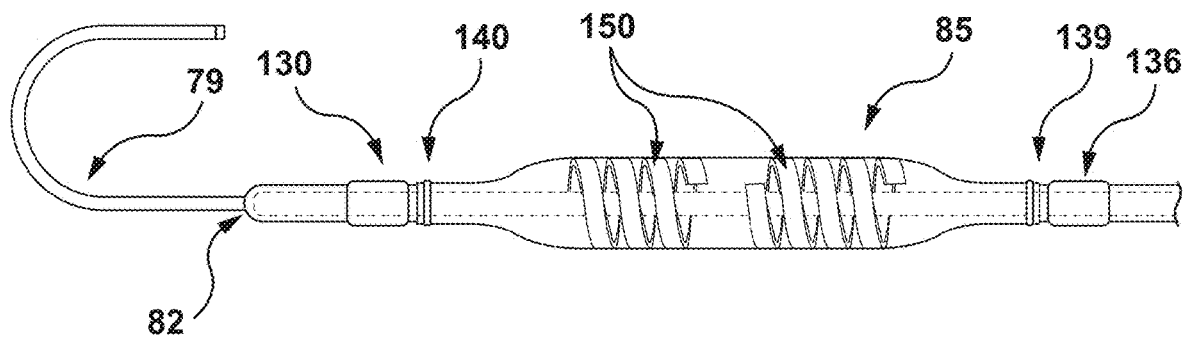
Figure 14:
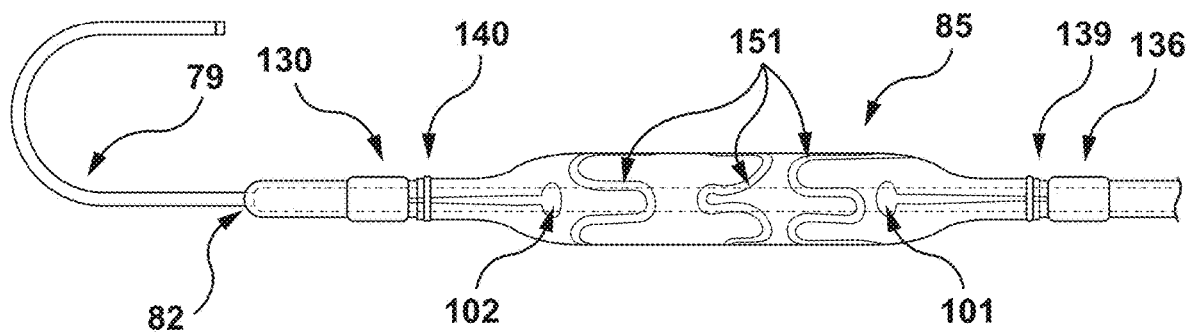
FIG. 14 is a schematic illustration of an ablation catheter with an RF electrode comprising an expandable balloon with an RF electrode on its surface in a zig-zag pattern.

FIG. 12 illustrates an exemplary ablation catheter with ablation element(s) carried by an expandable balloon. FIG. 12 illustrates a distal section of an ablation catheter with an RF ablation element, wherein the ablation element includes one or more electrically conductive element(s) positioned on expandable balloon 144. The conductive elements may be a film or conductive ink or flexible circuits. Sensors (e.g., temperature sensors) may be positioned on the balloon as well. Optionally the balloon may be inflated by delivering fluid such as saline or air into the balloon. Optionally, the conductive element(s) or the balloon may have perforations allowing fluid to pass through to cool the electrode or conduct energy. The pattern of the conductive element(s) may be cylindrical 148 (FIG. 12), helical 149 (FIG. 13A), a plurality of electrodes each having a helical configuration 150 (FIG. 13B), electrodes with a wavy (e.g., sine wave) or zig-zag pattern 151 (FIG. 14), or other pattern adapted to circumferentially ablate around a vessel. The examples shown in FIGS. 12 to 14 include optional distal and proximal radiopaque markers that can be used with any of the methods of positioning described above.

Figure 15:
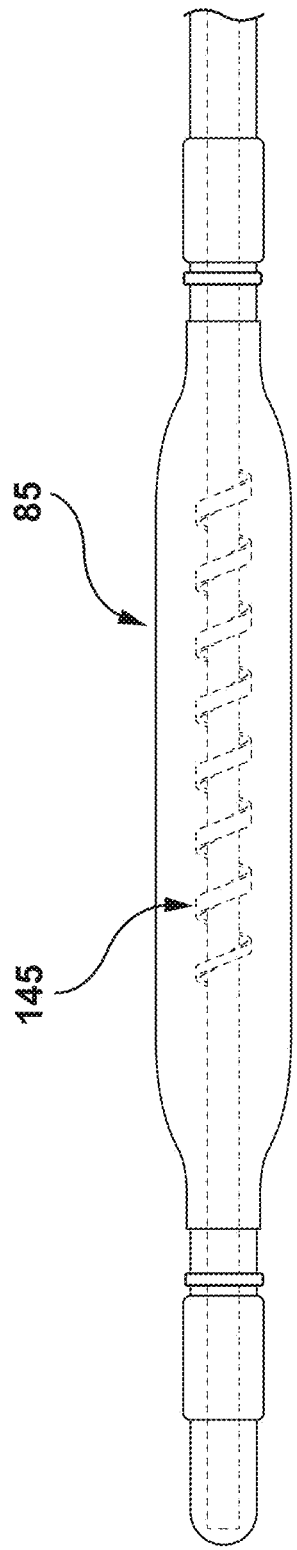
FIG. 15 is a schematic illustration of an ablation catheter with an RF electrode in a cavity defined by a membrane.

FIG. 15 illustrates an additional exemplary distal section of an ablation catheter that includes an electrically conductive element within a membrane. The catheter in FIG. 15 includes an RF ablation element that is an electrically conductive wire 145 (e.g., wire coil) on or around the catheter shaft within a cavity defined by a membrane 185. The membrane may be an ionomer, a conductive membrane, or a weeping membrane. The optional distal and proximal markers are shown distal and proximal to the balloon, respectively.

Figure 16:
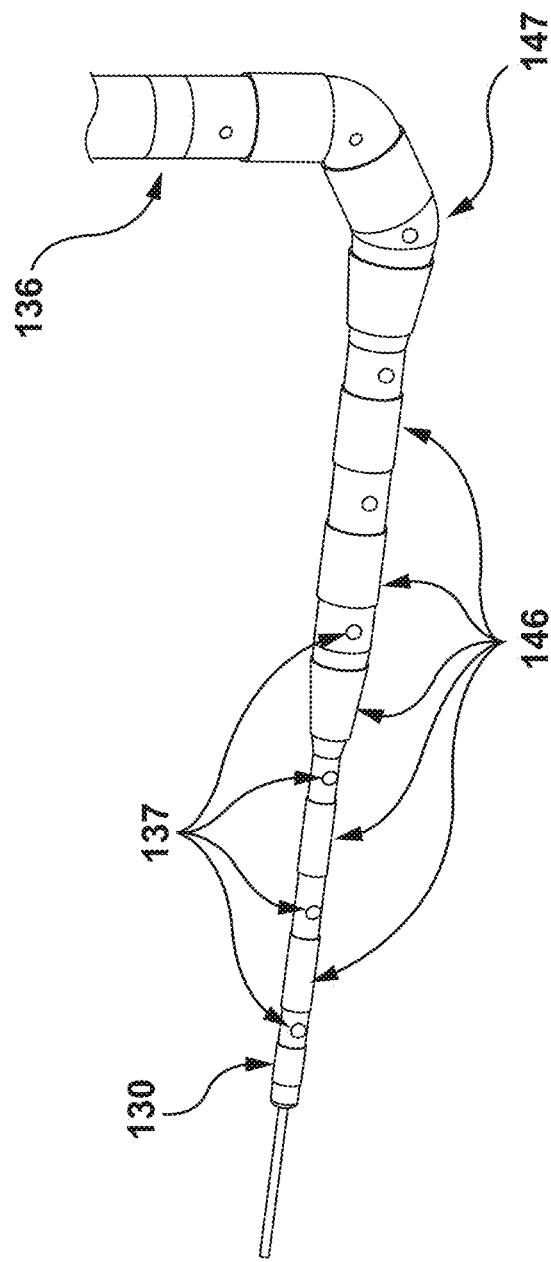
FIG. 16 is a schematic illustration of an ablation catheter with a plurality of RF electrode sections on a tapered shaft

FIG. 16 illustrates an example of a distal section of an ablation catheter, which can may be used with the methods of positioning herein. Another embodiment of an RF ablation element is shown in FIG. 16 wherein the ablation elements are a plurality of shorter RF electrodes 146 on a tapered shaft 147. This embodiment is different in that the total length of the shaft carrying ablation elements may be longer than previously described as 5 mm to 25 mm (preferably 10 mm to 15 mm). Instead, the catheter includes multiple sections (e.g., two or three) that each have a length in this range, but are selectively chosen to deliver ablation energy depending on how they fit in the intercostal vein. The tapered shaft may function to fit a range of intercostal veins (e.g., in a range of 2.5 mm to 5 mm). The distal end is narrower than the proximal end and the electrodes may be independently and selectively energized. If the distal section of the catheter is delivered to a relatively narrow intercostal vein, for example having an inner diameter of about 2.5 mm, the distal narrow portion may be advanced into the vein and selected for energy delivery, while the proximal larger portion may remain in the azygos vein and not used to delivery ablation energy. If the intercostal vein is larger, for example 5 mm inner diameter, the distal section may be advanced further into the intercostal vein until the larger electrodes are wedged into the vessel contacting the wall. The larger proximal electrodes may be selected for energy delivery while the distal electrodes are inactive to avoid injury to the sympathetic trunk. Optionally and intermediate section of electrodes may be sized to fit an intercostal vein having an inner diameter of about 3.5 mm. The plurality of electrodes may be coiled wire, laser cut tube, or solid electrodes. The electrodes may be radiopaque or have radiopaque markers associated with them so the user can image where the electrodes are positioned in the intercostal vein and choose which section of electrodes to activate.

Figure 17:
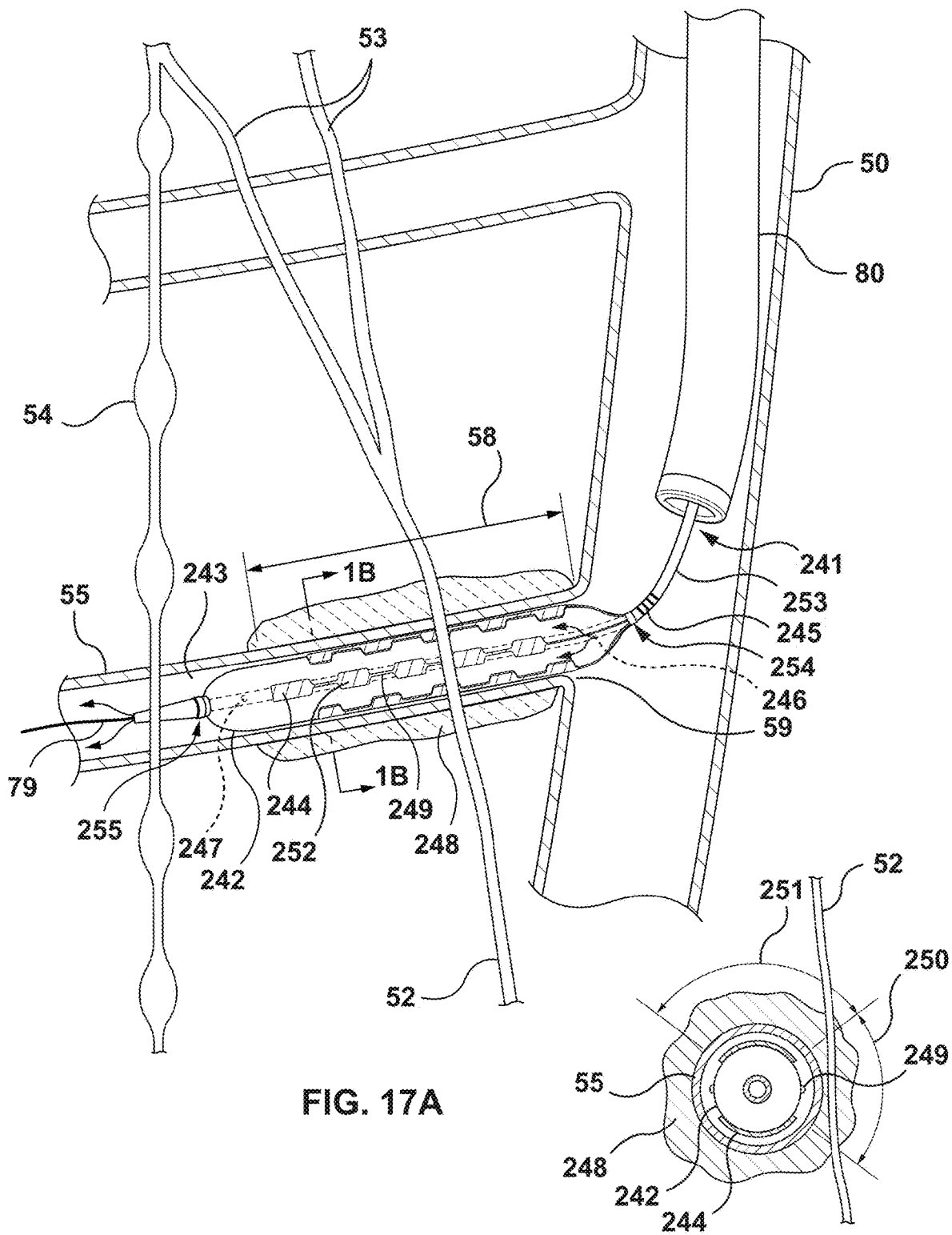
FIGS. 17A and 17B are schematic illustrations of an ablation catheter with RF electrode pads on an expandable balloon.

Another embodiment of a transvascular ablation catheter 241 for ablating a TSN or GSN from within an intercostal nerve is shown in FIG. 17A. The catheter 241 may extend along a longitudinal axis. An expandable member, for example in the form of a balloon 242 having an unexpanded state and an expanded state, may be coupled to a distal section 243 of the catheter. The expandable member (e.g., balloon) may have a circumferential treatment zone 248 (e.g., having a length in a range of 5 to 25 mm, in a range of 10 to 15 mm) extending along the longitudinal axis in the expanded state and surrounding the vessel 55. The catheter includes an electrode assembly 252, which comprises a plurality of electrode pads 244, may be mounted or otherwise secured to the balloon 242. Each electrode pad assembly may include a substrate supporting first and second electrode pads with each electrode pad having a pair of elongate bipolar electrodes and connected with an electrical trace 249. The electrode pads of each electrode pad assembly may be longitudinally and circumferentially offset from one another. The method may also include expanding the balloon in the intercostal vein so as to electrically couple the electrodes with a wall of the intercostal vein and driving bipolar energy between the electrodes of each bipolar pair so as to therapeutically alter the TSN or GSN within 5 mm of the intercostal vein such that the blood volume of the patient is redistributed for treatment of diseases such as pulmonary hypertension, or heart failure (e.g., HFpEF).

Each electrode pad may include a temperature sensor disposed between the electrodes of the pair. The expanding of the balloon may couple the temperature sensors with the wall of the intercostal vein. In some embodiments, the method may further include directing the energy to the bipolar pairs in response to a temperature signal from the temperature sensor so as to heat the wall approximately evenly.

To create an ablation having a depth of 5 mm to target a GSN from an intercostal vein the electrode pads may be cooled to allow greater power to be delivered without desiccating tissue of the vein wall, which impedes ablation depth. The electrodes may be cooled for example, by circulating coolant in the balloon 242. In one embodiment coolant may be injected into the balloon 242 from a coolant injection port 246 at one end of the balloon chamber and the coolant may exit the chamber through an exit port 247 at the opposing end of the chamber and allowed to return through the catheter through an exit lumen.

In another embodiment coolant may be deposited into the blood stream instead of returning through a lumen in the catheter. This embodiment may allow a thinner, more flexible catheter shaft or a larger coolant delivery lumen to increase flow rate of the coolant. A coolant exit port may be smaller than the coolant injection port to allow pressure to increase in the balloon to inflate it. The coolant exit port may be in communication with a lumen that does not pass through the full catheter shaft to the proximal end but instead passes to the distal end of the catheter to deposit the coolant (e.g., normal saline) into the intercostal vein. Optionally the coolant exit lumen may be the same lumen as a guidewire delivery lumen.

Electrode pads may be positioned around the balloon to make a circumferential ablation pattern that is as long as the target ablation zone 58 (e.g., up to 20 mm, about 15 mm, between 12 and 18 mm). For example, as shown in FIG. 17B, a balloon with electrode pads mounted to an elongate shaft 253 may have an undeployed state having a diameter of about 1 mm to 2.5 mm and a circumference of about 3.14 mm to 7.85 mm and be expandable to a deployed state having a diameter in a range of about 3 mm to 5 mm and a circumference in a range of about 9.4 mm to 15.7 mm. Electrode pads 244 may be separated or spaced by a distance 250 of less than 5 mm (e.g., less than 2.5 mm) and width or arc length 251 in a range of 3 mm to 3.5 mm. Electrode pads 244 may have a length of about 3 to 5 mm each. As shown in FIG. 17A, an electrode pad assembly 252 may comprise multiple electrode pads 244 arranged on four separate rows connected together by electrical traces 249, the rows evenly spaced around the circumference of the balloon 242 (e.g., four rows at each 90 degree quadrant). Longitudinally, the pads 244 on one row may be offset from pads of adjacent rows. When the balloon is in its unexpanded state the space between the electrode pads is decreased (e.g., to about 0 to 1 mm) and the adjacent rows interlock with one another. In its expanded state the space 250 between the pads expands due to the expandable balloon 242 to about 2 mm to 5 mm. The balloon 242 may be a compliant material such as latex or a non-compliant material that flexibly folds to contract.

Alternatively, electrode pads may be positioned only on one side (e.g., 50%, 40%, 30%, 25% of the balloon's circumference) to generate a directional ablation pattern that is all toward the same side and of a length of the target ablation zone 58. For a directional ablation catheter, a radiopaque marker may be positioned on the distal section of the catheter to indicate radial direction. For example, a radiopaque marker may be asymmetric and positioned on the same side or opposing side as the directional electrode pads to indicate and in use a physician may torque the catheter to aim the radiopaque marker and thus the electrode pads away from the vertebra, which is always toward the GSN. FIG. 17A shows several small electrode pads. Alternatively, the device may have larger and fewer electrode pads, for example two or three directional electrode pads (e.g., 3 to 5 mm long) on the same side of the balloon that span the target ablation zone 58. A gap (e.g., 1 to 3 mm) between electrode pads may facilitate bending of the device to traverse from the azygos vein to the intercostal vein. The ablation catheter in FIGS. 17A and 17B can include proximal and/or distal radiopaque markers, and may be used with methods of positioning described herein.

Just proximal to the balloon the catheter shaft may comprise a flexible neck 245 that allows the ablation balloon to sit in the intercostal vein's natural orientation. Given the small bend radius at this location a stiff shaft could apply force to the ablation balloon causing it to distort the intercostal vein and reduce predictability of ablation zone. A flexible neck may be made of a softer durometer polymer (e.g., Pebax®) and may have a wire coil embedded in the material, which may allow flexible bending while providing pushability. This type of flexible neck may be incorporated into other ablation catheters herein.

The electrode(s) that are most proximal may be placed just in the intercostal vein near the ostium. Blood flow through the azygos vein may metabolically cool tissue near it impeding ablation creation. A larger amount of ablation power (e.g., RF) or longer duration may be delivered to this proximal electrode(s) than the rest of the electrode(s) to compensate for the blood flow cooling.

The catheter 241 may have a distal radiopaque marker 255 positioned distal to the ablation elements, for example distal to the balloon 242, and/or a proximal radiopaque marker 254 positioned proximal to the ablation elements 244, for example proximal to the balloon 242. The distal and proximal radiopaque markers 255, 254 may be separated along the longitudinal axis of the shaft by a distance in a range of 5 mm to 25 mm (e.g., 10 mm to 15 mm). Any other features or description of radiopaque markers herein may apply to markers 255 and/or 254.

Figure 18:
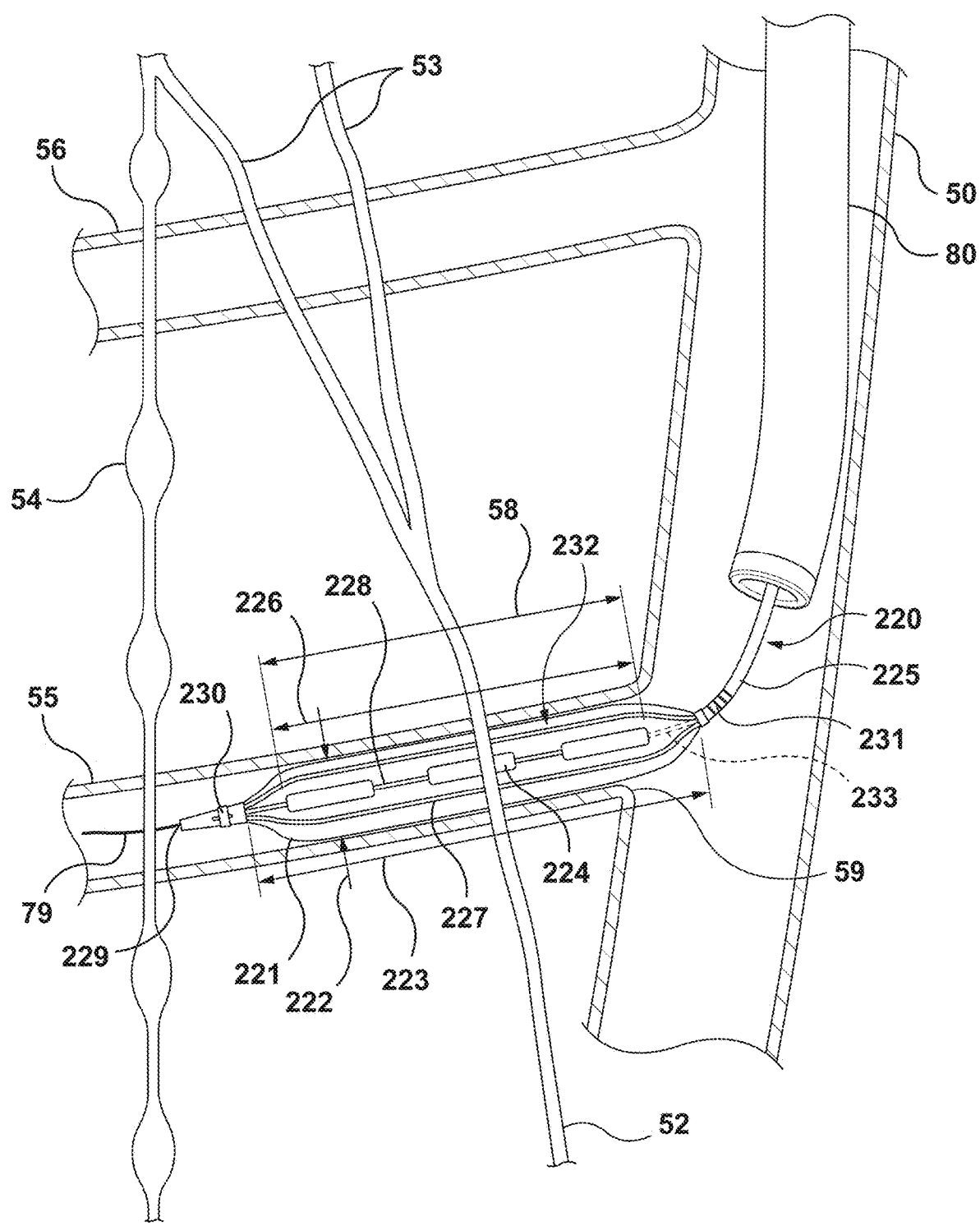
FIG. 18 is a schematic illustration of an ablation catheter with ultrasound transducers.

FIG. 18A illustrates an exemplary ultrasound ablation catheter. Catheter 220 includes an elongate shaft 225 with a proximal region and a distal section and an ablation assembly 232 mounted to or at the distal section. The ultrasound ablation catheter 220 has an inflatable balloon 221 which may have a geometry suitable for expansion in an intercostal vein (e.g., outer diameter 222 in a range of 2.5 to 5 mm in its inflated state) and a length 223 in a range of 8 to 30 mm. Within the balloon 221, multiple ultrasound transducers 224 are positioned on a shaft 233 centered in the balloon 221. The transducers 224 may be placed serially spanning a length 226 that is in a range of 5 to 25 mm to generate an ablation of a similar length capable of creating an ablation the length of the target ablation zone 58. Due to the small diameter of the intercostal vein the reduced balloon size may risk contacting the transducer or getting over heated by the transducer, which may rupture the balloon or reduce efficacy of the ablation. To remedy this risk struts or protrusions 227 may be positioned between the transducer and balloon. The struts 227 may be for example polymer strands elastically pre-shaped to radially expand away from the transducers 224. To make a longer ablation to span the targeted ablation zone, multiple transducers may be incorporated (e.g., three 4 mm long transducers) and spaced apart with flexible gaps 228 between them to facilitate traversing the small bend radius from the azygos vein to intercostal vein. For example, shaft 225 may be a braid reinforced polyimide tube with an optional guidewire lumen 229 for delivery over a guidewire 79 and carry electrical conductors that energize the transducers 224. The ultrasound transducers 224 may be cylindrical for producing circumferential ablation around the target vein. Alternatively, the ultrasound transducers may be flat or hemicylindrical to produce an ablation that is a partial segment of the circumference of the vein and a radially identifiable radiopaque marker 230 may be positioned on the distal section allowing a user to orient the direction of ablation toward the patient's anterior where the GSN passes over the vein 55. Optionally, the ultrasound transducer may be configured to image as well as ablate and the imaging function may be used to assess nearby structures such as the lung, vertebra, ribs. Imaging ultrasound may be used to confirm the transducer is aiming toward the lung, which is the direction of the target GSN. Optionally, the shaft may have a flexible neck 231 within 10 mm proximal of the balloon 221 to allow the distal section to sit well in the intercostal vein.

In an alternative embodiment of an ultrasound ablation catheter, the catheter can be composed of an active ultrasound transducer and an inflatable reflector balloon, which may be on the same catheter or alternatively be on separate catheters. The reflector balloon may have an inflated diameter in a range of 2.5 to 4 mm and on its proximal surface have a shape such as a concave curvature that focuses reflected waves on to the target ablation zone. The reflector balloon is located distal to the transducer and is inserted in the narrower intercostal vein, while the ultrasound transducer remains in the larger azygos vein. The ultrasound transducer may be exposed to blood flow in the azygos vein or alternatively may be contained in a chamber in an inflatable balloon filled with coolant (e.g., circulating coolant such as sterile water or saline). The ultrasound energy is directed toward the distal reflector balloon and reflected and focused into tissue surrounding the splanchnic nerve. The advantage of this approach is that an active ultrasound transducer can be made larger and is not required to go through the sharp turn from azygos to intercostal vein. A second advantage is that several intercostal veins can be used to target ablation with the same catheter.

The catheter 220 may have a distal radiopaque marker 230 positioned distal to the ablation elements, for example distal to the balloon 221 and a proximal radiopaque marker positioned proximal to the ablation elements, for example proximal to the balloon. The distal and proximal radiopaque markers may be separated along the longitudinal axis of the shaft by a distance in a range of 5 mm to 25 mm (e.g., 10 mm to 15 mm).

FIGS. 8A to 10 illustrate exemplary ablation catheters. The ablation catheters in these examples includes an ablation element that includes first and second flexible coiled ablation electrodes that are axially spaced. It may be beneficial to have first and second electrodes rather than a single longer electrode to avoid a tendency of the single longer electrode to heat tissue mostly towards one end of the electrode. Having more than one electrode thus can help to create a long and consistent ablation in tissue. FIGS. 8A to 10 are thus examples of ablation catheters that can more consistently create a continuous ablation of the desired length, such as 10 mm to 25 mm, such as 15 mm to 25 mm, such as 15 mm to 20 mm.

An additional exemplary benefit of having first and second electrodes versus a single longer electrode is that only a single relatively shorter electrode may be energized rather than a single longer electrodes. This can be advantageous when the patient's anatomy requires or may benefit from making shorter ablations, such as if the azygos is right centered. In these cases, a longer single electrode may make it difficult or dangerous to safely ablate tissue while avoiding non-target structures. This is described in more detail elsewhere herein.

Additionally, FIGS. 8A to 10 illustrate ablation catheters that have first and second ablation elements axially separated by a gap or spacing. This gap is small enough (i.e., not too large) such that a continuous lesion is formed when energizing the first and second ablation elements, yet is large enough to avoid short circuiting.

Design features of distal sections of ablation catheters herein (e.g., FIGS. 8A to 10) thus provide exemplary benefits that allow the distal section to be advanced into position in an intercostal vein and reliably create a continuous ablation of at least 10 mm to 25 mm in length, while allowing shorter ablation sections if needed based on the patient's anatomy.

In some methods of use, the ablation energy is RF, and an energy delivery controller is adapted to deliver RF power in a range of 15 W to 50 W. In some embodiments, the controller is adapted to deliver RF power in a range of 15 W to 40 W, in a range of 15 W to 35 W, or in a range of 20 W to 35 W, such as about 25 W, about 30 W or about 35 W.

In some methods of use, energy is delivered over a period of time between 25 seconds and 120 seconds. For example, energy may be delivered for 90 seconds, for 100 seconds, for 110 second, or for 120 seconds, wherein for a portion (e.g., half) of the period of time energy, may be delivered to a first electrode and for the remainder (e.g., half) of the period energy may be delivered to a second electrode.

In some methods of use, an irrigation flow rate is from 10 mL/min to 50 mL/min, (e.g., 10 mL/min, 15 mL/min, 20 mL/min) during ablation. Optionally, flow rate may be changed automatically by the control algorithm in response to changes in measured temperature, impedance or phase. With devices and methods disclosed herein, the TSN may be ablated in a relatively safe manner, with minimal or reduced adverse effects (such as damage to the lungs or other nerves).

Some method of use embodiments herein may temporarily occlude blood flow and reduce an effect of vein collapse, thus advantageously avoiding challenges of a changing thermal and electrical environment during the heating process. Some method of use embodiments herein may ablate a nerve up to 5 mm from the target vessel. Some of the devices herein are dimensioned and configured for delivery and positioning in vasculature specified for ablating a target nerve (e.g., TSN, GSN).

Some of the devices herein may have one or more features that provides for a safe delivery to the target vessel.

Some of the devices and methods of use herein may safely deliver energy with temperature monitored energy delivery.

Some of the methods of use herein may generate a lesion capable of targeting a nerve up to 5 mm away from the target vessel and within a target region having a continuous lesion length from 5 mm to 25 mm, such as 10 mm to 25 mm, such as 15 mm to 20 mm, (e.g., 15 mm, 16 mm, 17 mm, 18 mm, 19 mm, 20 mm), with a single positioning and delivery of energy.

Some of the devices and methods herein are adapted to avoid risks of boiling, hot spots, or erratic energy delivery that could decrease ablation efficacy. Furthermore, some embodiments may include nerve stimulation to identify a target nerve or non-target nerve to confirm positioning prior to ablation, or to confirm technical success during or following ablation.

It may be preferred, but not required, that the methods of ablation create a continuous ablation zone (i.e., not having separate, discrete regions of ablated tissue that are not connected to each other). This ensures that the region of tissue where the target GSN nerve or GSN nerve root is likely to be located is most likely to be effectively ablated by the ablation energy. The continuous ablation zone may be circumferential, or less than circumferential.

Optionally, an ablation confirmation test can then be performed, for example, by delivering a nerve stimulation signal. Monitoring can be performed for a physiological response (e.g., splanchnic vasoconstriction, increased heart rate, increased blood pressure) to the ablation confirmation test. If the physiological response demonstrates that the first lesion did not provide a clinically significant amount of GSN blocking (e.g., by observing a lack of physiological response) then ablation energy can be delivered from the ablation catheter to create a second lesion in tissue up to 5 mm from the second intercostal vein. The distal section of the ablation catheter can be moved to a third intercostal vein that is superior to (e.g., superior and adjacent to) the second intercostal vein. The same or different ablation confirmation test can be performed, followed by another monitoring test. If the physiological response demonstrates that the first lesion and second lesion did not provide a clinically significant amount of GSN blocking (e.g., by observing a lack of physiological response) then ablation energy can be delivered from the ablation catheter to create a third lesion in tissue up to 5 mm from the third intercostal vein. Any of the ablation confirmation tests may comprise delivering a nerve stimulation signal from a stimulation electrode positioned on the distal section of the ablation catheter configured to generate an action potential in the thoracic splanchnic nerve. Alternatively or in addition to, the ablation confirmation test may comprise a leg raise test. Alternatively or in addition to, the ablation confirmation test may comprise adding fluid volume to the venous system. Alternatively or in addition to, the ablation confirmation test may comprise a hand-grip test. Alternatively or in addition to, the ablation confirmation test may comprise measuring venous compliance or capacitance.

In exemplary methods in which an ablation confirmation test includes a leg raise test, the method may comprise any of the following steps. Prior to ablation in the lowest intercostal vein, a baseline measurement may be obtained by raising the legs and measuring the change in central venous pressure and waiting for equilibration, that is a measure of the total venous compliance including the central veins and splanchnic bed. The legs can then be lowered, to allow equilibration so blood redistributes back to the legs. An ablation in the lowest intercostal vein (e.g. T11) can then be performed as set forth herein. The legs can then be raised, followed by waiting for equilibration and re-measure central venous pressure. A measurement can then be made to determine if there was an appropriate reduction in total venous compliance. If yes, then the GSN has successfully been ablated. If no, then an ablation in the next higher intercostal vein (e.g., T10) can be performed, as set forth herein. The measurement can be repeated. A determination can then be made to see if there was an appropriate reduction in total venous compliance. If yes, then the GSN has successfully been ablated. If no, then an ablation in the next higher intercostal vein (e.g., T9) can be performed.

In exemplary methods in which an ablation confirmation test comprises a hand-grip or other activity that increases sympathetic nervous system (SNS) outflow to the splanchnic bed may comprise the following steps. An ablation can be performed in a lowest intercostal vein (e.g., T11). Venous compliance can then be measured. A hand-grip can then be performed for a predetermined amount of time (e.g., 60 seconds). Venous compliance can then be remeasured. If there is no change in venous compliance, the initial ablation was sufficient to achieve a clinically significant outcome. If there still is a decrease in compliance, some of the SNS activity caused by the hand-grip is getting through. The ablation in the lowest intercostal vein was thus insufficient to achieve a clinically significant effect. An ablation in the next higher intercostal vein (e.g., T10) can then be performed. A hand grip test for a predetermined amount of time (e.g., 60 seconds) can be performed. Venous compliance can then be remeasured. If there is no change in compliance, the second ablation was sufficient. If there is a decrease in compliance, some of the SNS activity caused by the hand-grip is getting through, and the ablation in the next higher intercostal vein was thus insufficient to achieve a clinically significant effect. Ablation is the next higher intercostal vein (T9) can then be performed. The procedure is done at this point as ablation at a level higher than the 3rd lowest intercostal vein is not anticipated.

Energy Delivery Algorithms

One aspect of the disclosure herein is related to energy delivery algorithms that are adapted to be particularly suited for ablating tissue circumferentially around a narrow blood vessel such as an intercostal vein or other similar vessel to a depth of at least 5 mm and up to 10 mm and from an ablation catheter. The ablation catheter may be any of the catheter embodiments shown in FIGS. 1, 2, 8A, 8B, 8C, 8D, 8E, 9, 10, 21A and 21B, wherein the ablation catheter comprises first and second electrodes (e.g., two coiled electrodes each having a length in a range of 2.5 to 10 mm, preferably 5 to 8 mm, and an outer diameter in a range of about 1.5 to 3 mm, and a distance between the electrodes in a range of 0 to 5 mm).

Figure 19:
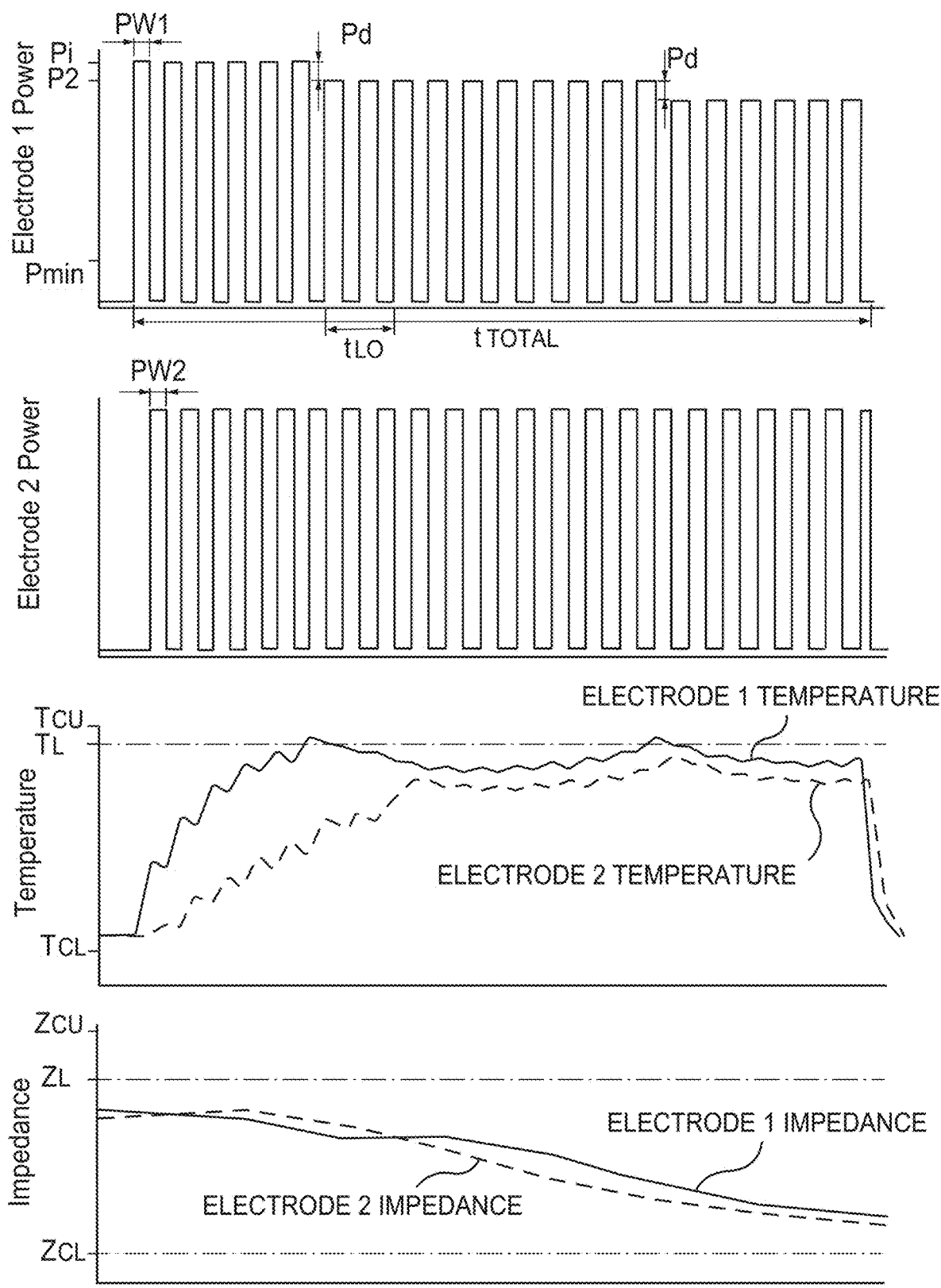
FIG. 19 includes plots of RF Power delivered to a first electrode and a second electrode as well as temperature monitored by sensors associated with the first and second electrodes and bioelectric impedance monitored from the first and second electrodes on the same time axis.

A first embodiment of an energy delivery algorithm is referred to as "Multiplexed Monopolar RF", wherein pulses of RF are delivered to the plurality (e.g., two) electrodes in monopolar configuration with asynchronous waveforms. Each electrode receives a pulsed waveform of RF energy alternating on and off at a steady frequency. The waveforms may be for example square wave, sinusoidal, or other form of alternating waveform. The on period delivers an ablative level of RF power while the off period delivers a non-ablative level of RF power (e.g., in a range of 0 W to 1 W, about 0.1 W). The waveforms for each electrode are asynchronous, that is to say the waveforms are aligned in time so that an on period for one electrode is aligned with off periods of the remaining electrode(s) and vice versa. The algorithm has an ablation mode initiated by user activation for example by depressing a button or foot pedal. The Ablation Mode Algorithm, as shown in FIG. 19, may include parameters that are optionally user defined or may be set by default until a user changes them or may be automatically defined. Note that FIG. 19 is not to scale and the total time, $t_{TOTAL}$ is shortened for a simplified illustration of the parameters and concepts. For example, if total time is 180 s and both the first and second electrode pulse widths are each 2 s, a true plot would show 45 cycles, however fewer cycles are shown for simplicity. The parameters may include Initial Power, $P_i$, First Electrode Pulse Width, PW1, Second Electrode Pulse Width, PW2, Total Therapy Time, $t_{TOTAL}$, Minimum Therapy Time, Lockout Period $t_{LO}$, Secondary Power $P_2$, and optionally further lower power levels. Initial Power, $P_i$, refers to the amplitude of radiofrequency power in Watts that is initially delivered to each of the ablation electrodes (e.g., the proximal 133 and distal electrodes 132 shown in FIGS. 8A, 8B, 8C, 8D, 8E, 9 and 10) at the beginning of the energy delivery protocol. Initial Power may be selectable in a range of 15 W to 50 W, preferably in a range of 20 W to 50 W, and may a have default setting of 35 W (e.g., when the flow rate is in a range of 10 to 50 ml/min). First Electrode Pulse Width, PW1, is the duration of each pulse of RF energy (i.e., ablative portion of waveform) delivered to the distal electrode 132 and may be selectable in a range of 0.5-4 s (e.g., 1-3 s, preferably 2 s) and have a default setting of preferably 2 s. Second Electrode Pulse Width, PW2, is the duration of each pulse of RF energy (i.e., ablative portion of waveform) delivered to the proximal electrode 133 and may be selectable in a range of 0.5-4 s (e.g., 1-3 s) and have a default setting of preferably 2 s. Some embodiments may have more than two electrodes and accordingly may have parameters of pulse width associated with each of them. The off period of an electrodes waveform may equal the duration of the on period(s) of the remaining electrode(s). In an embodiment having four electrodes, alternating electrodes (e.g., the first and third) may be synchronized together and asynchronous with the remaining electrodes (e.g., the second and fourth). The Total Therapy Time, $t_{TOTAL}$, is the duration of time from the beginning of delivery of ablative energy to the end and may be selectable in a range of 60 s to 400 s (e.g. 120 to 200 s), preferably 180 s. Minimum Therapy Time, is an optional portion of Total Therapy Time (e.g., less than or equal to) beginning at the start of delivery of ablative energy; if a temperature or impedance limit is reached before Minimum Therapy Time is complete then power may be decreased to the Secondary Power level or subsequent lower power level; if a temperature or impedance limit is reached after Minimum Therapy Time is complete then power may be decreased to zero (e.g., ablative energy delivery may be terminated). Lockout Period, $t_{LO}$, is a period of time following an event that triggers a reaction (e.g., a Temperature or Impedance Limit is passed, and the algorithm reacts by decreasing power) to allow tissue temperature to respond to the reaction (e.g., decrease in temperature). During a Lockout Period the algorithm may ignore the temperature or impedance measurements to either the electrode associated with the trigger, or all electrodes unless they are indicative of a critical error such as a critical upper temperature limit, $T_{CU}$, (e.g., 105° C. or higher), critical lower temperature limit, $T_{CL}$, (e.g., 20° C. or lower), critical upper impedance limit, $Z_{CU}$, (e.g., 800 or more Ohms, 900 or more Ohms, 1000 or more Ohms, a user selectable value between 800 and 2000 Ohms), or critical lower impedance limit (e.g., 50 Ohms or less) which may be indicative of damaged equipment. The Lockout Period may be selectable in a range of 2 s to 7 s, or alternatively the length of one pulse width up to the length of 4 pulse widths, and may have a default setting of 5 s. Secondary Power, P2, refers to the amplitude of radiofrequency power in Watts that is less than the Initial Power, for example 5 to 10 W less than the Initial Power. The power level is changed to Secondary Power if a Temperature, $T_L$, or Impedance Limit, $Z_L$ (e.g., in a range of 200 to 500 Ohms), is reached or passed, for the electrode (e.g., distal 132 or proximal 133 electrode) associated with the temperature sensor (e.g., distal 140 or proximal 139 temperature sensor) that sensed the Temperature Limit or with the electrode through which the Impedance Limit was measured. Alternatively, if one of the temperature sensors measures temperature above the Temperature Limit, $T_L$, power may be decreased to all of the electrodes. Optionally, algorithm parameters may include further power levels that are less than the Secondary Power, such as a Tertiary Power Level, Quaternary Power Level, and so on. Alternatively, a user defined parameter may be a Power Decrement, $P_d$, instead of Secondary Power. Power Decrement, $P_d$, is an amount of decrease in power amplitude triggered by an over temperature or over impedance limit and may be selectable in a range of 1 W to 30 W, with a default of 5 W. Optionally, the Power Decrement may be variable or be calculated as a percentage of the previous power level (e.g., a percentage in a range of 1% to 30%). In the event that Power is decreased, either to absolute levels such as Secondary Power or by Power Decrements, and a Minimum Power, $P_{min}$, (e.g., in a range of 1 to 10 W, e.g., 5 W) is reached and temperature is still above the Temperature Limit or impedance is still above the Impedance Limit, then the algorithm may react by a) terminating ablative power to the electrode associated with the trigger and continue to deliver ablative power to the remaining electrode(s) either using the current alternating waveform or in continuous RF, b) terminating ablative power to all electrodes, c) increase flow rate of the irrigation fluid, or d) adjust the Temperature Limit. If a treatment is terminated due to inability to maintain temperature below the Temperature Limit or impedance below the Impedance Limit or due to any other error, the user may be instructed by the algorithm to reposition the device, remove it for inspection, or inspect the equipment setup.

Saline may be pumped from an irrigation source through the catheter and out of irrigation ports 137 upon activation by a user. This may be done before the device is put in the patient to prime the irrigation lumen or test functionality or while the device is being advanced into position or during removal of the device and may facilitate delivery or removal, during which flow rate or pump speed may be selected by the user within a range of 0 to 50 mL/min. Optionally ablation will not start unless flow is on within a range of 15 to 30 ml/min.

Saline tracking is a feature that has an algorithm that calculates a volume of saline that has been delivered to the patient, for example, by multiplying flow rate and elapsed time or calculating the area under a plot of flowrate vs time, that saline has been delivered to the patient's vasculature using said flow rate and displaying the volume on a user interface (e.g., on the computerized console). Furthermore, the algorithm may determine if the portion of the catheter that delivers irrigation fluid is out of the body or in the body, either with a manual input or with an automatic detection algorithm using one or more input signals such as temperature sensed by temperature sensors on the catheter (e.g., sensor 139 or 140 in FIG. 8A), or monopolar impedance, or bipolar impedance. When the algorithm determines the catheter is in the patient's body (or in a delivery sheath that is inserted into the patient) any saline pumped by a pump connected to the computerized console will be accounted for in the calculation of saline volume delivered to the patient. When the algorithm determines the catheter is not in the patient's body, any saline pumped by the pump connected to the computerized console will not be accounted for in the calculation of saline volume delivered to the patient. This feature helps a user determine how much saline has been introduced to the patient's fluid system, which may be a concern for some patients. Optionally, a warning may be triggered if a predetermined saline volume has been reached or is approached. Saline irrigation flow rate may be turned on when the device is out of the body, for example to prime the irrigation lumen or to test the catheter and irrigation system function. To determine how much volume is delivered to the body the saline tracking algorithm may distinguish if the catheter is in or out of the body with manual input. This may be done by having the user press an actuator when the catheter is entered into the body that signals the algorithm to begin calculating volume when the pump is activated. If the catheter is removed from the body the user may press an actuator to signal the algorithm that the catheter is not in the body wherein calculation of accumulating saline volume is paused. Any volume delivered outside of the body is not included in the calculation of saline volume delivered to this patient. If the catheter or other catheter is put back in the patient for subsequent treatments any saline delivered to the patient is added to the volume calculation by the user restarting tracking by pressing an actuator. Alternatively, the saline tracking algorithm may automatically identify if the irrigated ablation catheter is in the body or not by monitoring monopolar impedance measured between one or more ablation electrodes and the grounding pad, or alternatively monitoring bipolar impedance measured between two ablation electrodes. Monopolar impedance has an advantage over bipolar impedance for detecting in vivo vs ex vivo because monopolar impedance completes an electrical circuit from at least one of the electrodes on the catheter through the body to a dispersive grounding pad placed on the patient's skin, whereas bipolar impedance completes a circuit from a first electrode on the catheter through a conductive medium to a second electrode on the catheter. The conductive medium may be within the patient such as blood or tissue but it also could include saline or a conductive medium outside the body, for example if the electrodes are immersed in a saline bath or if saline is irrigated through the catheter and wets the electrodes closing the circuit. However, bipolar impedance could still be used to detect a change in environment and be useful in a saline tracking algorithm. A very low (non-ablative, e.g., 0.1 W) power may be delivered when an ablation treatment is not running so impedance can be measured. For example in monopolar mode, if the catheter is in the body and connected to the console and a grounding pad in electrical communication with the console is connected to the patient's skin, monopolar impedance may be within a certain range that is discernable from a catheter out of the body. For example, as determined experientially, a monopolar impedance measurement within a range of 700-900 Ohms in monopolar mode may indicate the distal region of the catheter having the electrodes and irrigation holes is in a sheath in the patient's vasculature; an impedance measurement that is a significant drop from the sheathed impedance, for example in a range of 80 to 130 Ohms, may indicate the distal region is in the vasculature and out of the sheath; above a high impedance threshold (e.g., a high impedance threshold or 900 Ohms, higher than 2000 Ohms, higher than 3000 Ohms) in monopolar mode may indicate the electrodes are out of the body, or that a grounding pad is incorrectly connected. Alternatively, bipolar impedance (e.g., measured by passing current through conductive medium between two ablation electrodes on the distal region of the catheter) measured in a range of about 300 to 600 Ohms (e.g., about 500 Ohms) may indicate the distal region is in a sheath and in the body; or a bipolar impedance in a range of 60 to 80 Ohms may indicate the distal region is in the vasculature out of the sheath; a high impedance threshold (e.g., higher than 600 Ohms, higher than 900 Ohms, higher than 2000 Ohms, higher than 3000 Ohms) may indicate the electrodes are out of the body, or that the catheter's electrical circuit has been broken. The algorithm may determine that the distal region of the ablation catheter, where saline is released, is in the body if measured impedance is below the high impedance threshold, wherein accumulating saline volume is accounted for; and that the distal region is out of the body if measured impedance is above the high impedance threshold, wherein saline pumped during this scenario is not accounted for in the accumulated volume. Optionally, when a change of in vivo/ex vivo state has been detected the algorithm may display a message asking the user to acknowledge the change. Optionally, a user may input a known volume of saline that has been injected by other means such as with a contrast solution injected from a syringe into the delivery sheath and the known volume may be added to the accumulated volume calculation.

Figure 20:
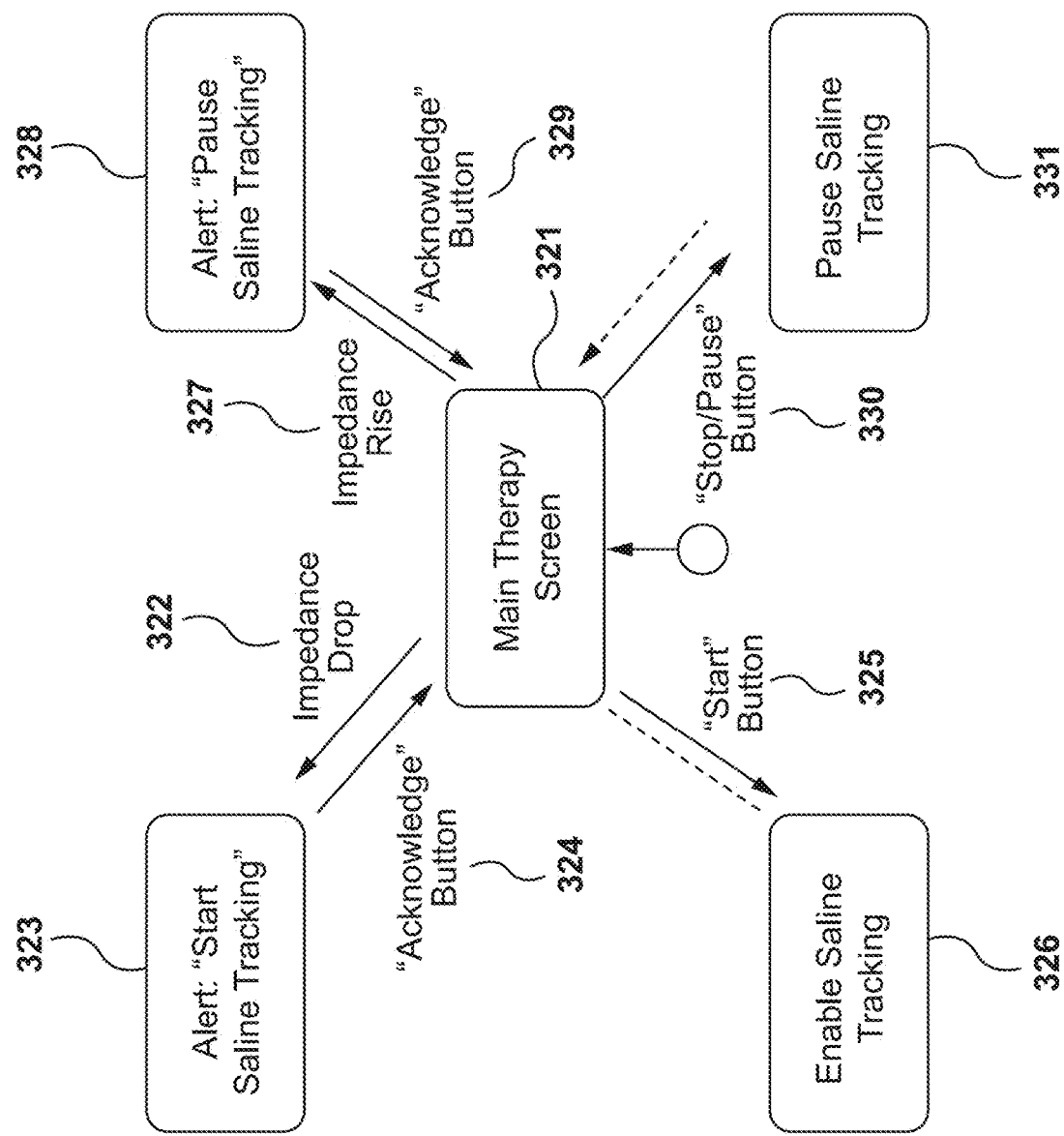
FIG. 20 is an exemplary machine state diagram of an exemplary saline tracking algorithm.

FIG. 20 shows a machine state diagram of an automatic saline tracking algorithm. Beginning at a Main Therapy Screen 321 with the ablation catheter connected to the console and out of the body and a grounding pad connected to the patient and console a user may press a button 325 to enable saline tracking 326. This may begin automatic calculation of saline volume pumped wherein the calculation determines how much of the volume of saline is deposited in the body and optionally how much is pumped while the catheter is out of the body. If the ablation catheter is inserted into the body the bioelectric impedance should drop 322 to within the range indicating tissue contact and a message is displayed suggesting that the user start saline tracking 323. The user may press a button to acknowledge 324 the message which tells the algorithm to include the accumulating pumped saline to the total accumulated volume of saline deposited in the body. If the catheter is removed from the body an impedance rise to a level out of the range associated with body contact is measured 327 and a message is automatically displayed to suggest the user Pause saline tracking 328. The user may press a button to acknowledge 329 the message which tells the algorithm to exclude the accumulating pumped saline to the total accumulated volume of saline deposited in the body. Furthermore, a user may press a button 330 at any time to pause saline tracking, or to pause including the pumped saline volume in the calculation of saline deposited into the body 331. Alternatively, instead of automatically defining that the catheter is in the body based on impedance, an algorithm may alert the user that it thinks the catheter is out of the body and the user may manually select that flow shall be excluded from the saline tracking total. A reset actuator may be pressed by a user to reset the total volume to zero.

An alternative saline tracking algorithm may ignore a quick increase in impedance within a predetermined amount that may be caused by the injection of contrast solution or saline in the vicinity of the ablation electrode(s) while the catheter is in the body to avoid a false determination of removal. To distinguish the difference between injecting contrast solution or saline and removing or inserting the distal region of the catheter from the patient, when a large change in impedance is detected, the algorithm may have two impedance thresholds that are used depending on whether the system is in in vivo or ex vivo mode. A first impedance threshold (e.g., in a range of 400 Ohms to 600 Ohms, about 500 Ohms) may be used if the catheter is not in the patient's body (i.e., ex vivo) to automatically indicate that the catheter has been inserted into the body when impedance drops below this first threshold. A second impedance threshold (e.g., in a range of 800 Ohms to 3000 Ohms, about 900 Ohms) may be used if the catheter is in the patient's body (i.e., in vivo) to automatically indicate that the catheter has been removed from the body when impedance rises above this second impedance threshold. For example, the ablation catheter may be out of the patient and impedance may be above the second threshold, say 900 Ohms; if the saline pump is running the algorithm determines that the catheter is not in the body and no saline volume is included in an accumulation calculation; the catheter may be inserted into the patient and impedance may drop below the first threshold, say 500 Ohms, wherein the algorithm determines the catheter is in the body and any pump movement is accounted for in the accumulation calculation; injection of saline or contrast may raise impedance above the first threshold but since the catheter is in the body the algorithm determines the rise does not indicate removal so any pump movement continues to be accounted for in the accumulation calculation; if the catheter is removed from the body impedance will rise above the second threshold, say 900 Ohms, and the tracking algorithm will determine the catheter has been removed and any pump movement will not be accounted for in the accumulation calculation. Optionally, the first and second thresholds may be adjusted or selected in user settings. The catheter may be indicated for use with a consistent concentration of saline, for example 0.90 Normal Saline, for the algorithm to function properly.

In addition to calculating accumulated saline injected, the algorithm may optionally change other feature behaviors depending on whether the system is in the in vivo or ex vivo mode, for example as described in Table 1.

TABLE 1

| Feature | In vivo behavior | Ex vivo behavior |
| --- | --- | --- |
| Saline volume tracking | active | paused |
| Require confirmation to stop pump | enabled | disabled |
| Remind user to turn on pump if not running | Triggered upon entry to in vivo mode | n/a |
| Remind user Pump Prime not completed since last power cycle | Triggered upon entry to in vivo mode | n/a |
| Require confirmation to run Prime | In vivo Warning | Message |
| Notify user that pump is still running | n/a | Triggered upon entry to ex vivo mode |

TABLE 1-continued

| Feature | In vivo behavior | Ex vivo behavior |
| --- | --- | --- |
| RF energy delivery | Allowed | Restricted |
| Prime Mode (bypass pump bubble detector) | Restricted | Allowed |

Another use of bipolar impedance monitoring by an algorithm may be used to display a message to the user to check if the dispersive grounding pad is not correctly connected if bipolar impedance is low (e.g., less than 500 Ohms) and monopolar impedance is high (e.g., above 900 Ohms).

Another use of bipolar impedance monitoring by an algorithm may be used to display a message to the user to check if there is an open circuit on one or both electrodes, if bipolar impedance is high (e.g., above 900 Ohms), and the irrigation pump is running, and the system is in in vivo mode.

During the Ablation Mode Algorithm, the pump may be activated so saline is irrigated from irrigation ports 137 with a flowrate in a range of 15 to 30 ml/min before ablation energy begins to be delivered, for example for a time of 5 s. Then radiofrequency electrical energy (RF), for example having a frequency in a range of 350 to 500 kHz, is delivered from the computerized energy console to a first of the plurality of electrodes (e.g., the distal electrode 132) in monopolar mode (i.e., returned through a grounding pad) with the Initial Power for a duration of a pulse width (e.g., the First Electrode Pulse Width). Then the first electrode (e.g., distal electrode) enters its off period of the waveform (e.g., having a power of 0 W or a low power less than 1 W) while RF is delivered to a second electrode (e.g., the proximal electrode) starting at the Initial Power for a duration of the Second Electrode Pulse Width. Optionally, if the ablation device has more than two electrodes power may be then delivered to the subsequent electrode(s) for an according pulse width before repeating power delivery to the first electrode. Alternatively, power may be delivered to the electrodes in other orders or combinations without deviating from the spirit of the disclosure herein. RF power continues to be multiplexed through each electrode for the Total Therapy Time unless an event is triggered that titrates or stops delivery of ablative RF.

Throughout the Ablation Mode Algorithm and optionally before or after, temperature may be measured by the temperature sensors (140 and 139 in FIGS. 8A, 8B, 9, and 10) and displayed on the console. During the Ablation Mode Algorithm these temperatures may be compared to a predefined Temperature Limit, $T_L$, which may be in a range of 40° C. to 95° C., preferably 90° C. Since the space in the vessel around the electrodes and temperature sensors is irrigated the measured temperatures can be expected to be less than the hottest tissue temperature. Due to the variability of vessel size and shape the relationship between measured temperature and the hottest tissue temperature or ablation volume may vary. However, a measured temperature that is higher than the Temperature Limit may be an indication of too much power. The Temperature Limit may be considered as a safety control where measured temperature above the limit needs to be reduced. However, if measured temperature is below the limit it is not necessarily an indication of low tissue temperature. If the measured temperatures are below the Temperature Limit throughout the Total Therapy Time then RF Power remains at the Initial Power. If one of the measured temperatures is above or optionally equal to the Temperature Limit, $T_L$, during treatment (total therapy time) $t_{TOTAL}$, or optionally before Minimum Therapy Time is complete, then power may be decreased to the Secondary Power, P2, preferably for the active electrode as shown in FIG. 19, or alternatively for the electrode associated with said measured temperature or all electrodes. The measured temperature is expected to drop below the Temperature Limit within about 5 seconds (or about 2 to 3 pulse widths) of the power decrease, however if it does not or if it does but then raises to or above the Temperature Limit again prior to completion of the Total Therapy Time (or optionally the minimum therapy time) then power may be decreased to 0 W or a low level less than 1 W preferably to all electrodes, or alternatively to the active electrode or the electrode associated with the measured temperature. Alternatively, power may be decreased to the Tertiary Power and so on. Following completion of the Minimum Therapy Time if any of the measured temperatures reaches or exceeds the Temperature Limit then power may be decreased to 0 W or a low level less than 1 W instead of titrating power to a lower ablative level.

Optionally, the Ablation Mode Algorithm may further have an Impedance Limit, $Z_L$, which may be in a range of 200 to 500 ohms, preferably 500, which may be an indication of tissue desiccation. If monopolar impedance measured from one of the plurality of electrodes in electrical communication with the grounding pad, rises above the Impedance Limit delivery of ablative energy to the associated electrode may terminated to avoid steam formation or injury. Optionally or additionally, if an Impedance Limit is passed before minimal therapy time is complete then power of the ablative RF energy may be reduced to the Secondary Power or optionally other lower power levels if there are subsequent occurrences. As shown in FIG. 19, if impedance for all electrodes remains below the Impedance Limit, $Z_L$, and above a Critical Low Impedance Limit, $Z_{CL}$, then there are no resulting changes to power for each electrode.

Optionally, if temperature or impedance for a particular electrode goes above the Temperature Limit or Impedance Limit when the secondary power is being delivered then ablative RF power may drop to 0 W preferably for the active electrode, or alternatively for the electrode associated with the sensor or for all electrodes.

Optionally, the Total Therapy Time or Minimum Therapy Time (if included) may be extended if power has been decreased to the Secondary Power, or optional subsequent lower power levels, for example match the amount of energy being delivered if power were not decreased.

In addition to the Temperature and Impedance Limits the algorithm may have an Upper Critical Temperature Limit, $T_{CU}$, Lower Critical Temperature Limit, $T_{CL}$, Upper Critical Impedance Limit, $Z_{CU}$ and Lower Critical Impedance Limit, $Z_{CL}$. An Upper Critical Temperature Limit, $T_{CU}$, may be used to identify a damaged temperature sensor or an ultimately high tissue temperature above which is not desirable, and may be equal to or above 105° C. A Lower Critical Temperature Limit, $T_{CL}$, may indicate something is incorrect about placement or device damage and may be equal to or below body temperature (e.g., 35° C.). An Upper Critical Impedance Limit, $Z_{CU}$, may be used to identify damage to the catheter such as broken wires or improperly applied ground pad and may be in a range of 800 to 2000 Ohms. A Lower Critical Impedance Limit, $Z_{CL}$, may be used to identify damage to the catheter such as short circuit or a damaged electrode and may be equal to or below 20 Ohms.

Optionally, an energy delivery algorithm may have a bipolar RF component where RF electrical current passes from the first electrode to the second electrode (bipolar mode). Bipolar RF concentrates current density between the two electrodes which may result in an ablation pattern that heats tissue between the electrodes greater than the two electrodes delivering monopolar RF independently from one another. A bipolar RF component may be added to the beginning or end of a Multiplexed Monopolar RF period. For example, a bipolar RF component may have a duration in a range of 30 s to 120 s, preferably about 60 s, and deliver power at an initial level in a range of 10 to 50 W (e.g., 20 to 35 W, preferably about 30 W) and be delivered either before or after a multiplexed monopolar RF treatment.

Alternatively and optionally, an ablation waveform may be similar to the Multiplexed Monopolar RF algorithm but have an additional pulse width wherein the electrodes deliver Bipolar RF. For example, a bipolar pulse width may be in a range of 0.5 to 5 s (e.g., 2 s). The waveform may have an alternating cycle of monopolar RF from a first electrode for a first pulse width, monopolar RF from a second electrode for a second pulse width, and bipolar RF between the first and second electrodes for a bipolar pulse width that repeats. If the ablation catheter has more than two electrodes the waveform may include a repeating cycle of monopolar RF to each electrode for respective pulse widths and bipolar RF between each adjacent pair of electrodes for bipolar pulse widths.

An alternative embodiment of an Ablation Energy Delivery Algorithm used to create a desired lesion for GSN ablation, is referred to as "Sequential Monopolar with Bipolar Fill", wherein ablative RF energy is delivered in monopolar mode to a first ablation electrode (e.g., the distal electrode 132 shown in FIGS. 1, 2, 8A, 8B, 9, and 10) for a First Electrode Monopolor Duration, then to a second ablation electrode (e.g., the proximal electrode 133) for a Second Electrode Monopolar Duration, then ablative RF energy is delivered in bipolar mode between the first and second electrodes for a Bipolar Duration and with an Initial Bipolar Power. If temperature measured by a temperature sensor associated with the electrode receiving ablation energy raises above an Upper Monopolar Temperature Limit the Initial Monopolar Power of RF energy may be decreased to a Secondary Monopolar Power or alternatively be decreased by a Power Decrement. If the temperature rises above the upper Temperature Limit again while the lower power is being delivered then the power may be decreased again, either to a Tertiary Power or by the Power Decrement. Optionally, a user may define parameters such as Initial Power to each ablation electrode, First and Second Electrode Monopolor Durations, Power Decrement or Secondary, Tertiary etc Monopolor Power. Likewise, during the Bipolar phase the Initial Bipolar Power may be decreased to a Secondary Bipolar Power or by a Power Decrement if measured temperature from either of the temperature sensors associated with the activated electrodes rises above an Upper Bipolar Temperature Limit.

Initial Monopolar Power is the amplitude of RF power that is initially delivered to either ablation electrode during the monopolar phases and may be selectable in a range of 20 W to 50 W, with a default setting of 25 W.

First Electrode Monopolor Duration is the amount of time that ablative RF energy is delivered to the first electrode in Monopolar mode and may be selectable in a range of 30 s to 180 s, with a default setting of 60 s.

Second Electrode Monopolor Duration is the amount of time that ablative RF energy is delivered to the second electrode in Monopolar mode and may be selectable in a range of 30 s to 180 s, with a default setting of 60 s.

Secondary Monopolar Power is the amplitude of RF power that is lower than the Initial Monopolar Power, triggered by measured temperature rising above the Upper Temperature Limit. It may be selectable in a range of 10 W to 50 W, as long as it is below the Initial Monopolar Power, with a default setting of 20 W.

Monopolar Power Decrement, an alternative to Secondary Monopolar Power (and optionally Tertiary etc.), is the amount of decrease in Power triggered by measured temperature rising above the Upper Monopolar Temperature Limit and may be selectable in a range of 1 to 20 W, with a default setting of 5 W.

Initial Bipolar Power is the amplitude of RF power that is initially delivered to two ablation electrodes (e.g., the two electrodes that were previously activated with monopolar RF) during the bipolar phase and may be selectable in a range of 10 W to 50 W, with a default setting of 20 W.

Bipolar Duration is the amount of time that ablative RF energy is delivered to the two electrodes in Bipolar mode and may be selectable in a range of 10 s to 180 s, with a default setting of 20 s.

Secondary Bipolar Power is the amplitude of RF power that is lower than the Initial Bipolar Power, triggered by measured temperature rising above the Upper Bipolar Temperature Limit. It may be selectable in a range of 5 W to 50 W, as long as it is below the Initial Bipolar Power, with a default setting of 15 W.

Bipolar Power Decrement, an alternative to Secondary Bipolar Power (and optionally Tertiary etc.), is the amount of decrease in Power triggered by measured temperature rising above the Upper Bipolar Temperature Limit and may be selectable in a range of 1 to 20 W, with a default setting of 5 W.

Upper Monopolar Temperature Limit is a threshold temperature that measured monopolar temperature is compared to during a monopolar phase. It may be selectable within a range of 60 to 90° C., with a default setting of 90° C.

Upper Bipolar Temperature Limit is a threshold temperature that measured bipolar temperature is compared to. It may be selectable within a range of 60 to 90° C., with a default setting of 90° C.

Optionally, if an Upper Temperature Limit is passed during either a monopolar or bipolar phase Initial Power may be decreased to the Secondary Power or by the Power Decrement and the Duration may be repeated, optionally with the electrodes in the same position. If the Upper Temperature Limit is passed a subsequent time the therapy may be terminated with an error message. The user may attempt an ablation procedure with the electrodes repositioned or with a new catheter.

Optionally, the algorithm may have an Upper Monopolar Impedance Limit, which is a threshold impedance that measured monopolar impedance is compared to during a monopolar phase. It may be selectable within a range of 150 to 300 Ohms, with a default setting of 200 Ohms.

Optionally, the algorithm may have an Upper Bipolar Impedance Limit, which is a threshold impedance that measured bipolar impedance is compared to during the bipolar phase. It may be selectable within a range of 100 to 300 Ohms, with a default setting of 150 Ohms.

The disclosure that follows provides some exemplary methods of use and steps thereof. Some embodiments of a method of use may include one or more of the following steps, the order of which may in some instances be varied, and not all steps of which need necessarily be performed.

Methods herein may include interventional access, which may include one or more of the following treat the patient with an anti-coagulation regimen that is appropriate for venous interventional procedures; place a return electrode on the patient's right chest; follow standard techniques for femoral, subclavian, or jugular vein puncture, guide wire insertion, and sheath placement using heparinized saline where appropriate; place 0.035 exchange length guide wire (e.g., Cordis Ampath Super Stiff 260 cm or equivalent); advance a 6 F general purpose catheter (e.g. JR4 or equivalent) over the guide wire to the azygous vein ostium; using the 6 F general purpose catheter, inject a bolus of radiopaque contrast to identify the azygos vein ostium using fluoroscopy; engage the azygos vein ostium with the guide wire and 6 F general purpose catheter and advance the guide wire through the valve (if applicable) into the azygos vein; exchange the 6 F general purpose catheter for an azygos access sheath, wherein the azygos access sheath may be 9 F and at least 100 cm long (e.g., Arrow 9 F Super Arrow Flex Introducer Sheath or equivalent); position the azygos access sheath approximately to the T9 level; adjust the C-arm off the vertical axis to obtain the optimal view of the azygos vein tree via shooting contrast prior to introduction of the Ablation Catheter; load a 0.014 exchange length guide wire (e.g. ChoICE Pt LS Floppy or equivalent) into the azygos access sheath; and advance the 0.014 guide wire and deep seat into first target intercostal vein (e.g., T11 intercostal vein).

Methods herein may include device, generator, and accessory preparation, which may include one or more of the following steps: inspect the catheter package prior to use; open the Ablation Catheter package using sterile technique; while maintaining sterility, remove the Catheter from its package and place in a sterile field; visually inspect the electrodes and ablation catheter carefully for integrity and overall condition; fill a 10 cc or larger syringe with saline and connect the syringe to the guidewire lumen hub on the handle of the ablation catheter. Flush the guidewire lumen with the saline to remove all air; prepare the ablation catheter by connecting the ablation catheter irrigation line to a 3-way stopcock, connecting the tube set to the 3-way stopcock and connecting the saline spike on a hanging sterile saline bag, and ensuring the stopcocks on the saline inlet and saline outlet lines are in the open position; place the irrigation pump tubing into the pump, through the bubble detectors and close the pump door; power ON the Generator (also referred to as a computerize console) and initialize the pump; flush the irrigation lumen of the ablation catheter using the pump to pump the saline through the irrigation lumen; confirm that the irrigation ports are patent; purge the tubing and ablation catheter of air bubbles; watch the saline tubing and Catheter tip for bubbles and continue to de-bubble until there is no air in the ablation catheter irrigation lumen and tube set; to avoid occlusion of the irrigation conduits and prevent ingress of air into the ablation catheter, the ablation catheter may be continuously irrigated when within the vasculature, for example at a rate 2 mL/min; irrigation may only be stopped after removal of the ablation catheter from the body; confirm user selectable ablation parameters on the Generator; plug the ablation catheter with a cable into the RF Generator; observe connector polarity;

Methods herein may include Ablation Catheter Insertion and Ablation Energy Delivery, which may include one or more of the following steps: with the 0.014 guide wire deep seated in the first target intercostal vein, advance the ablation catheter over the guide wire into the intercostal vein; initiate saline tracking (examples of which are set forth herein) from the Generator once the ablation catheter is inserted into the patient; the ablation catheter may be passed from a peripheral vessel to the desired position with the aid of fluoroscopy; the ablation catheter saline infusion rate may be increased to a maximum of 50 mL/min to assist with device entry to the target intercostal vein; place the proximal marker at the anterior midline of the vertebrae in the AP view (if possible); if the azygos to intercostal vein ostium is to the patient's right of midline, advance the device so the proximal radiopaque marker is in the azygos vein proximal to the ostium to the intercostal vein and approximately at the patient's midline; rotate the C-arm to RAO30 (or an appropriate angle that maximizes the projected length between the proximal and distal radiopaque markers) and confirm that the distal marker is not past the costovertebral joint, and adjust as appropriate; confirm that a valid impedance reading (e.g., within 80 to 150 Ohms in monopolar mode, or within 60 to 80 Ohms in bipolar mode) is displayed for both electrodes on the Generator; activate a saline infusion rate of 15 ml/min to 30 ml/min before initiating ablative energy delivery; a recommended saline infusion rate during ablation may be 15 ml/min; The saline infusion rate can be adjusted after initiation of RF delivery to within 15 ml/min to 30 ml/min; initiate the RF ablation mode algorithm from the Generator; monitor the impedance display on the RF Generator, before, during, and after RF power delivery; if a sudden rise in impedance is noted during RF delivery that does not exceed the preset limit, manually discontinue the power delivery; clinically assess the situation; if necessary, remove the ablation catheter and inspect it for damage; in case of a steam pop or automatic shut off, discontinue RF and remove the ablation catheter, terminate saline tracking from the RF Generator and perform a visual inspection, checking for coagulum, charring, or other catheter defects; confirm saline infusion rate and flush the ports prior to reinsertion in the patient, resuming saline tracking once inserted; if the ablation catheter has defects, exchange it for a new one; re-position the ablation catheter and attempt another RF application; optionally, no more than two 180 s RF applications should be completed at a single target site; if the pump alarms and stops the irrigation, immediately remove the Catheter from the patient and inspect and re-flush the ablation catheter; when the ablation in the first target intercostal vein (e.g., T11) is finished, remove the guide wire and ablation catheter from the first target intercostal vein and keep in the azygos access sheath in place; the ablation catheter saline infusion rate may be increased to a maximum of 50 cc/min to assist with device removal from the target intercostal vein; the ablation catheter may be removed for inspection; deliver contrast agent to visualize a second target intercostal vein (e.g., T10) from the azygos access sheath; repeat Ablation Catheter Insertion and Ablation Energy Delivery steps to advance the ablation catheter over the guide wire into the second target intercostal vein and ablate; when the ablation in the second target intercostal vein is finished, withdraw the ablation catheter into the 9 F azygos access sheath and deliver contrast from the azygos access sheath to obtain a fluoroscopic image of the azygos tree.

Methods herein include device withdrawal, which may include one or more of the following steps: withdraw the ablation catheter into the 9 F azygos access sheath and out of the patient; terminate saline tracking; it may be helpful to disconnect the connector cable; inspect the ablation catheter; withdraw the azygos sheath from the patient and close the venous puncture; after use, dispose of the devices in accordance with hospital, administrative, and/or local governmental policy.

In any of the methods herein, including ablation confirmation tests herein, not all of the steps need necessarily to be performed. And some of the steps may occur in different orders. It is of note that the procedures herein are intending to target particular nerves or nerve roots, and are doing so from particular target veins, and even within those veins are placing ablation elements or members within certain regions. The anatomical regions that are being accessed and targeted necessitate certain design requirements. In other treatments that are targeting different anatomical locations for placement, and targeting different target nerves, the device design constraints for those approaches are very different, and thus the devices that can be used in those treatments may be very different. The disclosure herein thus provides specific reasons for designing particular devices, and those reasons include being able to effectively carry out the treatments specifically set forth herein.

While the above description provides examples of one or more processes or apparatuses, it will be appreciated that other processes or apparatuses may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

Specific embodiments described herein are not intended to limit any claim and any claim may cover processes or apparatuses that differ from those described below, unless specifically indicated otherwise. The claims are not limited to apparatuses or processes having all of the features of any one apparatus or process described below or to features common to multiple or all of the apparatuses described below, unless specifically indicated otherwise. It is possible that an apparatus or process described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Additional Examples

A first additional example is a method of characterizing the position of a patient's azygos vein relative to a portion of the patient's spine, comprising: while imaging at least a portion of the patient's spine; intravascularly delivering a device into a patient's azygos vein; performing at least one of: injecting a radiopaque contrast agent (e.g., dye) from the device into the patient's vasculature (e.g., into the azygos vein and/or one or more intercostal veins) to visualize the vasculature relative to a position of the spine, or identifying the position of at least a portion of the device relative to a portion of the spine, to thereby characterize (e.g., qualify and/or quantify) the position of the patient's azygos vein relative to a portion of the spine (e.g. relative to a midline of the spine).

In this first additional example, imaging may comprise imaging in an anterior-to-posterior view.

This first additional example may further comprise determining a lateral position of a patient's azygos vein, where it meets an intercostal vein, relative to the patient's spine. Determining a lateral position of the patient's azygos vein may be performed while imaging the patient's azygos vein. Imaging may comprise radiographic imaging (e.g. fluoroscopy) after injecting a radiopaque contrast agent (e.g., dye) from the device into the patient's vasculature. Determining a lateral position may be used to determine where to place an ablation catheter relative to the intercostal vein, as part of an ablation procedure (optionally to ablate a GSN).

A second additional example is a method that includes assessing a position of a patient's azygos vein to determine if it is centered, right-biased (to the patient's right of center), or left-biased (to the patient's left of center). Assessing a position of the patient's azygos vein may be performed while imaging the patient's azygos vein. Imaging may comprise radiographic imaging (e.g., fluoroscopy). Imaging may comprise imaging in an anterior-to-posterior view. Assessing the position may be used to determine where to place an ablation catheter as part of an ablation procedure (optionally intended to ablate a GSN).

In this second additional example, an assessing step can be used to determine where to place a radiopaque marker of an ablation catheter (optionally a proximal radiopaque marker), wherein the ablation catheter includes an ablation element distal to the radiopaque marker.

In this second additional example, the assessing step is used to determine whether to place the radiopaque marker at an ostium where the azygos vein meets an intercostal vein, or at (including substantially at) a midline of the spine.

In this second additional example, if an assessing step indicates that the azygos vein is right-biased or centered (including substantially centered), the method may include positioning the radiopaque marker at an ostium where the azygos vein meets the intercostal vein.

In this second additional example, if the assessing step indicates that the azygos vein is left-biased, the method may include positioning the radiopaque marker at or substantially at a midline of the spine (for example, as determined in an anterior-to-posterior imaging view).

In this second additional example, the assessing step may be used to determine where to place an ablation element (e.g., one or more electrodes) that is part of the ablation catheter.

In this second additional example, the method may further comprise assessing a position of a distal radiopaque marker relative to at least one or more of a portion of the spine, a rib, or a costovertebral joint. The method may further comprise retracting the ablation catheter proximally if the assessment indicates that the distal radiopaque marker is positioned too far distally, which thereby indicates the ablation element is positioned too far distally. The method may further ensure that the distal radiopaque marker is not further distally than the costovertebral joint.

A third additional example is a method of intravascularly positioning an ablation catheter for GSN ablation, comprising: positioning an ablation catheter in one or more of an intercostal vein (e.g. T9, T10, or T11) and an azygos vein, wherein the position of the ablation catheter is selected based on a characterized relative position of a portion of the spine and a location of the azygos vein where it meets the intercostal vein.

A fourth additional example is a method of characterizing a position of a distal section of an ablation catheter to facilitate placement of at least a portion of the ablation catheter in an intercostal vein, comprising: positioning an ablation catheter in a patient's intercostal vein (e.g. a T9, T10, or T11 intercostal vein); while imaging a portion of the patient that includes the intercostal vein and a portion of the spine, determining a location of one or more components of the ablation catheter relative to one or more of a portion of the spine, a rib, or a costovertebral joint.

A fifth additional example is a method of any claim herein, comprising accessing venous vasculature at the patient's jugular vein or femoral vein with an access introducer sheath (e.g. 12 F).

A sixth additional example is a method of any claim herein, comprising delivering a delivery sheath (e.g., 9 F sheath) to an azygos vein (e.g., to one or two thoracic levels above the target intercostal).

A seventh additional example is a method of any claim herein, comprising delivering contrast agent to show a location of an azygos vein and one or more intercostal veins while imaging the azygos vein and one or more intercostal vein.

Any of additional examples may include an imaging step that comprises imaging in an anterior-to-posterior direction (e.g., with a C-arm in an AP position).

Any of additional examples may include positioning a C-arm in a Right Anterior Oblique angle.

Any of additional examples may include positioning a C-arm in a range of 20 degrees to 70 degrees, such as 30 to 60 degrees.

Any of additional examples may include positioning a C-arm at an angle that maximizes a projected distance between first and second axially spaced locations on the ablation catheter (e.g., locations of proximal and distal radiopaque markers).

Any of additional examples may include assessing if a RO marker (e.g., a distal RO marker) is at or proximal to a particular anatomical location (e.g. a costovertebral joint).

Any of additional examples may include, if the marker is at or proximal to the particular anatomical location, continuing with an ablation procedure (e.g. ablating tissue). If the marker is not at or proximal to the particular anatomical location, the method may include moving the ablation catheter within the intercostal vein. If the marker is not at or proximal to the particular anatomical location, the method may include generating ablative energy within a proximal ablation element (e.g. coiled electrode) but not with a distal ablation element (e.g. coiled electrode).

An eighth additional example is an ablation catheter sized and configured such that a distal section of the ablation catheter can be advanced into a T9, T10, or T11 intercostal vein from an azygos vein, and adapted to deliver ablative energy, comprising: an elongate shaft with a length such that a distal section of the catheter can be positioned in a T9, T10, or T11 intercostal vein; and the distal section comprising an electrically conductive flexible ablation element carried by the elongate shaft, the electrically conductive flexible ablation element (which may comprise more than one ablation element) having a length from 5 mm-20 mm, and the distal section having an OD (at least in a delivery configuration) from 1.5 mm-3 mm.

A ninth additional example is an ablation catheter sized and configured such that a distal section of the ablation catheter can be advanced into a T9, T10, or T11 intercostal vein from an azygos vein, and adapted to deliver ablative energy, comprising: an elongate shaft with a length such that a distal section of the catheter can be positioned in a T9, T10, or T11 intercostal vein; and the distal section comprising an electrically conductive flexible ablation element carried by the elongate shaft.

In this ninth additional example, the ablation element may comprise a first ablation element axially spaced from a second ablation element, the first and second ablation elements carried by the shaft. The first ablation element may have a coiled configuration, and wherein the second ablation element may have a coiled configuration. A coiled configuration of the first ablation element may be the same in all regards as a coiled configuration of the second ablation element. A coiled configuration of the first ablation element may be different than a coiled configuration of the second ablation element in at least one way.

In this ninth additional example, the first ablation element may have a different length than the second ablation element.

In this ninth additional example, the first ablation element may have a different coil direction (e.g. left handed vs right handed) than the second ablation element.

In this ninth additional example, the first ablation element may have a different pitch than the second ablation element.

In this ninth additional example, the first ablation element may have a different wire thickness than the second ablation element.

In this ninth additional example, an OD of the distal section at the location of the first ablation element may be different than an OD of the distal section at the location of the second ablation element.

In this ninth additional example, a first ablation element and a second ablation element may each have either a curvilinear (e.g. circular) or rectilinear (e.g., rectangular) cross sectional outer profile.

In this ninth additional example, a first ablation element and a second ablation element may be a superelastic material such as nitinol.

In this ninth additional example, a first ablation element and a second ablation element may be sufficiently flexible to allow the distal section to be advanced from an azygos vein into one of a T9, T10, or T11 intercostal vein.

In this ninth additional example, at least one of a first and second ablation elements may be made from a laser cut tubular element (e.g., a nitinol tube).

In this ninth additional example, at least one of a first and second ablation elements may comprise a wire mesh or braid.

In this ninth additional example, at least one of a first and second ablation elements may be a ring electrode having a length not more than 5 mm, optionally around 3 mm.

In this ninth additional example, each of a first and second ablation elements may have a length from 1 mm-12 mm, optionally from 2 mm-12 m, optionally from 5 mm-12 mm, optionally from 6 mm-11 mm, optionally from 7 mm-10 mm, such as around 8 mm.

In this ninth additional example, an axial spacing between a first and second ablation elements may be from 0 mm-8 mm, such as from 0 mm-5 mm, such as from 0.5 mm-5 mm, such as from 1 mm-4 mm.

In this ninth additional example, an ablation element total axial length may be from 1 mm-25 mm, optionally from 2 mm-22 mm, optionally from 5 mm-20 mm, optionally 8 mm-20 mm, optionally 10 mm-20 mm, optionally 10 mm-18 mm, optionally, preferably 10 mm-15 mm.

In this ninth additional example, the ablation element, and optionally both of a first and second ablation elements, may have an expandable diameter.

In this ninth additional example, the ablation element may comprise a plurality of ablation elements, of which first and second ablation elements may be part of and may define the entirety of the plurality of ablation elements.

In this ninth additional example a plurality of ablation elements may be configured to be independently energized in monopolar mode (with a ground pad).

In this ninth additional example, any two of a plurality of ablation elements may be configured to be energized in bipolar mode.

In this ninth additional example, the catheter may include a temperature sensor disposed between the first and second ablation elements and carried by the shaft.

In this ninth additional example, the catheter may further comprise one or more of a temperature sensor distal to a distal ablation element, or a temperature sensor proximal to a proximal ablation element.

In this ninth additional example, the catheter may include at least one irrigation port in fluid communication with an irrigation lumen that is connectable to a fluid source at a proximal region of the ablation catheter. The ablation catheter may further comprise a second irrigation port distal to the proximal ablation element.

In this ninth additional example, the catheter may include one or more irrigation ports between a distal end and a proximal end of a distal ablation member, optionally between the windings of a coiled distal ablation member.

In this ninth additional example, the catheter may comprise one or more irrigation ports between a distal end and a proximal end of a proximal ablation member, optionally between the windings of a coiled proximal ablation member.

In this ninth additional example, the catheter may include one or more irrigation ports under any of the flexible ablation elements, such as a distal ablation element and/or a proximal ablation member.

In this ninth additional example, the catheter may further comprise a deployable element carried by the shaft (optionally expandable). A deployable element may be distal to the ablation element, optionally distal to a distal ablation element. A deployable element may be inflatable, and wherein the shaft may include an inflation port within the inflatable deployable element. A deployable element may have a delivery configuration and a deployed configuration with an OD greater than the delivery configuration. A deployable element may have an OD from 3-6 mm in the deployed configuration, such as 4 mm-6 mm. A deployable element may have an OD that is equal to or greater than the OD of the shaft in the distal section by no more than 0.2 mm. A deployable element may comprise at least one of the following: a balloon, a bellowed member, or a coated stent or coated stent-like device (e.g., a reinforcing member coated with a one or more layers of material).

In this ninth example, the ablation catheter may further comprise a proximal deployable element carried by the shaft proximal to the ablation element, which may be proximal to a proximal ablation element. A proximal deployable element may be inflatable, and wherein the shaft may include an inflation port within the proximal deployable element. A proximal deployable element may have a delivery configuration and a deployed configuration with an OD greater than the delivery configuration. A deployable element may have an OD from 4-10 mm in the deployed configuration, and optionally larger than an OD of a distal deployable member. A proximal deployable element may have an OD that is equal to or greater than the OD of the shaft in the distal section by no more than 0.2 mm. A proximal deployable element may comprise at least one of the following: a balloon, a bellowed member, or a coated stent or coated stent-like device (e.g., a reinforcing member coated with a one or more layers of material).

In this ninth additional example, the catheter may include a central deployable element. A central deployable element may include any of the features, including any combination thereof, of a distal or proximal deployable member herein.

In this ninth additional example, the catheter is configured for transvascular ablation of a GSN. The ablation catheter may include a distal section that includes the distal-most 7 cm of the ablation catheter. The ablation element may be adapted to create an ablation having a length in a range of 5 mm to 25 mm.

In this ninth additional example, a distal section may be adapted for flexibly traversing a bend from an azygos vein to a T9-T11 intercostal vein (e.g., having a radius of curvature >=5 mm, angle as much as 120 degrees.

In this ninth additional example, an outer diameter of the distal section (at least in a delivery state) is in a range of 1.5 to 3 mm.

In this ninth additional example, the ablation catheter may further comprise a guidewire lumen within the elongate shaft.

In this ninth additional example, a total length of the ablation element (which may comprise a plurality of individual ablation elements) may be from 5 mm to 20 mm, such as 10 to 15 mm.

In this ninth additional example, any of the ablation elements may comprise one or more of an RF ablation electrode, a coiled wire electrode, a laser cut RF electrode, a RF electrode printed with conductive ink, a RF electrode on an expandable balloon (e.g., conductive ink, flexible circuits,), a conductive membrane RF electrode, a RF electrodes on an expandable cage or mesh, an ultrasound ablation transducer, an electroporation electrodes, an cryoablation element, or a virtual RF electrode.

In this ninth additional example, the ablation element may be adapted to deliver ablation energy circumferentially (radially symmetric around the ablation element/around the vessel).

In this ninth additional example, the catheter may further include a proximal radiopaque marker positioned on the shaft at or proximal to a proximal end of the ablation element.

In this ninth additional example, the catheter may further a distal radiopaque marker positioned on the shaft distal to a distal end of the ablation element(s).

In this ninth additional example, the catheter may include an axial space between a distal radiopaque marker and a distal end of the ablation element.

Any of the methods in any of the additional methods may be used with any of catheters in the additional examples. Any of the catheters in the additional examples may be used with methods herein or used in ways that are not described herein.

What is claimed is:

1. A system for ablating a greater splanchnic nerve from within an intercostal vein, the system comprising:
    an ablation catheter, including:
        an elongate shaft having a length such that at least a portion of a distal section of the elongate shaft can be positioned in a T9, T10, or T11 intercostal vein, the distal section having a linear configuration when radially unconstrained,
        a guidewire lumen extending through the elongate shaft and including an exit port at a distal end of the distal section,
        distal and proximal electrically conductive flexible and coiled ablation electrodes carried by and disposed circumferentially about the distal section,
        the distal and proximal electrically conductive flexible and coiled ablation electrodes together having an axial length from 5 mm-25 mm and an axial spacing therebetween that is not more than 2.0 mm,
        a plurality of distal electrode irrigation ports in a helical configuration disposed within the distal section and between windings in at least a central section of the distal electrode, wherein the windings in the at least a central section of the distal electrode are axially spaced apart such that the plurality of distal electrode irrigation ports are not radially underneath the windings and are visible in a side view of the distal section,
        a plurality of proximal electrode irrigation ports in a helical configuration disposed within the distal section and between windings in at least a central section of the proximal electrode, wherein the windings in the at least a central section of the proximal electrode are axially spaced apart such that the plurality of proximal electrode irrigation ports are not radially underneath the windings and are visible in a side view of the distal section,
        a plurality of distal irrigation ports distal to the distal electrode, the plurality of distal irrigation ports axially aligned and spaced circumferentially around the distal section,
        a plurality of central irrigation ports axially between the distal electrode and proximal electrode, the plurality of central irrigation ports axially aligned and spaced circumferentially around the distal section; and
    an external device or system adapted to be coupled to the ablation catheter so as to create operable communication with the ablation catheter, the external device or system including:
        a power output module adapted to deliver a first waveform of ablative RF energy with an initial power from 15-50 W and a second waveform of ablative RF energy with an initial power from 15-50 W, and
        a module adapted to receive information indicative of at least one of a sensed temperature or measured impedance and determine if at least one of the sensed temperature or the measured impedance is at or above a limit, and if at least one of the sensed temperature or the measured impedance is at or above a threshold limit, cause the power output module to decrease the power of at least one of the first waveform and the second waveform.

2. The system of claim 1, wherein the module comprises at least one of a temperature limit module or an impedance limit module.

3. The system of claim 1, wherein if at least one of the sensed temperature or the measured impedance is at or above a threshold limit, and a minimum therapy time has not yet passed, the module is adapted to cause the power output module to reduce the power of at least one of the first waveform and second waveform to a secondary power less than the initial power.

4. The system of claim 3, wherein the secondary power is greater than zero and is from 5-10 W less than the initial power.

5. The system of claim 1, wherein if at least one of the sensed temperature or the measured impedance is at or above a threshold limit, and a minimum therapy time has passed, the module is adapted to cause the power output module to reduce the power of at least one of the first waveform and second waveform to a secondary power between 0 W and 1 W.

6. The system of claim 1, wherein the power output module is adapted to deliver cyclical asynchronous first and second waveforms.

7. The system of claim 1, wherein the power output module is adapted to deliver the first waveform of ablative RF energy with an initial power of 25 W and the second waveform of ablative RF energy with an initial power of 25 W.

8. The system of claim 1, wherein the module is adapted to determine if the sensed temperature is at or above 40° C. to 95° C., optionally at or above 90° C.

9. The system of claim 1, wherein the module is adapted to determine if the measured impedance is at or above 200 to 500 ohms, optionally at or above 500 ohms.

10. The system of claim 1, wherein the power output module is adapted with a default setting to deliver the ablative energy from 30 seconds to 180 seconds.

11. The system of claim 1, wherein the power output module is adapted to deliver the first waveform of ablative RF energy with an initial power from 20 W to 50 W and the second waveform of ablative RF energy with an initial power from 20 W to 50 W.

12. The system of claim 1, wherein the plurality of distal irrigation ports are equidistantly spaced circumferentially around the distal section, and wherein the plurality of central irrigation ports are equidistantly spaced circumferentially around the distal section.

* * * * *